(12) United States Patent
Fanucchi et al.

(10) Patent No.: US 10,167,466 B2
(45) Date of Patent: Jan. 1, 2019

(54) SITE-SPECIFIC NUCLEASE SINGLE-CELL ASSAY TARGETING GENE REGULATORY ELEMENTS TO SILENCE GENE EXPRESSION

(71) Applicant: CSIR, Pretoria (ZA)

(72) Inventors: Stephanie Fanucchi, Johannesburg (ZA); Youtaro Shibayama, Pretoria (ZA); Shaun Burd, Pretoria (ZA); Musa M. Mhlanga, Johannesburg (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 14/916,338

(22) PCT Filed: Sep. 4, 2014

(86) PCT No.: PCT/IB2014/064259
§ 371 (c)(1),
(2) Date: Mar. 3, 2016

(87) PCT Pub. No.: WO2015/033293
PCT Pub. Date: Mar. 12, 2015

(65) Prior Publication Data
US 2016/0215280 A1 Jul. 28, 2016

(30) Foreign Application Priority Data
Sep. 4, 2013 (ZA) .................. 2013/06649

(51) Int. Cl.
| | | |
|---|---|---|
| *C12N 15/85* | (2006.01) | |
| *C12N 15/01* | (2006.01) | |
| *C12N 9/22* | (2006.01) | |
| *C12N 15/63* | (2006.01) | |
| *C12Q 1/6841* | (2018.01) | |
| *C12Q 1/6876* | (2018.01) | |

(52) U.S. Cl.
CPC .............. *C12N 15/01* (2013.01); *C12N 9/22* (2013.01); *C12N 15/63* (2013.01); *C12Q 1/6841* (2013.01); *C12Q 1/6876* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

2009/0305402 A1* 12/2009 Liljedahl ............ A01K 67/0275
435/349
2010/0160417 A1* 6/2010 Lawrence ............ A61K 48/005
514/44 R

OTHER PUBLICATIONS

Satoh et al (Mutation Research, 2006. vol. 596, pp. 36-42).*
International Search Report from corresponding PCT/IB2014/064259, dated Jan. 12, 2015.
International Preliminary Report on Patenability from corresponding PCT/IB2014/064259, completed on Jan. 23, 2015.
Kim et al., "Hybrid restriction enzymes: Zinc finger fusions to Fok I cleavage domain" Proceedings of the National Academy of Sciences. (Feb. 6, 1996) vol. 93, No. 3: 1156-1160.
Cong et al., "Multiplex Genome Engineering Using CRISPR/Cas Systems" Science. (Feb. 15, 2013) vol. 339: 819-823.
Li et al., "Extensive Promoter-Centered Chromatin INteractions Provide a Topological Basis for Transcription Regulation" Cell (Jan. 20, 2012) vol. 148: 84-98.
Larkin et al., "Dynamic Reconfiguration of Long Human Genes during One Transcription Cycle" Molecular and Cellular Biology. (Jul. 2012) vol. 32, No. 14: 2730-2747.
Noordermeer et al., "Variegated gene expression caused by cell-specific long-range DNA interactions" Nature Cell Biiology. (Aug. 2011) vol. 13, No. 8: 944-966.
Fanucchi et al., "Chromosomal Contact Permits Transcription Between Coregulated Genes" Cell. (Oct. 24, 2013) vol. 155, No. 3: 606-620.
Banos et al., "Stochastic Responses Are Not Left to Pure 'Chance'" Cell. (Oct. 24, 2013) vol. 155, No. 3: 499-502.
Written Opinion of the International Search Authority from corresponding PCT/IB2014/064259, dated Dec. 3, 2015.

* cited by examiner

*Primary Examiner* — Celine X Qian
(74) *Attorney, Agent, or Firm* — McBee Moore Woodward & Vanik IP, LLC; Susan McBee

(57) ABSTRACT

This invention relates to a single cell assay for determining the effect of chromosomal contact on the transcriptional activity of genes of interest in a cell and to methods of silencing gene expression in a cell by way of perturbing gene regulatory elements which are engaged in chromosomal contact.

12 Claims, 36 Drawing Sheets

Specification includes a Sequence Listing.

I. Enhancer/promoter interactions

Enhancer regulatory elements induce gene expression via looping

Inducing a DSB within the enhancer regulatory region prevents loop-mediated contact and abrogates gene expression III. Regulatory sites that determine loop structure CTCF binds to regulatory sequences and mediates loop formation and gene expression Inducing a DSB within CTCF binding sites prevents loop formation and abrogates gene expression

A.

B.

SITE-SPECIFIC NUCLEASE SINGLE-CELL ASSAY TARGETING GENE REGULATORY ELEMENTS TO SILENCE GENE EXPRESSION

CROSS REFERENCE TO RELATED APPLICATIONS

This application is a § 371 National Stage Application of PCT/IB2014/064259, filed 4 Sep. 2014 which claims priority to EP 13182222.3, filed 4 Sep. 2013.

BACKGROUND

Field of the Invention

Description of Related Art

This invention relates to a single cell assay for determining the effect of chromosomal contact on the transcriptional activity of genes of interest in a cell and to methods of silencing gene expression in a cell by way of perturbing gene regulatory elements which are engaged in chromosomal contact.

Gene regulation begins with signal transduction cascades resulting in transcription in the nucleus. Gene expression is inherently stochastic with transcription occurring in bursts as gene switch from inactive to active states. Attempts have been made to decipher gene expression and relate it to biological noise and stochasticity, while simultaneously accounting for cell-to-cell variation.

The highly conserved endogenous eukaryotic RNA interference (RNAi) pathway is the standard approach used to silence gene expression. This approach involves the transfection of exogenous small interfering RNAs (siRNA) and analysis of alterations in gene expression at a population level. Therefore, siRNA-approaches fail to reveal cell-to-cell variability. Off-target effects represent another major challenge in the use of siRNA as gene knockdown tools.

The eukaryotic nucleus is an immensely crowded, yet paradoxically, highly organized environment. Its main constituent, DNA, is folded many times over reducing its one-dimensional length by over one million fold in space. Due to this tight compaction, regions of looped chromatin are permitted to interact or "kiss."

By identifying sites where DNA interacts, the population based chromosome conformation capture (3C) and derivative techniques (4C, 5C, HiC, ChIA-PET) allow the characterization of the global interactome (Dekker et al., 2002, Fullwood et al., 2009). Analyses of Hi-C data reveal that chromatin is divided into smaller chromosomal interacting domains, referred to as topologically associating domains (TADs), which range in size from several hundred Kb to ~3 Mb (Lieberman-Aiden et al., 2009). By constraining the DNA topology, TAD structure may enhance the probability of specific loop-mediated interactions occurring thus playing a direct role in transcriptional activity.

The subdivision of the genome into subchromosomal domains, or TADs, represents a highly conserved feature of chromosomal organization (Dixon et al., 2012). This suggests that each cell across a population would possess a generally similar arrangement of its chromosomes. Paradoxically, traditional in situ studies reveal a large degree of heterogeneity across a population of genotypically identical cells (Li et al., 2012). Since C-techniques report an ensemble of many nuclei, the dynamic nature of TAD structure at the single cell level and any consequent effects on transcription are obscured in the data. Clearly, interrogating chromosomal interactions at the level of a single cell is imperative to the interpretation of global interactome studies.

A characteristic feature of TADs is the enrichment of intra-domain chromatin contacts. FISH results confirm a spatial distinction between domains and contact arrangements within domains, as loci within a single domain are closer in nuclear space than those in different domains despite having similar genomic distances from one another. TADs therefore may provide a layer of structural regulation governing the principle of long-range chromatin contact.

Within TADs, and/or at the interface between TADs, chromosomal contact is strongly correlated with the transcriptional activity of interacting DNA elements (Li et al., 2012). Recently, we developed a novel single cell microscopy-based assay, to directly address the role of loop-mediated contact on the transcription of interacting genes. Using this assay, we demonstrated that chromosomal contact plays a central role in supporting transcription of co-regulated genes.

The invention described here relates to this single cell assay to silence gene expression through the discrete targeting (by cutting) of gene regulatory elements engaged in chromosomal contact. Major regulatory elements include; (I) enhancers, (II) sites within chromatin loops that engage in intra- or interchromosomal contact in multigene complexes and (III) regulatory sites within chromatin loops that determine loop structure.

Transcription of co-regulated genes occurs concurrently with long-range chromosomal contacts to form multigene complexes. Such contacts and transcription are lost in knockout studies of transcription factors and structural chromatin proteins. However, these approaches do not reveal the necessity of chromosomal contacts for cotranscription in multigene complexes. To interrogate in a discrete manner the role of loop-mediated contact on co-transcription, we devised a novel strategy using TALENs to cleave and disrupt gene loops in a well-characterized multigene complex. Monitoring this disruption using RNA FISH and immunofluorescence microscopy revealed that perturbing the site of contact has a direct effect on transcription of other interacting genes. Unexpectedly this effect on co-transcription was hierarchical, with dominant and subordinate members of the multigene complex engaged in both intra- and inter-chromosomal contact. This observation reveals the unprecedented level of influence of these chromosomal contacts on the transcription of co-regulated genes in a multigene complex. Transcription is replete with proximal and distal chromatin looping interactions whose formation represents the basic organizing principle of nuclear architecture and gene activity (Tan-Wong et al., 2012). Loop-mediated chromosomal contacts are usually identified on a genome-wide scale using population-based 'chromosome conformation capture' (3C) technologies (Dekker et al., 2002; Fullwood et al., 2009; Lieberman-Aiden et al., 2009; Li et al., 2012). Analyses of 3C-based data reveal a large heterogeneity in global chromatin interactions (Fullwood et al., 2009; Noordermeer et al., 2011; Li et al., 2012). Therefore, interacting DNA elements identified by 3C-based technologies are verified at the single cell level using fluorescent in situ hybridization (FISH) assays (Papantonis et al., 2012). These highly sensitive assays can target either DNA or nascent mRNA, and have revealed the co-localization between FISH foci in a fraction of the population (Papantonis et al., 2010). This suggests that a subset of cells within the population may be enriched for specific chromosomal interactions. Chromosomes are large and constrained in their ability to roam the entire nuclear volume. Thus, it is reasonable to surmise that the topological arrangements after each cellular division shuffle chromosomal proximities such that their 3D arrangements are altered in 1D space. This may lead to every cell in the population possessing unique spatial arrangements of its chromosomes.

Enhancer-promoter interactions utilize chromatin looping to trigger dynamic changes in transcription initiation (Deng et al., 2012). An example of this is the well-established model between the locus control region (LCR) and the promoter of the β-globin gene. In a tissue-specific manner, the LCR has been shown to physically contact the promoter of the β-globin gene, and initiate transcription (Deng et al., 2012). These LCR-mediated chromosomal interactions have been shown to result in variability in β-globin genes transcript levels, or variegated gene expression, across the population (Noordermeer et al., 2011). In an otherwise identical population of cells, presumably through chromosomal interactions, such "jackpot" cells display higher levels of β-globin transcription (Noordermeer et al., 2011). Accordingly, the specific set of chromosomal interactions (and consequent gene expression that may depend on LCR-mediated interactions) will vary between cells across the population. This heterogeneity reveals the absolute requirement of single cell analysis in global interactome and gene loop studies.

Looping also brings distal genes into close proximity, enabling chromosomal contact in "multigene complexes" at a single focus of multiple RNA polymerases (Papantonis et al., 2012; Li et al., 2012). Numerous studies have demonstrated that the formation of loop-mediated contact coincides with alterations in gene expression (Fullwood et al., 2009). Indeed, chromosomal contacts in multigene complexes appear to be the main modality of transcription in metazoan cells, as they are associated with over 95% of transcriptional activity (Li et al., 2012). In a comparable manner to enhancer-promoter interactions, specific chromatin interactions in multigene complexes are detected in a subset of cells within the population (Papantonis et al., 2010). Genome-wide chromatin interaction analysis with paired end tags (ChIA-PET), uncovered a multigene complex including the GREB1 locus and 3 other genes (Li et al., 2012). Of the 4 interacting genes, only GREB1 transcription is activated by the estrogen receptor-α (ERα) (Li et al., 2012). Intriguingly, despite the fact that this multigene complex may not assemble in every cell in the population, siRNAs targeting ERα disrupted all 4 interacting genes (Li et al., 2012). Therefore, even though these chromosomal contacts may only occur in a fraction of the population they clearly play a significant role in gene regulation. Moreover, this data supports a model of synergistic transcription, where chromosomal contact influences the transcription of the interacting genes. This would connote that the topological framework for transcriptional regulation is physical contact via chromosomal looping in multigene complexes.

Current siRNA and 3C-based experimental approaches cannot be applied to multigene complexes where all interacting genes are activated by the same transcription factor. Tumor necrosis factor alpha (TNFα) has been shown to induce the formation of such multigene complexes, where all interacting genes are activated by NF-κB (Papantonis et al., 2012). Ten minutes after TNFα stimulation, the promoters of genes located on the same chromosome (SAMD4A and TNFAIP) and on a different chromosome (SLC6A5) associate to form a NF-κB-dependent multigene complex (Papantonis et al., 2010). RNA FISH assays targeting the approximate sites of interaction identified by 3C, suggest an association between the formation of this NF-κB-regulated multigene complex and the co-transcription of interacting genes (Papantonis et al., 2010). However, both 3C and FISH approaches fail to reveal the necessity of chromosomal contacts for co-transcription of these interacting genes. Therefore, to accurately interrogate a model of synergistic regulation, a discrete perturbation of a single site within a gene loop, whilst monitoring the transcriptional status of other members of the multigene complex, is required. Importantly, owing to variegated gene expression (Noordermeer et al., 2011), this can only be achieved with a single cell approach.

Here we devise a single cell strategy using TALE nucleases (TALENs) to discretely perturb sites within gene loops that are established to engage in chromosomal contact in the well-characterized NF-κB-regulated multigene complex (Papantonis et al., 2010). This enabled us to address the longstanding question of the requirement of loop-mediated contact for transcriptional co-regulation in a multigene complex. Using RNA FISH and immunofluorescence (IF), we imaged the site of the disrupted loop simultaneously with the transcriptional activity of other interacting genes in the NF-κB-regulated multigene complex. This unique single cell perspective revealed that perturbing loop-mediated contact between the NF-κB-regulated genes, altered the transcriptional status of interacting genes. In addition, this effect on co-transcription was hierarchical, with dominant and subordinate members of the multigene complex engaged in intra-chromosomal contact at distances over 48 mbp, as well as inter-chromosomal interactions. Furthermore, restoration of a disrupted gene loop re-established both chromosomal contacts and transcription of interacting genes in a sequenceindependent manner. The unexpected hierarchical organization within the TNFα-induced multigene complex reveals the unprecedented level of influence of these chromosomal contacts on the transcription of co-regulated genes in a multigene complex.

SUMMARY OF THE INVENTION

The present invention relates to a method for silencing gene expression and an assay for determining the effects of chromosomal contact on gene silencing.

In a first aspect of the invention there is provided for a method for silencing gene expression at a single cell level. The method includes a step of perturbing or interfering with at least one chromosomal contact in the cell. The point of chromosomal contact may include any region of chromatin and/or DNA. The method further includes a step of detecting the site of perturbation of the chromosomal contact; and further includes a step of detecting the effect of the perturbation of chromosomal contact on the transcriptional activity of a gene of interest. It will be appreciated, that a gene of interest may include a single gene and or a multigene complex.

In one embodiment, the chromosomal contact is perturbed by inducing a site-specific double stranded break in the chromatin or DNA.

In another embodiment, the transcriptional activity of the gene of interest may be abrogated or prevented by recruitment of proteins involved in a repair process to the site of the double stranded break, which when bound to the chromatin or DNA at the site of the double stranded break obstruct chromosomal contacts. Alternatively, the transcriptional activity of the gene of interest may be abrogated or prevented by means of enhancement of mobility of the region of chromatin or DNA containing the double stranded break, which results in a reduction in the capacity of a gene loop to engage in chromosomal contact. In a further alternative, the transcriptional activity of the gene of interest may be abrogated or prevented through the loss of structural integrity of a gene loop, which results in the abrogation of chromosomal contact.

In yet another embodiment of the invention, the chromosomal contact may be an intergenic contact, an intragenic contact or both an intergenic and intragenic contact.

In another embodiment of the invention, the region of chromatin or DNA that is perturbed or interfered with may comprise a gene or regulatory element selected from the group consisting of an enhancer and/or promoter, a site within a chromatin or DNA loop that engages in intra-chromosomal or inter-chromosomal contact, or a regulatory site within a chromatin or DNA loop which determines the loop structure. It will be appreciated that the chromosomal contact may be between chromatin and/or DNA located either inter-chromosomally, intra-chromosomally or both inter-chromosomally and inter-chromosomally.

In yet another embodiment of the invention the double stranded break may be induced by a site-specific nuclease. The site-specific nuclease may be selected from the group consisting of a meganuclease, a zinc finger nuclease, a TALE nuclease, a BUD1 nuclease, and a CrispR nuclease. It will be appreciated that the site-specific nuclease may be delivered to the cell by transfection of the cell with a vector encoding the site-specific nuclease and wherein the site-specific nuclease is endogenously expressed in the cell. Alternatively, the site-specific nuclease may be exogenously expressed and the exogenously expressed site-specific nuclease may consequently delivered to the cell.

In yet another embodiment of the invention, the double stranded break is detected by the immunofluorescent staining of a protein involved in a cellular repair process in the cell, or by detecting the location of a recombinant protein expressing a fluorescent label which is involved in a cellular repair process in the cell.

In a further embodiment of the invention, the effect of the double stranded break on the transcriptional activity of the gene of interest is detected using a method selected from the group consisting of RNA fluorescent in situ hybridisation, live RNA fluorescent in situ hybridisation, immunogold labelling, molecular beacons and MS2 tagging.

In yet another embodiment of the invention the cell is a eukaryotic cell or prokaryotic cell.

A second aspect of the invention provides for a single cell assay for determining the effect of chromosomal contact on the transcriptional activity of at least one gene of interest in a cell. In one embodiment, a site-specific nuclease is used to induce or cause a double stranded break in a region of chromatin or DNA which is engaged in chromosomal contact in the cell. Consequently, an immunofluorescent probe or recombinant protein expressing a fluorescent label is used to detect the site of the double stranded break and one or more fluorescent oligonucleotide probes which are capable of hybridising to a target mRNA sequence produced by the transcription of at least one gene of interest are used to detect the presence or absence of transcription of the gene of interest by monitoring the fluorescence and the relative intensity of fluorescence of the fluorescent oligonucleotide probe hybridised to the target mRNA sequence. The fluorescence and relative intensity of fluorescence will be indicative of the effect of the chromosomal contact on the transcriptional activity of the gene of interest.

In one embodiment, of this aspect of the invention the transcriptional activity of the gene of interest may be abrogated or prevented by recruitment of proteins involved in a repair process to the site of the double stranded break, which when bound to the chromatin or DNA at the site of the double stranded break obstruct chromosomal contacts. Alternatively, the transcriptional activity of the gene of interest may be abrogated or prevented by means of enhancement of mobility of the region of chromatin or DNA containing the double stranded break, which results in a reduction in the capacity of a gene loop to engage in chromosomal contact. In a further alternative, the transcriptional activity of the gene of interest may be abrogated or prevented through the loss of structural integrity of a gene loop, which results in the abrogation of chromosomal contact.

In another embodiment, the chromosomal contact may be an intergenic contact, an intragenic contact or both an intergenic and intragenic contact.

In a further embodiment, the double stranded break perturbs or interferes with the chromatin or DNA engaged in chromosomal contact and consequently perturbs or interferes with the transcriptional activity of the gene of interest.

In another embodiment of the invention, the region of chromatin or DNA that is perturbed or interfered with may comprise a gene or regulatory element selected from the group consisting of an enhancer and/or promoter, a site within a chromatin or DNA loop that engages in intra-chromosomal or inter-chromosomal contact, or a regulatory site within a chromatin or DNA loop which determines the loop structure.

In yet another embodiment of the invention, the double stranded break may be induced by a site-specific nuclease. The site-specific nuclease may be selected from the group consisting of a meganuclease, a zinc finger nuclease, a TALE nuclease, a BUD1 nuclease, and a CrispR/Cas 9 nuclease. It will be appreciated by those skilled in the art that the site-specific nuclease may be delivered to the cell by transfection of the cell with a vector encoding the site-specific nuclease and wherein the site-specific nuclease is endogenously expressed in the cell. Alternatively, the site-specific nuclease may be exogenously expressed and the exogenously expressed site-specific nuclease may consequently delivered to the cell.

In yet another embodiment of the invention the immunofluorescent probe may be an antibody which binds to at least one of the proteins involved in the cellular repair process of a double strand break in the cell.

In another embodiment, the location of the hybridized fluorescent oligonucleotide probes in the cell is observable by a technique selected from the group consisting of diffraction limited imaging techniques, sub-diffraction limit image resolution and other imaging techniques, such as imaging in three dimensions, wherein detection of the chromosomal location of gene expression for the target mRNA sequences and the diffraction limited or sub-diffractive location of the hybridised immunofluorescent probe is indicative of the location of the double stranded break.

In yet another embodiment, the cell is a eukaryotic cell or prokaryotic cell.

BRIEF DESCRIPTION OF THE FIGURES

Non-limiting embodiments of the invention will now be described by way of example only and with reference to the following figures:

FIGS. 23, 24, 27, 28, 29, 30, 31, 33, 34, 36, 37, 38, 39, 40, 42 and FIG. 36: TALEN-mediated disruption of the SLC6A5 gene loop abrogates SLC6A5 gene expression. The SLC6A5 TALEN targets the approximate region in intron 1 involved in chromosomal contact at 10 min post TNFα stimulation. Left and right TALENs were designed to contain 18 full monomer repeats and target a 20 bp target region, where the first and last space specify the T at the N terminus and the 0.5 repeat respectively.

FIG. 37: TALEN-mediated disruption of the SLC6A5 gene loop abrogates SLC6A5 gene expression. Post 24 hr transfection, ~60% of cells displayed SLC6A5 TALEN-induced DSBs and low levels of apoptotic cells, as evidenced by cells displaying multiple breaks (more than 2). Consistent with SAMD4A and TNFAIP2 TALENs, a higher portion of transfected cells displayed single allelic DSBs as opposed to dual allelic DSBs.

FIG. 38: TALEN-mediated disruption of the SLC6A5 gene loop abrogates SLC6A5 gene expression. The SLC6A5 TALEN abrogates transcription downstream of the DSB. Dual-transfected HUVECs were stimulated with TNFα for 10 min to allow for the first ~1.5 kbp of SLC6A5 to be transcribed. Nascent intronic SLC6A5 (Atto647N) RNA transcribed downstream of the DSB (H2A.X-Atto488) was never observed. Two-tailed Fisher exact test; ***P<0.001. Cells were counterstained with DAPI. Bar, 5 µm.

FIG. 39: TALEN-mediated disruption of the SLC6A5 gene loop abrogates SLC6A5 gene expression. TNFα induces SLC6A5 protein expression 16 hr post stimulation. Cells were counterstained with DAPI. Bar 5 µm.

FIG. 40: TALEN-mediated disruption of the SLC6A5 gene loop abrogates SLC6A5 gene expression. Disrupting the SLC6A5 gene loop is sufficient to abrogate protein expression. Dual indirect immunofluorescence of SLC6A5 and H2A.X (DSBs) was performed using a donkey-anti rabbit antibody conjugated to Atto488 and donkey-anti-goat conjugated to Atto565 respectively. DSBs, as detected by H2A.X, displayed a significant reduction in protein expression. R.F.U., relative fluorescent units, mean±SD, **P<0.01, Two-tailed unpaired Students t test, cells were counterstained with DAPI, Bar, 5 µm.

FIG. 42: Comparison between the phenotype in cells displaying a single allelic DSB to cells displaying dual allelic DSBs. Transcription, as well as co-localization of SAMD4A and TNFAIP2 was not affected in cells harboring both single allelic or dual allelic SLC6A5 TALEN mediated DSBs. n, number of DSBs. Cells were counterstained with DAPI. Bar, 5 µm.

DETAILED DESCRIPTION OF A PREFERRED EMBODIMENT

Figure 1:
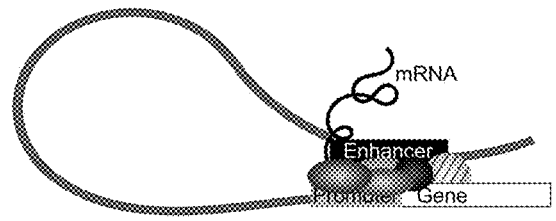
FIG. 1: Enhancer-promoter interactions. Enhancer-promoter interactions utilize looping to trigger dynamic changes in transcription. An example of this is the well-established model between the locus control region (LCR) and the promoter of the β-globin gene. These LCR-mediated chromosomal interactions have been shown to result in variability in β-globin genes transcript levels, or variegated gene expression, across the population (Noordmeer et al., (2011)). Therefore, preventing enhancer-promoter interactions will have a significant impact on gene expression. To date, no assay exists to discretely perturb enhancer elements to silence gene expression.
Figure 1:

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention.

Although specific terms are employed herein, they are used in a generic and descriptive sense only and not for purposes of limitation. As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The terms "nucleic acid" or "nucleic acid molecule" encompass both ribonucelotides (RNA) and deoxyribonucleotides (DNA), genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides.

The term "chromatin" refers to the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA which extends between nucleosome cores. For the purposes of the present disclosure, the term "chromatin" is meant to encompass all types of cellular nucleoprotein, both prokaryotic and eukaryotic.

The term "gene of interest," refers to a nucleic acid sequence comprising a nucleotide sequence which includes a transcription unit, and which can be transcribed and translated into a protein. Using the methods and/or assay of the present invention the expression of a gene of interest may be interrupted or silenced as a result of perturbation of a chromosomal contact in the cell.

Chromosomal contact may be perturbed by means of by interfering with a region of chromatin or DNA in a cell, resulting in the abrogation of the transcriptional activity of a gene of interest. Transcriptional activity may be abrogated, stopped, prevented or decreased as a result of recruitment of proteins involved in DNA repair to a site of a double stranded break in the chromatin or DNA in a cell. As a result of the recruitment of these proteins chromosomal contact may be prevented. Alternatively, chromosomal contact may be perturbed by a protein which interferes with the transcriptional machinery of a cell as a result of being "parked" at a site of chromosomal contact and thus occluding chromosomal contact or blocking the assembly of transcription machinery at the site where the protein is parked, a non-limiting example of such a protein would include a deactivated Cas9 protein, which when bound to the chromatin or DNA obstructs chromosomal contact. Typically chromosomal contact is disrupted or prevent by the introduction of a double stranded break in the DNA.

Chromosomal contact may also be disrupted as a result of the enhancement of mobility of a region of chromatin or DNA which is in the vicinity of a double stranded break. Increased mobility of the region of chromatin or DNA results in a reduction in the capacity of a gene loop to engage in chromosomal contact, as a result the transcriptional activity of the gene of interest will be negatively affected.

Chromosomal contact may further be affected by the loss of structural integrity of a gene loop as a result of a double stranded DNA break, which results in the prevention of chromosomal contact, and consequently the disruption of transcriptional activity.

The terms "protein," "peptide" or "polypeptide" refers to any chain of two or more amino acids, including naturally occurring or non-naturally occurring amino acids or amino acid analogues, irrespective of post-translational modification (e.g., glycosylation or phosphorylation).

The term "recombinant" means that something has been recombined. When used with reference to a nucleic acid construct the term refers to a molecule that comprises nucleic acid sequences that are joined together or produced by means of molecular biological techniques. The term "recombinant" when used with reference to a protein or polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering. Recombinant nucleic acid constructs may be introduced into a host cell by transformation. Such recombinant nucleic acid constructs may include sequences derived from the same host cell species or from different host cell species.

The present invention relates to a single cell assay to silence gene expression through the discrete targeting (by cutting) of gene regulatory elements engaged in chromosomal contact. It will be appreciated that the cell used in the assay may be selected from a eukaryotic or prokaryotic cell. It will be further appreciated that a eukaryotic cell may include, without limitation, a cell selected from a diploid or polyploid cell line, a diploid or polyploid oncogenic cell, a primary cell, stem cell, pluripotent stem cell or tissue sample or any other eukaryotic cell.

It will be appreciated by those of skill in the art that the fluorescent moiety used in the methods of the invention may include fluorophore selected from the group consisting of the Alexafluor family of dyes, FAM, TET or CAL FluorGold 540, HEX or JOE, VICB, CAL Fluor Orange 560A; Cy3C or NEDB, Quasar 570A, Oyster 556D; TMR or CAL Fluor Red 590A; ROX or LC red 610E, CAL FLuor Red 610A; Texas red or LC red 610E, CAL Fluor Red 610A; LC red 640E or CAL Fluor Red 635A; Cy5C or LC red 670E, Quasar 670A, Oyster 645D; LC red 705E or Cy5.5C or 5-(2'-aminoethyl)aminonaphthalene-1-sulfonic acid (EDANS), fluorescein, anthranilamide, coumarin, and terbium chelates.

Major regulatory elements include; (I) enhancers, (II) sites within chromatin loops that engage in intra- or interchromosomal contact in multigene complexes and (III) regulatory sites within chromatin loops that determine loop structure. Each of the different types of regulatory elements is expanded below.

Enhancer-Promoter Interactions (FIG. 1)

Enhancers are DNA elements that regulate the activity of specific gene promoters. Enhancers may be separated from the genes they regulate by large genomic distances. Enhancers are brought in close proximity to target genes by chromatin looping. Genome-wide chromatin interactome studies reveal that enhancer-promoter interactions are pervasive, and may occur in cis even over large genomic distances, or in trans across different chromosomes.

Enhancer-promoter interactions are the primary means in which cell-specific gene expression is achieved. Enhancers contain binding sites for transcription factors, chromatin remodelers and transcriptional co-activators. Enhancers with large numbers of regulatory protein binding sites (transcription factors, chromatin remodelers, co-activators), are termed "super-enhancers".

Super-enhancers have been shown to be more sensitive to small changes in factor concentration than those with small numbers of binding sites. Super-enhancer regulated genes may be identified by identifying genes located with the same TAD. Super-enhancer regulated genes have been shown to have important roles in embryonic stem cell identity. Super-enhancer regulated genes have been shown to be more highly expressed than genes regulated by typical enhancers.

A remarkable recent observation is the transcription of a novel class of non-coding RNAs, including enhancer RNA (eRNA), activating RNAs and long non coding RNAs (lncRNA), arising from enhancer loci throughout the genome, including the chemokine locus. eRNAs are enriched for H3K4me1 and H3K27Ac chromatin marks, whilst lncRNAs possess, H3K4me3 and H3K36me3 chromatin marks. Through their interaction with promoters, cohesin and the mediator protein complex, eRNAs have been proposed to regulate chromatin looping.

Recent studies have used a combination of predictive polymer modelling followed by imaging and deletion of structural DNA regulatory elements such as CTCF/cohesin in cells, to ascertain variation in the internal structure of TADs between single cells. These studies have revealed the fluctuating structural environment within a TAD and the tremendous heterogeneity in TAD configurations between single cells that could be linked to transcriptional activity. Though DNA regulatory elements are identical in all cells, eRNA activity is highly tissue specific. eRNAs are speculated to play key roles in organizing TAD structure, though this remains functionally uninterrogated.

A well-characterized example of enhancer-promoter interactions is the well-established model between the locus control region (LCR) and the promoter of the β-globin gene. These LCR-mediated chromosomal interactions have been shown to result in variability in β-globin genes transcript levels, or variegated gene expression, across the population (Noordermeer et al., 2011). In cells unable to form this enhancer-promoter loop, forceful tethering of Ldb1, a transcription factor thought to mediate the LCR-β-globin interaction, to the β-globin promoter showed that formation of the LCR-β-globin loop underlies transcriptional activation (Deng et al., 2012). Therefore, preventing enhancer-promoter interactions will have a significant impact on gene expression. To date, no assay exists to discretely perturb enhancer elements to silence gene expression.

Figure 2:
FIG. 2: Intra- or inter-chromosomal contact in multigene complexes. Looping brings distal genes into close proximity, enabling chromosomal contact in multigene complexes. In a comparable manner to enhancer-promoter interactions, specific chromatin interactions in multigene complexes are detected in a subject of cells within the population (Papantonis et al. (2010)). Loop-mediated contact between genes in a multigene complex, influences their transcriptional status of interacting genes. Therefore, preventing loop-mediated contact will have a significant impact on the gene expression of interacting genes in a multigene complex. To date, no assay exists to discretely perturb interacting genes in a multigene complex to silence expression.
Figure 2:

Regulatory Sites within Chromatin Loops that Determine Loop Structure (FIG. 2)

CTCF, a sequence-specific DNA-binding protein, binds to consensus sites (CS) that frequently flank genes. At CS sites, the multiprotein cohesin 'ring-like' complex (including the Smc1-Smc3 heterodimer, Rad21 and Scc3/SA1/SA2) is loaded onto chromatin by Nipbl. The mediator complex (a multiprotein complex composed of over 30 proteins) may also be recruited to CTCF and/or cohesin occupied chromatin to stabilize loop topology, and regulate transcription initiation and elongation.

Studies to identify the architectural proteins shaping the three dimensional genome have revealed CCTC-binding factor (CTCF), Mediator and cohesin to have widespread and specific roles across the genome. Consistent with the above-mentioned role in enhancer-promoter interactions, Mediator and cohesin were found to specifically bridge short-range, cell-type-distinct interactions. On the other hand, long-range interactions were found to be bridged by CTCF and cohesin. Boundaries of TADs are enriched in binding sites for CTCF and cohesin complex, implicating their importance in maintaining domain integrity and loop-mediated transcription. Experiments in cells containing a deletion that spans the boundary between the Xist and Tsix TADs in the X-chromosome inactivation center, directly demonstrated that the loss of boundary had led to the partial fusion of the adjacent TADs and the formation of new and ectopic contacts, causing long-range transcriptional misregulation (Dixon et al., 2012). Furthermore, depletion of CTCF and cohesin has revealed that these factors contribute differentially to domain organization and transcriptional regulation. Particularly, disruption of cohesin reduces local chromatin interactions although TADs remain intact, whereas depletion of CTCF leads to a reduction in local intradomain interactions but also to an increase in interdomain interactions. In each case, different classes of genes are misregulated, indicating that each factor has a distinct capacity in chromatin organization and gene regulation.

Knockout studies of these structural chromatin proteins (mediator, cohesin, CTCF) reveal their role in regulating transcription. However, the interpretation of these studies is complicated by the global alterations in gene expression that inevitably occurs. Preventing chromatin remodeling and structural proteins from binding to their target sites will have significant impact on gene expression of related genes. To date, no assay exists to discretely perturb sites where chromatin structural proteins bind, and monitor associated gene expression at a single cell level.

Figure 3:
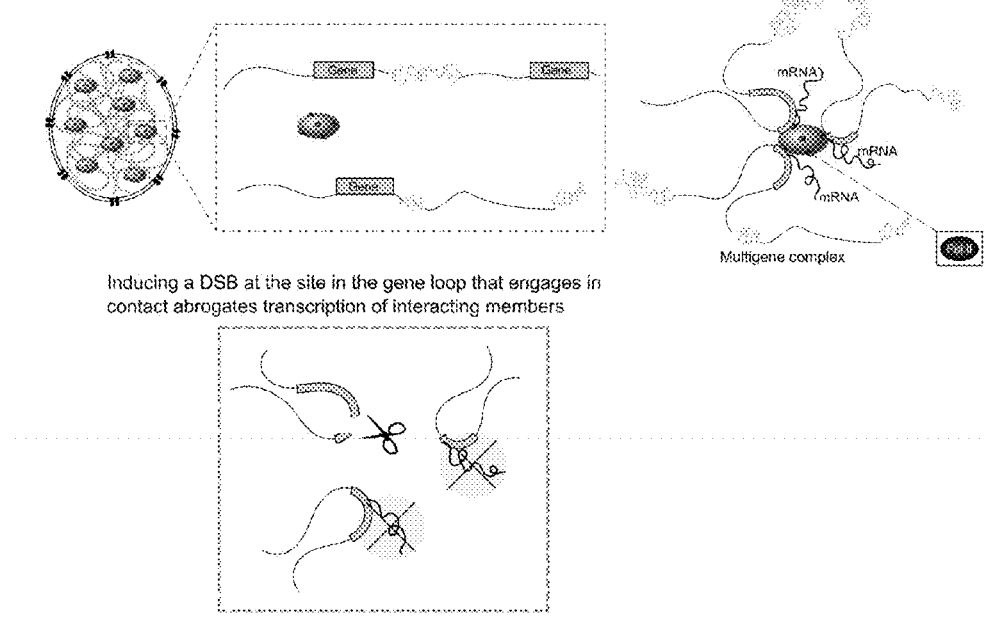
FIG. 3: Regulatory sites that determine loop structure. Many distinct regulatory elements have been identified that organize chromatin into loops, thereby altering gene expression. Knockout studies of these structural chromatin proteins reveal their role in regulating transcription. However, the interpretation of these studies is complicated by the global alterations in gene expression that inevitably occurs. Preventing chromating remodelling and structural proteins from binding to their target sites will have significant impact on gene expression of related genes. To date, no assay exists to discretely perturb sites where chromatin structural proteins bind, and monitor associated gene expression at a single cell level.

Intra- or Interchromosomal Contact in Multigene Complexes (FIG. 3)

Within a TAD, or at the interface between TADs, chromosomal looping may also bring co-regulated genes into close proximity to permit chromosomal contact. These interactions are proposed to occur at discrete foci of active, hyper-phosphorylated RNA Pol II that have been referred to as multigene complexes or transcription factories.

Sites within a chromatin or DNA loop which engage in intra-chromosomal or inter-chromosomal contact may include both coding and noncoding regions, including, but not limited to, introns, exons and 3' un-translated regions.

Numerous studies have demonstrated that loop-mediated contact between coregulated genes coincides with alterations in the transcription of interacting genes (Papantonis et al., 2010, Li et al., 2012). Over 95% of genes engaged in promoter-mediated chromosomal contact in multigene complexes are associated with transcriptional activity. Therefore, chromosomal contact between coregulated genes in multigene complexes appears to be a critical component of transcriptional regulation.

The present inventors developed a novel single cell microscopy-based assay, to directly address the role of loop-mediated contact on the transcription of interacting genes. Using this assay, they demonstrated that chromosomal contact plays a central role in supporting transcription of co-regulated genes. Therefore, preventing loop-mediated contact will have a significant impact on the gene expression of interacting genes in a multigene complex. This is the first assay described to date, that enables the discrete perturbation of interacting genes in a multigene complex to silence expression.

The present invention provides a means to enhance the study of cellular processes through the discrete perturbation of chromatin regulatory elements that are engaged in chromosomal contact.

The invention provides a means for the discrete perturbation of chromatin regulatory elements resulting in the abrogation of transcription that can be applied in translational medicine. For example through the precise delivery of the nuclease to the correct cell type and location. Or through the manipulation ex vivo of patient cells with the nuclease that are then autologously transplanted into the patient with the nuclease modification having been conducted in the patient cells.

The perturbation is induced by site-specific nucleases (including meganucleases, zinc fingers (ZF), transcription activator-like effectors (TALE), the Type II CRISPR system (clustered regularly interspaced short palindromic repeats, BUD nucleases) which are designed to induce a double strand break (DSB) within the regulatory site (Li et al., 2011).

Typically, these site-specific nucleases are used in 'cut and paste' experiments, whereby the cell's own repair responses, nonhomologous end-joining (NHEJ) or homologous recombination (HR), are exploited to repair the DSB. This is the first description of the use of these site-specific nucleases for the purpose of disrupting chromosomal contact.

Through the use of a catalytically inactive Cas9 coupled to a repressor domain, the CRISPRi system has been used as an efficient means to silence gene expression at a population level. However, the CRISPRi approach fails to reveal cell-to-cell variability. Further, as this approach only silences at the level of transcription, it is unable to perturb chromosomal interactions between regulatory elements.

Our results establish that the CRISPR system can be used as a modular and flexible DNA-binding platform for the recruitment of proteins to a target DNA sequence, revealing the potential of CRISPRi as a general tool for the precise regulation of gene expression in eukaryotic cells. Site-specific nucleases are delivered into live cells by transfection (including microporation, electroporation, lipid transfection, calcium phosphate transfection) and endogenously expressed.

Cells for use for the assay encompass any type of eukaryotic cell, including but not limited to primary and induced pluripotent stem cell lines.

The DSB, or site of disruption, is detected at a single cell level by immunofluorescent staining of a factor of the DSB repair process.

The disruption caused by the DSB may serve to do one of the following: (I) A large number of other proteins involved in the repair process are recruited to the DSB site. Therefore, one possibility could be that chromosomal contacts between genes or gene elements may still occur, but are "bridged" via the repair complex. This may occlude the ability of gene loops to "deliver" Pol II to other interacting genes. (II) DSB induction has been shown to enhance the mobility of damaged chromatin. Therefore, due to increased movement, the probability that the disrupted gene loop will be able to interact with other loci is significantly reduced. (III) Alternatively, it is unknown how the DSB, and associated repair factors, influence gene topology. Therefore, the DSB may prevent loop-mediated contact by destabilizing or collapsing the gene loop.

In parallel to the detection of the DSB by immunofluorescent staining of a factor of the DSB repair process, transcriptional activity of: (i) genes of interest, or (ii) interacting genes in the multigene complex, are detected using intronic single molecule RNA fluorescent in situ hybridization (smFISH). As introns are typically excised and degraded co-transcriptionally, intronic FISH foci represent the transcriptional start site (TSS).

The following examples are offered by way of illustration and not by way of limitation.

EXAMPLE 1

Cell Culture

Early passage HUVECs from pooled donors (Lonza) were grown to ~80% confluence in Endothelial Basal Medium-2 (EGM-2) with supplements (Lonza), serum-starved (18 hr) in EGM-2+0.5% FBS, and treated with TNFα (10 ng/ml; Sigma) for up to 30 mins. Prior to transfection cells were grown in antibiotic free EGM-2.

TALEN Design

Software developed by the Bogdanove laboratory was used to identify TALEN candidate binding sites (Doyle et al., 2012). Left and right TALENs were designed to contain 18 full monomer repeats, which target a 20 bp sequence, where the first and last bases are specified by the thymine at the N terminus, and the 0.5 repeat, respectively. To facilitate FokI dimerization, the left and right TALEN target sites were chosen with a spacer of 16-19 bp. For the pDT TALEN vector, the SAMD4A left and right arms were cloned into the pBI_CMV1 bidirectional promoter vector (Clontech). The left TALEN was cloned into MCS1 of pBI_CMV1 (Mlu1 and HindIII) and the right TALEN was cloned into MCS2 of pBI_CMV1 (EcoRI and BglII).

TALEN Binding Sites and Spacer Regions

The SAMD4A TALEN recognition sequences (for both pcDNA and pDT vectors) are: left TALEN 5'-TCC ACG TTT ATA AAT AGC TG-3' (SEQ ID NO:1) and right TALEN 5'-CAC TGG GGT GTG GAA GCA TA-3' (SEQ ID NO:2), with a 16 bp spacer. The TNFAIP2 TALEN recognition sequences are: left TALEN 5'-TTC GCG GCC CAC CTG GCC GC-3' (SEQ ID NO:3) and right TALEN 5'-CTG TGC GAG CGC GAC ACC TA-3' (SEQ ID NO:4), with a 16 bp spacer. The SLC6A5 TALEN recognition sequences are: left TALEN 5'-TTG TCC CTT TAA AAC TTG AA-3' (SEQ ID NO:5) and right TALEN 5'-TTA TCA AAC TTG TAT TAT CA-3' (SEQ ID NO:6), with a 17 bp spacer. The BMP4 TALEN recognition sequences are: left TALEN 5'-TGC AGC GCC ACA GTC CCC GG-3' (SEQ ID NO:7) and right TALEN 5'-CAA CCG TTC AGA GGT CCC CAG-3' (SEQ ID NO:8), with a 19 bp spacer.

TALEN Synthesis

TALENs were generated using the protocol by Sanjana et al. 2012. Briefly, specific primers were used to amplify monomers from each of four plasmids to add the appropriate adapters (each plasmid corresponding to one RVD; NI=A, HD=C, NG=T and NN=A/G). Monomers generated by PCR were then purified by gel extraction and DNA concentration was normalized to create a monomer library. In the first Golden Gate reaction step, monomers were simultaneously digested with the type IIS restriction enzyme BsmBI and ligated to generate circularized hexamers. Non-hexamers were removed by exonuclease treatment. Hexamers were then amplified by PCR, gel purified and the DNA concentration between samples was normalized using the Qubit High Sensitivity DNA quantification kit (Life Technologies). In the second Golden Gate step, hexamers were simultaneously digested with BsaI, and ligated into the appropriate TALEN cloning backbone (corresponding to one of the four different bases targeted by the 0.5 repeat) to generate the final TALEN expression construct. Colony PCR was used on $E.\ coli$ transformants to identify successful TALEN clones. HUVECs were then microporated with the respective TALENs using the Neon® Transfection System (Life Technologies) according to manufacturers instructions. Nuclease activity was assessed by the surveyor assay and the consistent co-localization of DNA FISH with double strand breaks, as assessed by H2A.X immunofluorescence (Keogh et al., 2005).

Surveyor Assay

Genomic DNA of transfected cells was extracted using QuickExtract DNA extraction solution (Epicenter). The genomic region encompassing the nuclease target sites in human SAMD4A, TNFAIP2, SLC6A5 or BMP4 were PCR amplified and amplicons cleaned up with QIAquick PCR Purification Kit (Qiagen). For SAMD4A the primers were 5'-TGA GGG AGA TTC CAT TGA GC-3' (SEQ ID NO:9) and 5'-GGA AAA AGT GCT GCT CCA AC-3' (SEQ ID NO:10). For TNFAIP2 the primers were 5'-TGC AGG ACA GAC TCA GGA CA-3' (SEQ ID NO:11) and 5'-ATT TGG GTT GAG CAT TCC AC-3' (SEQ ID NO:12). For SLC6A5 the primers were 5'-TGA TTT AAC CCC CTC CTT CC-3' (SEQ ID NO:13) and 5'-CTT TAG GAG CCA CAG CCA AC-3' (SEQ ID NO:14). For BMP4 the primers were 5'-CTA GTA CCT CCG CAC GTG GT-3' (SEQ ID NO:15) and 5'-TCC AGC ACC ACT ATT GGA AA-3' (SEQ ID NO:16). The DNA fragments were then subjected to digestion with mismatch-sensitive T7 endonuclease I (T7E1; New England BioLabs). For the T7E1 assay, DNA was denatured at 95° C. for 5 min, slowly cooled down to room temperature to allow for formation of heteroduplex DNA, treated with 5 U of T7E1 for 1 hr min at 37° C., and then analyzed by 1.2% agarose gel electrophoresis.

RNA FISH Probes

RNA FISH was performed according to the protocol by Raj et al. 2008 using 48 20-mer probes (Biosearch) targeting the following genes: SAMD4A (probes set i=~1.5 kbp into intron 1, probe set ii=~34 kbp into intron 1, TNFAIP2 (intron2), SLC6A5 (intron1), RCOR1 (intron1) and 32 20-mer probes targeting eGFP (Table 1). Each 20-mer bares a 3'-amino-modifier C6-dT. The amino group was subsequently conjugated to the following NHS-ester dyes: ATTO-488, ATTO-565, ATTO-647N (ATTO-TEC) or Alexa Fluor 647 (Invitrogen). Briefly, oligonucleotide probes were ethanol precipitated and resuspended in 0.1 M sodium tetraborate (Sigma). Approximately 0.3 mg of the NHS-ester dye (ATTO-TEC) was dissolved in dimethyl sulphoxide (Sigma). The dye solution was added to the probe solution and incubated overnight in the dark at 37° C. Following conjugation reaction, the probes were ethanol precipitated overnight, and resuspended in 0.1 M Triethyl ammonium (TEA, Sigma). Conjugated probes were separated and purified to enrich for dye-conjugated probes by reverse phase HPLC on a C18 column.

TABLE 1

Sequences of RNA FISH probes

| Probe Sequence (5'-3') | Sequence Identity Number |
|---|---|
| SAMD4A 1.5 kbp into intron 1 | |
| ATTCATGCTACCGTAGCTAC | SEQ ID NO: 25 |
| GGAAACTGCATGAGAGAAAA | SEQ ID NO: 26 |
| GACCTGACTTACTTATTTCC | SEQ ID NO: 27 |
| CCAGAAAATCCAGACTCTAC | SEQ ID NO: 28 |
| GGAGGAAGGAAAAAACACAC | SEQ ID NO: 29 |
| AGCCACGTTGCCCAAAAGAA | SEQ ID NO: 30 |
| CATGTGTTGCTGAAATCCAG | SEQ ID NO: 31 |
| ATCCAAGCTTGGCTTCTGAA | SEQ ID NO: 32 |
| TTCATGTACTCCTCACACAG | SEQ ID NO: 33 |
| CCAGAATATCTGTGGGAAA | SEQ ID NO: 34 |
| TTCTGAAGACGAAGCTCTAA | SEQ ID NO: 35 |
| TTACTAGTCTCTAGCGTCAC | SEQ ID NO: 36 |
| GCAGTAAGCTTAACCGCATT | SEQ ID NO: 37 |
| CAAGATCCGTATCAATATGG | SEQ ID NO: 38 |
| CCTTTCTCCAAGACCCTTTT | SEQ ID NO: 39 |
| AAGTAACCCACTTCATGCCT | SEQ ID NO: 40 |
| GCAGGGTAATATGAAACGAT | SEQ ID NO: 41 |
| CATACTAGTTGAGGTGTCTG | SEQ ID NO: 42 |
| GCTGGACCTTTCGACTATAT | SEQ ID NO: 43 |
| CCACGCTAGCAAATAGGAAA | SEQ ID NO: 44 |
| CCTACCCTCCAGGATATAAT | SEQ ID NO: 45 |
| TCACAACCATCAGACTTTCC | SEQ ID NO: 46 |
| GCAGCAGCATGAACTAAAGA | SEQ ID NO: 47 |
| TAAACACTGGGGACTCTGTT | SEQ ID NO: 48 |
| ACCCTGCATTCTTTTCTCTG | SEQ ID NO: 49 |
| AACATGGAACAGCTGGAAGA | SEQ ID NO: 50 |
| ACCTTGTCATCAAATGGCAG | SEQ ID NO: 51 |
| ACTCACTTTAGTGTCTCCCA | SEQ ID NO: 52 |
| TCGCTTCTTGCTGCTCTGAA | SEQ ID NO: 53 |
| ATACTAGGGAGGAGGAATGA | SEQ ID NO: 54 |
| TGTTTTCACCATCGTGCACA | SEQ ID NO: 55 |
| ATATGGAAGCATCCCATTCT | SEQ ID NO: 56 |
| CACTTCCACCCTATGATTCT | SEQ ID NO: 57 |
| AACTGTGAAGATTTCCAGCG | SEQ ID NO: 58 |

TABLE 1-continued

Sequences of RNA FISH probes

| Probe Sequence (5'-3') | Sequence Identity Number |
|---|---|
| AGTCCTGTCTGGTCAGGAAA | SEQ ID NO: 59 |
| TTGGCCATGCAGGATCTTTC | SEQ ID NO: 60 |
| ATGGAATCTCCCTCAATGTG | SEQ ID NO: 61 |
| AAACGTGGAGCTCAACCAAA | SEQ ID NO: 62 |
| AATTATGCTTCCACACCCCA | SEQ ID NO: 63 |
| AGAGGGTGGATCATCAGTTA | SEQ ID NO: 64 |
| CCGCTGAAATTAAGGAAGGA | SEQ ID NO: 65 |
| AAAACCGAGCAGGTAAACCA | SEQ ID NO: 66 |
| CCTTGTTTGTCAAACCTGAG | SEQ ID NO: 67 |
| GCGTAAATCCTCTGCAATCT | SEQ ID NO: 68 |
| CCAGCACTGAAATCAAGCAT | SEQ ID NO: 69 |
| AGATGAGTTTGAACAGTCCC | SEQ ID NO: 70 |
| GTGCTGCTCCAACATTTGAA | SEQ ID NO: 71 |
| CTCCATTACTCAAAGGGAAA | SEQ ID NO: 72 |
| SAMD4A 34 kbp into intron 1 | |
| CCCCACCCAATATGAATGAA | SEQ ID NO: 73 |
| CTGTTGAGACTCATTCTTGT | SEQ ID NO: 74 |
| GCTTTAAAATGTCGCTGGGT | SEQ ID NO: 75 |
| GTGATGGCCCTTTGATTTAC | SEQ ID NO: 76 |
| TAATCCTGCCATTCCTAAGC | SEQ ID NO: 77 |
| CCACTGTTTAACCGCAACAA | SEQ ID NO: 78 |
| AATTCCAACATTGGAGCCTC | SEQ ID NO: 79 |
| CACACAGACACAAGATTCAA | SEQ ID NO: 80 |
| GGTTTCTGCCTAAAACAGCA | SEQ ID NO: 81 |
| ATTCTCTCCAAGTCATCAGC | SEQ ID NO: 82 |
| TAAGAGTGTCTGAGGGGTTA | SEQ ID NO: 83 |
| GTCTAGCCAGACTGTAGTTT | SEQ ID NO: 84 |
| CTCACCCCAAAGTCTTTAAG | SEQ ID NO: 85 |
| TCTAAGGACTTAGCACCATC | SEQ ID NO: 86 |
| GCCTTCGGAGTTTTCTTCTT | SEQ ID NO: 87 |
| TTTCTCTCCAACATGGTTGC | SEQ ID NO: 88 |
| GTTTCTACATTGCTTCCCTC | SEQ ID NO: 89 |
| TTTCTGTCCTGCTTTCTCCT | SEQ ID NO: 90 |
| AAAGAAGTCTCTGGTACCAG | SEQ ID NO: 91 |
| GTCTAGCCCAAGTGAGAGAA | SEQ ID NO: 92 |
| TAAACCAGAAGCCTGTCTCT | SEQ ID NO: 93 |
| ATCTAATCCATGGCCAGCCA | SEQ ID NO: 94 |

TABLE 1-continued

Sequences of RNA FISH probes

| Probe Sequence (5'-3') | Sequence Identity Number |
|---|---|
| AAAGGGCATTGATTCCACAG | SEQ ID NO: 95 |
| ACTTGGAAAGATGTCCCAAG | SEQ ID NO: 96 |
| CCCAGTTAATCCTAAGGAAA | SEQ ID NO: 97 |
| GCTTCTTCTTTGTACAGTGA | SEQ ID NO: 98 |
| CAGTCCTCTAGCAATGGAAA | SEQ ID NO: 99 |
| GTGTGTGTGTGTGTGTGTAT | SEQ ID NO: 100 |
| TTTCGTGTGTGTGTGTGTGT | SEQ ID NO: 101 |
| AAAGCCACTGTCTGTGCTAT | SEQ ID NO: 102 |
| AAAGGAAGTATCTTCATCCC | SEQ ID NO: 103 |
| CAGAAGAGACTAGAACAGAC | SEQ ID NO: 104 |
| ACTAGTTTCTGTTCCACGCA | SEQ ID NO: 105 |
| CTTCATCTCCTTAAGCTAGC | SEQ ID NO: 106 |
| CATGTCATTCCCACAAGAAC | SEQ ID NO: 107 |
| TGAGAAGGTTTCTGTCCATG | SEQ ID NO: 108 |
| AAAGCTTCCCAATTCTAGCC | SEQ ID NO: 109 |
| CCGAAGGTGAATGTCTTAAG | SEQ ID NO: 110 |
| ATCTCCTAATGCTATCCCTC | SEQ ID NO: 111 |
| CTGCACCCATTAACTCATCA | SEQ ID NO: 112 |
| TATACATGTGCCGTGTTGGT | SEQ ID NO: 113 |
| CAACGTGCAGGTTTGTTACA | SEQ ID NO: 114 |
| GAGAGAATGTAAGAAGGCGA | SEQ ID NO: 115 |
| TTTAGCCTGACAGGCATGAA | SEQ ID NO: 116 |
| GTGCACTTGAAGTAACAAGG | SEQ ID NO: 117 |
| TGATGTCCTTGATACTGGTC | SEQ ID NO: 118 |
| GCTGCATTTCCAAGAAGATC | SEQ ID NO: 119 |
| ATTCAGTAGGTCTGCAGTGT | SEQ ID NO: 120 |

TNFAIP2 intron 2

| TACCTGCCCTATCACCCCTC | SEQ ID NO: 121 |
| ACCTTCCTCTCACCTTCTCC | SEQ ID NO: 122 |
| AGAGGACATGCTCAGGAGCA | SEQ ID NO: 123 |
| TAGCTCTGCTCAGCTCCAGA | SEQ ID NO: 124 |
| ATCACTTGGAACTCTCCTGC | SEQ ID NO: 125 |
| TAACAAGACACGTGGCCCTA | SEQ ID NO: 126 |
| ACAGGGTAACCCTACACAAT | SEQ ID NO: 127 |
| TGTACTCAGCAGGGGTACCA | SEQ ID NO: 128 |
| ATCTATGGAGTCAAGGGACG | SEQ ID NO: 129 |
| ATGCAGACCGTGCGAATGAC | SEQ ID NO: 130 |

TABLE 1-continued

Sequences of RNA FISH probes

| Probe Sequence (5'-3') | Sequence Identity Number |
|---|---|
| ACACTGCAGTAAGCCTCTCT | SEQ ID NO: 131 |
| ACAATAACAGCCCCTGGACT | SEQ ID NO: 132 |
| TTCACACTAGGATCTGGGGC | SEQ ID NO: 133 |
| CTCCAGGCTTCCTTCCTAAA | SEQ ID NO: 134 |
| ACACTGCCCACACTGTCTAT | SEQ ID NO: 135 |
| TTCAACACGAACTGAGCCCA | SEQ ID NO: 136 |
| ATCCTTCTGCCAGAGGCTGA | SEQ ID NO: 137 |
| CTCTCCACTGGACCCTTTCT | SEQ ID NO: 138 |
| TATGCCCTGCTGACTCCTCT | SEQ ID NO: 139 |
| TTATCTCTCCCGTGGCCCCT | SEQ ID NO: 140 |
| AGCAAGCGGGAACTGGCTCT | SEQ ID NO: 141 |
| CATTTCCTGGTGAGTCAGGA | SEQ ID NO: 142 |
| TCACTGGGACAGAAAGACTG | SEQ ID NO: 143 |
| TTGCCTGTTGCTAACCCCAG | SEQ ID NO: 144 |
| TCCATGCCCAGCTTGGCTTT | SEQ ID NO: 145 |
| ACACAGGCTTCAACGATGCC | SEQ ID NO: 146 |
| CTCCGTTCCCACATTTCTG | SEQ ID NO: 147 |
| CAATCCAGATGCAGCTGTGT | SEQ ID NO: 148 |
| AAATGACCTTCTCTCTGCCC | SEQ ID NO: 149 |
| CTTTGTCTGCCTAGAGGTTT | SEQ ID NO: 150 |
| AGCCCTGGCACTTCCTAAGG | SEQ ID NO: 151 |
| ATCTTGGCTCACTGTCCTGG | SEQ ID NO: 152 |
| CCCCAAACTGCTCCACAGAC | SEQ ID NO: 153 |
| TAGGCCAGAATGGGCAGGAA | SEQ ID NO: 154 |
| AGGTCTTGGGCATCTCACCA | SEQ ID NO: 155 |
| ACTCACAGCAGCCCTGGAAT | SEQ ID NO: 156 |
| TGTCACCCAGATAAAACCCT | SEQ ID NO: 157 |
| TTCTTCCTGCTCCAAGACTA | SEQ ID NO: 158 |
| GAGCCACCTTTAAGATCTGA | SEQ ID NO: 159 |
| AATTCCTTCTTCACCCAGCA | SEQ ID NO: 160 |
| TGCTCCTTCCCTCACCTCCA | SEQ ID NO: 161 |
| TCACTGCAAAAGCCTCCTCC | SEQ ID NO: 162 |
| AAATCAGCAGCCTCATGCCA | SEQ ID NO: 163 |
| TAGGTCCTGCTCCAAAATAG | SEQ ID NO: 164 |
| ATCATGCCTCCTCTGACTCT | SEQ ID NO: 165 |
| TTGGAACAGAAACTCTGAAG | SEQ ID NO: 166 |

TABLE 1-continued

Sequences of RNA FISH probes

| Probe Sequence (5'-3') | Sequence Identity Number |
|---|---|
| TCCTCCATCTACTTAGTTTG | SEQ ID NO: 167 |
| GGTCCCCATTTCAGATGATG | SEQ ID NO: 168 |

SLC6A5 intron 1

| Probe Sequence (5'-3') | Sequence Identity Number |
|---|---|
| CCCTTTCCTCTTGAAAGAAC | SEQ ID NO: 169 |
| AACGAATCTGCTTTCCCTGT | SEQ ID NO: 170 |
| GCACAGACATCTCCAAAAGA | SEQ ID NO: 171 |
| AGAATTGTTCTCCTCGTCGC | SEQ ID NO: 172 |
| AGTACAAATACCTAGGGCTG | SEQ ID NO: 173 |
| ACAGCCTAGGAAACCTCTTT | SEQ ID NO: 174 |
| TCTTTAGGAGCCACAGCCAA | SEQ ID NO: 175 |
| TTTTCAGCACCGAGGACAGT | SEQ ID NO: 176 |
| AGAGCAACTCGCCTCTGTAC | SEQ ID NO: 177 |
| TTTGTCTCAGTAGCCTCTAG | SEQ ID NO: 178 |
| AAATCTAGGTACCTCGGCTT | SEQ ID NO: 179 |
| GCAGAATAGAACTCCTCGAT | SEQ ID NO: 180 |
| TCTAACCCCTTTCACAAAC | SEQ ID NO: 181 |
| TCCTATTATCTTCGCCTCCA | SEQ ID NO: 182 |
| GCTTCCTAAACATTAGCACC | SEQ ID NO: 183 |
| TCCCCTCGTGTTATCTTTCA | SEQ ID NO: 184 |
| CGGTGGTTTTTCTATCCACT | SEQ ID NO: 185 |
| CGCTTTTTCCCAATTCACTT | SEQ ID NO: 186 |
| GAGTACCAAAACTCATGACT | SEQ ID NO: 187 |
| CTTCACAACTCTAAGCTTGC | SEQ ID NO: 188 |
| CGTAACTATTCACAGGAGTC | SEQ ID NO: 189 |
| CTTCTTCTTCCTCTTCTTCT | SEQ ID NO: 190 |
| TCTTCTTCTTCTTCTTCTTC | SEQ ID NO: 191 |
| CTTCTTCTTCTTCTTCTTCT | SEQ ID NO: 192 |
| GGTCTTCTTCTTCTTCTTCT | SEQ ID NO: 193 |
| CCCAGACATGGAAAAGAATA | SEQ ID NO: 194 |
| CAACTCGTATTCACTTCCAG | SEQ ID NO: 195 |
| GACACAGAGTAGTAACTAGA | SEQ ID NO: 196 |
| CCACAAAAAACCTACAACG | SEQ ID NO: 197 |
| CAGGTAGCAAAGACAAGGTT | SEQ ID NO: 198 |
| TGAGGCAAATTGGTTGAGT | SEQ ID NO: 199 |
| ACAAAGCTGATGCCCTGGCA | SEQ ID NO: 200 |
| TTTTCCCCCATAGACAAGCT | SEQ ID NO: 201 |
| CATTCAACAATGCACACTGC | SEQ ID NO: 202 |
| TTTTCCGCCCCATTTCCTTT | SEQ ID NO: 203 |
| CCATCACCACTGTAGAAAGA | SEQ ID NO: 204 |
| TTGGATTCCACATCACAGCT | SEQ ID NO: 205 |
| AAATAGCCCTGGAGTCATGA | SEQ ID NO: 206 |
| TGTAAGGGTAAAGGGGGAAT | SEQ ID NO: 207 |
| GGATGAACTAAGAAAAGAGG | SEQ ID NO: 208 |
| CTAATATTCCCTCCCTAGTG | SEQ ID NO: 209 |
| CCCGTTTCATCAATAACCAG | SEQ ID NO: 210 |
| GGCTGCAATCAGTATTTCTC | SEQ ID NO: 211 |
| GGGAAGCAAATTGGAATCTG | SEQ ID NO: 212 |
| TCAGGTCCAGACACAATATC | SEQ ID NO: 213 |
| TAGATATGGAGACGTTCGCA | SEQ ID NO: 214 |
| CAAAACAAAGTCACAACAGC | SEQ ID NO: 215 |
| CAAACACAATGTCAAGTTCG | SEQ ID NO: 216 |

RCOR1 intron1

| Probe Sequence (5'-3') | Sequence Identity Number |
|---|---|
| CAAAAAGAAAGTTGTCGGCG | SEQ ID NO: 217 |
| GTTTGCAGAACACTCGTGTG | SEQ ID NO: 218 |
| GCTCACCTGGACGCAGGGAC | SEQ ID NO: 219 |
| GCAGGACACTAACTCTCCGG | SEQ ID NO: 220 |
| GGACCTCCTAAGTCCGGGGC | SEQ ID NO: 221 |
| GTTCCGAGAAAGGGGTCTCT | SEQ ID NO: 222 |
| CAGTCAGGAGCCAGCAAGAG | SEQ ID NO: 223 |
| GTTCTTCTACTCGCCTTCTG | SEQ ID NO: 224 |
| AGGTCCTAAAATCCAACTGC | SEQ ID NO: 225 |
| GGCTAAAGCTTCTGATGCTT | SEQ ID NO: 226 |
| CTAGGGTGTAGGGCTTTCTT | SEQ ID NO: 227 |
| CCAGGGAACTAAGTGTTCCA | SEQ ID NO: 228 |
| TTGCTTCTACACAGAATAGC | SEQ ID NO: 229 |
| TGACGAATTCCTTTGTCTGA | SEQ ID NO: 230 |
| TGGCTAGAATCTCATGCATT | SEQ ID NO: 231 |
| AAAGACAGTCTCATACAGAC | SEQ ID NO: 232 |
| CTCCAGCTTTACAAGATGCT | SEQ ID NO: 233 |
| TCCAACCATGGAGGATTGTT | SEQ ID NO: 234 |
| TGGTATAACCCACATACAGA | SEQ ID NO: 235 |
| TTTCCAAGGAAAAACATGT | SEQ ID NO: 236 |
| ATTGCAATTTTCTGCAGTCT | SEQ ID NO: 237 |
| CGCCTTTTTCAAGGACTAGA | SEQ ID NO: 238 |

TABLE 1-continued

Sequences of RNA FISH probes

| Probe Sequence (5'-3') | Sequence Identity Number |
|---|---|
| TTAATAACAGCTTGAGAGCA | SEQ ID NO: 239 |
| CTTCAAAGTGCAGTTTAGTA | SEQ ID NO: 240 |
| GTCCAAGAGCTCACCTAGGA | SEQ ID NO: 241 |
| AGGAAGTCATTTATTTCCAG | SEQ ID NO: 242 |
| TCAAAATTTAGAAGGCCAAT | SEQ ID NO: 243 |
| AAGAAACACAAACGCGAGTA | SEQ ID NO: 244 |
| AGAGGAAACTATCAAAAACA | SEQ ID NO: 245 |
| CCTGTCACTCATAAACGAGA | SEQ ID NO: 246 |
| ATAGCCTGGCCACCTAGTTC | SEQ ID NO: 247 |
| AGGAGCCAAGCATACAAGAG | SEQ ID NO: 248 |
| CTGGTGGCCAACCAAGGAAC | SEQ ID NO: 249 |
| GTAACCAAAAAACAGTATGC | SEQ ID NO: 250 |
| CAAAATGAAGACAGGGTCAA | SEQ ID NO: 251 |
| AAGCAAAGATAGACTTGACC | SEQ ID NO: 252 |
| ACAAGCTTTATGTTCTGTGT | SEQ ID NO: 253 |
| CTCAAAGATTTGTGGAAGTC | SEQ ID NO: 254 |
| TGTTGTTGACAAATATGCCC | SEQ ID NO: 255 |
| TCGATGAATGTCAGAAATCT | SEQ ID NO: 256 |
| AATGCAGAGCTGATGTCAAT | SEQ ID NO: 257 |
| GTATAACTCCAAAGAAGTCA | SEQ ID NO: 258 |
| AACAAAAAGCCCAAAGACAG | SEQ ID NO: 259 |
| GCTGGTCACTAGCAAGTTTA | SEQ ID NO: 260 |
| GACTATGCAGCAAAACAGTT | SEQ ID NO: 261 |
| ATACTCAACCAATTGGCAGC | SEQ ID NO: 262 |
| GCTTAGGTTGGCAAAACAAG | SEQ ID NO: 263 |
| GTAAAGTCTCAATTTTCTGC | SEQ ID NO: 264 | eGFP

| Probe Sequence (5'-3') | Sequence Identity Number |
|---|---|
| TCCTCGCCCTTGCTCACCAT | SEQ ID NO: 265 |
| ATGGGCACCACCCCGGTGAA | SEQ ID NO: 266 |
| TTACGTCGCCGTCCAGCTCG | SEQ ID NO: 267 |
| GACACGCTGAACTTGTGGCC | SEQ ID NO: 268 |
| GGCATCGCCCTCGCCCTCGC | SEQ ID NO: 269 |
| TCAGGGTCAGCTTGCCGTAG | SEQ ID NO: 270 |
| TTGCCGGTGGTGCAGATGAA | SEQ ID NO: 271 |
| GGTGGGCCAGGGCACGGGCA | SEQ ID NO: 272 |
| CGTAGGTGAAGGTGGTCACG | SEQ ID NO: 273 |
| TAGCGGCTGAAGCACTGCAC | SEQ ID NO: 274 |

TABLE 1-continued

Sequences of RNA FISH probes

| Probe Sequence (5'-3') | Sequence Identity Number |
|---|---|
| GTGCTGCTTCATGTGGTCGG | SEQ ID NO: 275 |
| GCATGGCGGACTTGAAGAAG | SEQ ID NO: 276 |
| CGCTCCTGGACGTAGCCTTC | SEQ ID NO: 277 |
| GTCGTCCTTGAAGAAGATGG | SEQ ID NO: 278 |
| CGGCGCGGGTCTTGTAGTTG | SEQ ID NO: 279 |
| GTGTCGCCCTCGAACTTCAC | SEQ ID NO: 280 |
| TTCAGCTCGATGCGGTTCAC | SEQ ID NO: 281 |
| CGTCCTCCTTGAAGTCGATG | SEQ ID NO: 282 |
| AGCTTGTGCCCCAGGATGTT | SEQ ID NO: 283 |
| GTGGCTGTTGTAGTTGTACT | SEQ ID NO: 284 |
| TGTCGGCCATGATATAGACG | SEQ ID NO: 285 |
| ACCTTGATGCCGTTCTTCTG | SEQ ID NO: 286 |
| TGTTGTGGCGGATCTTGAAG | SEQ ID NO: 287 |
| AGCTGCACGCTGCCGTCCTC | SEQ ID NO: 288 |
| TGTTCTGCTGGTAGTGGTCG | SEQ ID NO: 289 |
| CACGGGGCCGTCGCCGATGG | SEQ ID NO: 290 |
| CTCAGGTAGTGGTTGTCGGG | SEQ ID NO: 291 |
| CTTTGCTCAGGGCGGACTGG | SEQ ID NO: 292 |
| TGATCGCGCTTCTCGTTGGG | SEQ ID NO: 293 |
| CACGAACTCCAGCAGGACCA | SEQ ID NO: 294 |
| CGAGAGTGATCCCGGCGGCG | SEQ ID NO: 295 |
| CACTTGTACAGCTCGTCCAT | SEQ ID NO: 296 |

Immuno-RNA RNA FISH

For each experiment, early passage HUVECs on coverslips were grown to ~80% confluence, treated with TNFα, fixed in 3.7% formaldehyde for 10 min at room temperature, then washed three times in PBS. Cells were permeabilized in ice-cold 90% methanol for ten minutes, then washed twice with PBS and incubated in blocking buffer (1% BSA/PBS) for 30 minutes at room temperature on an orbital shaker. Cells were then incubated in 1° antibody solution (diluted in 1% BSA/PBS) for 1 hr. Double strand breaks were detected with rabbit polyclonal anti-phospho-histone H2A/X (Ser139) (Sigma). Goat polyclonal anti-SAMD4A C-15 (SantaCruz), mouse monoclonal anti-TNFAIP2 F-6 (SantaCruz) and goat polyclonal anti-SLC6A5/GLYT2 N-20 (SantaCruz) were used to detect SAMD4A, TNFAIP2 and SLC6A5 proteins respectively. Coverslips were then washed 5 times with wash buffer (0.05% Tween-20/PBS), following incubation with secondary antibodies conjugated to either Atto-488 or Atto-565 for 1 hr. Coverslips were then washed 5 times with wash buffer (0.05% Tween-20/PBS), and post-fixed with 3.7% formaldehyde/PBS for 10 minutes at room temperature, followed by further permeabilization in 70% ethanol overnight. For RNA FISH detection, coverslips were washed twice in PBS and incubated in wash buffer (10% formamide, 2×SCC-1×SCC is 0.15 M NaCl plus 0.015 M sodium citrate) for 5 min. Cells were then hybridized overnight in a humidified chamber at 37° C. in 50 μl of Hyb buffer (10% dextran sulfate, 1 μg/μl E. coli tRNA, 2 mM Vanadyl ribonucleoside complex, 0.02% RNAse-free BSA, 10% formamide) combined with 50 ng of single molecule FISH probes. Coverslips were then washed 3× (30 min each on the orbital shaker) in wash buffer (10% formamide, 2×SCC). Cells were then incubated in equilibration buffer (0.4% glucose, 2×SCC) for 5 min and counter stained with 1 μg/ml DAPI (4',6-diamidino-2-phenylindole; Life Technologies). Coverslips were mounted in glox buffer (3.7 μg/μl glucose oxidase, 1 U catalase) and imaged.

Image Acquisition and Processing

Cells were imaged on a custom built Nikon Ti Eclipse widefield TIRF microscope using a 100×N.A. 1.49 Nikon Apochromat TIRF oil immersion objective. Imaging was done using mercury lamp illumination through the appropriate filter sets at low camera gain in each of the fluorescent channels using an Andor iXion897 EMCCD camera cooled to −80° C. The microscope was controlled using μmanager open source microscope management software (NIH and UCSF, USA). A 20 ms exposure time was used for DAPI. Exposure times ranged from 200 to 500 ms for other dyes. Each field of view was captured as a series of images acquired on multiple focal planes through the samples, across a range of 2-10 μm in the axial plane. A 0.2 μm piezo step-size was used for these z-stacks. Chromatic aberration was verified before image capture by alignment of Focal Check Fluorescent Microspheres (Molecular Probes). Signal intensities were measured using Fiji. The contrast of pictures shown was adjusted to fit a 16 bit grey scale. To facilitate the comparison between different fields of view on the same coverslip, IDV values were normalized relative to the intensity of fluorescent beads.

DNA FISH Probes

DNA FISH probes were constructed using either one of two methods. In the first method, they were constructed from BAC clones RP11-299D5 (SAMD4A), RP11-1102D6 (TNFAIP2) and RP11-207A15 (SLC6A5) (Empire Genomics). Using the FISH Tag DNA Multicolor Kit (Molecular Probes), these clones were nicktranslated to incorporate aminoallyl-dUTP, followed by dye-labeling of the aminemodified DNA. Alexa Fluor 488, 555 or 647 dye was incorporated. Alternatively, a PCR-based protocol was followed to construct "high definition" FISH probes (Sienko et al., 2012). Each locus was amplified from genomic DNA using twenty pairs of PCR primers obtained from the van Oudenaarden FISH probe database (Table 2). Amplified DNA was pooled, purified and labeled with a fluorescent dye (FISHBright 495, 550 or 647) using the FISHBright Nucleic Acid Labeling Kit (Kreatech).

TABLE 2

Sequences of PCR primers used to construct "high definition" FISH probes

| Primer Name | Primer Sequence (5'-3') | Sequence Identity Number |
|---|---|---|
| SAMD4A HD DNA FISH probe primers | | |
| SAMD4A5'1F | CTCCAAAAACCTGACTTCGC | SEQ ID NO: 297 |
| SAMD4A5'1R | TGTCCTAATTGGCCTGATCC | SEQ ID NO: 298 |
| SAMD4A5'2F | CCACCCAACATGCTCTCTTT | SEQ ID NO: 299 |
| SAMD4A5'2R | CCATCATTTACCAGCCCTGT | SEQ ID NO: 300 |
| SAMD4A5'3F | GCTCATTGCCCTGCAGATAG | SEQ ID NO: 301 |
| SAMD4A5'3R | TGATCCTCCAGTAACCGCAT | SEQ ID NO: 302 |
| SAMD4A5'4F | AGACCTGCATTTCCTTCCCT | SEQ ID NO: 303 |
| SAMD4A5'4R | ACTGTGGCTCTGTTGCCTTT | SEQ ID NO: 304 |
| SAMD4A5'5F | CCCTCAGACCCACTTCACAT | SEQ ID NO: 305 |
| SAMD4A5'5R | CCCTTCTGCACGTCTCTTCT | SEQ ID NO: 306 |
| SAMD4A5'6F | CAGTGTCTATTCAGAAACCACAGAA | SEQ ID NO: 307 |
| SAMD4A5'6R | CGTGAGTTCAGGCCTACTGTC | SEQ ID NO: 308 |
| SAMD4A5'7F | CATGCAGAGAAGATCACCATT | SEQ ID NO: 309 |
| SAMD4A5'7R | GGGCCAAGTCCTCAAGATAA | SEQ ID NO: 310 |
| SAMD4A5'8F | TGGCAATTATCCATTGTCATTT | SEQ ID NO: 311 |
| SAMD4A5'8R | TGTTTAAGAGGATGCCTGGG | SEQ ID NO: 312 |
| SAMD4A5'9F | TTAGTAATCTTTGGAACATCTGAACA | SEQ ID NO: 313 |
| SAMD4A5'9R | GGCACTGAATACACGATGGG | SEQ ID NO: 314 |
| SAMD4A5'10F | TTATTGCCTAACCCAGTGCC | SEQ ID NO: 315 |
| SAMD4A5'10R | TCCTATGTCAACCTGGACCC | SEQ ID NO: 316 |
| SAMD4A5'11F | TCAAGCCTTTCTGCCTCTACA | SEQ ID NO: 317 |
| SAMD4A5'11R | GACACGTGATAGCACCTAACCA | SEQ ID NO: 318 |
| SAMD4A5'12F | ACATATGCCGGAGTTGGAAA | SEQ ID NO: 319 |
| SAMD4A5'12R | TCTGGGCTATCTCCGTGATT | SEQ ID NO: 320 |
| SAMD4A5'13F | GCACTCTCCAGATCCAGGTG | SEQ ID NO: 321 |
| SAMD4A5'13R | CTGGCTGAGTCCCACTCTTC | SEQ ID NO: 322 |
| SAMD4A5'14F | AACCACATTCCCAAGGACAA | SEQ ID NO: 323 |
| SAMD4A5'14R | GGTCGGGTAGAAGGAACCTC | SEQ ID NO: 324 |
| SAMD4A5'15F | GTCCCCACTTAGGAATCCGT | SEQ ID NO: 325 |
| SAMD4A5'15R | GCTGCTGCCTCCAGTGTC | SEQ ID NO: 326 |
| SAMD4A5'16F | ACTCGAAGCACCGCACTC | SEQ ID NO: 327 |
| SAMD4A5'16R | GAGGGGACCCCCAGTGAC | SEQ ID NO: 328 |
| SAMD4A5'17F | AGCAGGCTTCTCGCTGTTAC | SEQ ID NO: 329 |
| SAMD4A5'17R | GGAGAGAAAGAGCTGCAGTGA | SEQ ID NO: 330 |
| SAMD4A5'18F | ACCACCGGAACGTAACTGAA | SEQ ID NO: 331 |
| SAMD4A5'18R | CGAAACATCATGGTTAGGGG | SEQ ID NO: 332 |
| SAMD4A5'19F | GGATTTTGCCCACTGTGAAC | SEQ ID NO: 333 |
| SAMD4A5'19R | CGGGCATCTATCATGTGTTG | SEQ ID NO: 334 |

TABLE 2-continued

Sequences of PCR primers used to construct "high definition" FISH probes

| Primer Name | Primer Sequence (5'-3') | Sequence Identity Number |
|---|---|---|
| SAMD4A5'20F | TTCCTATTTGCTAGCGTGGG | SEQ ID NO: 335 |
| SAMD4A5'20R | ATGGAACAGCTGGAAGAGGA | SEQ ID NO: 336 |
| TNFAIP2 HD DNA FISH probe primers | | |
| TNFAIP23'1F | GGGCAAAGCAATCAATAACC | SEQ ID NO: 337 |
| TNFAIP23'1R | TTCTCCCCTACCTGCCCTAT | SEQ ID NO: 338 |
| TNFAIP23'2F | TACCCCTGCTGAGTACAGCC | SEQ ID NO: 339 |
| TNFAIP23'2R | ACCTCCAGGCTTCCTTCCTA | SEQ ID NO: 340 |
| TNFAIP23'3F | GAGGAGTCAGCAGGGCATAG | SEQ ID NO: 341 |
| TNFAIP23'3R | AGCTTGGCTTTAGTTGCCTG | SEQ ID NO: 342 |
| TNFAIP23'4F | AGGGGCAGAGAGAAGGTCAT | SEQ ID NO: 343 |
| TNFAIP23'4R | AGGTCTTGGGCATCTCACC | SEQ ID NO: 344 |
| TNFAIP23'5F | TTTGGAGCAGGACCTAATGG | SEQ ID NO: 345 |
| TNFAIP23'5R | ACCACTCAAGCTAGAGCCCA | SEQ ID NO: 346 |
| TNFAIP23'6F | CTGCCTGCAGTGACATCATC | SEQ ID NO: 347 |
| TNFAIP23'6R | CTGCCCATGTCCTGTCTGT | SEQ ID NO: 348 |
| TNFAIP23'7F | GCCAATGTGAGGGAGTTGAT | SEQ ID NO: 349 |
| TNFAIP23'7R | CATGGGTATGCACACAGGAC | SEQ ID NO: 350 |
| TNFAIP23'8F | CTGGACTTGGGCTCACAGAT | SEQ ID NO: 351 |
| TNFAIP23'8R | GCTGAGTGGGAAACAACTCC | SEQ ID NO: 352 |
| TNFAIP23'9F | TCTGACCTCCACCAGGATTC | SEQ ID NO: 353 |
| TNFAIP23'9R | TAGGAGTGAGCGTGTGGTTG | SEQ ID NO: 354 |
| TNFAIP23'10F | AGATGGGCTGGTACCCTCTT | SEQ ID NO: 355 |
| TNFAIP23'10R | GTAGCTGGCGAAACCAGAAG | SEQ ID NO: 356 |
| TNFAIP23'11F | TTCTGGAGAGAGGCAAGCAG | SEQ ID NO: 357 |
| TNFAIP23'11R | TCCTCACACATGTTGCTGGT | SEQ ID NO: 358 |
| TNFAIP23'12F | CAAGCACACAGGCAGATGTT | SEQ ID NO: 359 |
| TNFAIP23'12R | CAATGGCTCCCCATTCTCTA | SEQ ID NO: 360 |
| TNFAIP23'13F | GGATGTCCATGGAGCAGAAT | SEQ ID NO: 361 |
| TNFAIP23'13R | CTTTGCTTCTGCCACTCCTC | SEQ ID NO: 362 |
| TNFAIP23'14F | ATTCAGACACAGCCCAGTCC | SEQ ID NO: 363 |
| TNFAIP23'14R | CCCCACTTTACACCCTGCTA | SEQ ID NO: 364 |
| TNFAIP23'15F | GGGTGACCTTGGATAAGGGT | SEQ ID NO: 365 |
| TNFAIP23'15R | GAGACAGGAGAGGCAGGATG | SEQ ID NO: 366 |
| TNFAIP23'16F | ATCATCCAACTCAGCAAGGG | SEQ ID NO: 367 |
| TNFAIP23'16R | GGGCTTAGAGAGGCACCAG | SEQ ID NO: 368 |
| TNFAIP23'17F | ATTGAGGTGGCCACTTATGC | SEQ ID NO: 369 |
| TNFAIP23'17R | TCGTAGTGCTGTGGTGAAGG | SEQ ID NO: 370 |

TABLE 2-continued

Sequences of PCR primers used to construct "high definition" FISH probes

| Primer Name | Primer Sequence (5'-3') | Sequence Identity Number |
|---|---|---|
| TNFAIP23'18F | TGGCCCACACTCTTAGCTTT | SEQ ID NO: 371 |
| TNFAIP23'18R | AACATGTCAGAGGACCCAGC | SEQ ID NO: 372 |
| TNFAIP23'19F | AAGGGAAGCCAGGTCTCAGT | SEQ ID NO: 373 |
| TNFAIP23'19R | CTTCCCACCCCTTAGGTCTC | SEQ ID NO: 374 |
| TNFAIP23'20F | AGTAGGGGTGTGGGTGACAG | SEQ ID NO: 375 |
| TNFAIP23'20R | GCCACAGGAAAAGCTAACCA | SEQ ID NO: 376 |
| SLC6A5 HD DNA FISH probe primers | | |
| SLC3'1F | GTTGGCTGTGGCTCCTAAAG | SEQ ID NO: 377 |
| SLC3'1R | CGCACTCCTCTCGTCTAACC | SEQ ID NO: 378 |
| SLC3'2F | CCTTGTCTTTGCTACCTGGC | SEQ ID NO: 379 |
| SLC3'2R | TCCCCATCACCACTGTAGAA | SEQ ID NO: 380 |
| SLC3'3F | CCATTCCCCCTTTACCCTTA | SEQ ID NO: 381 |
| SLC3'3R | GCAACTCAGGTCCAGACACA | SEQ ID NO: 382 |
| SLC3'4F | ATAAACTGCCAGCCAACAGC | SEQ ID NO: 383 |
| SLC3'4R | GAGTTTGCAAGACCCCACTC | SEQ ID NO: 384 |
| SLC3'5F | CGCTGCACTGTAAGATCCCT | SEQ ID NO: 385 |
| SLC3'5R | AATGCAACCTGCTTACCTGG | SEQ ID NO: 386 |
| SLC3'6F | ACGTATGCTGATGGGGAAAC | SEQ ID NO: 387 |
| SLC3'6R | CAACTCTTTCGTGGATCTGGA | SEQ ID NO: 388 |
| SLC3'7F | AGGTGGGTTTACCTGAGGCT | SEQ ID NO: 389 |
| SLC3'7R | GTGGGTTTTTCACGCCTCTA | SEQ ID NO: 390 |
| SLC3'8F | ATCTCCCACTTGCCTTTCCT | SEQ ID NO: 391 |
| SLC3'8R | CCATTCCTAATCCCACCCTT | SEQ ID NO: 392 |
| SLC3'9F | TGTCCTGCACACCCTGTAGA | SEQ ID NO: 393 |
| SLC3'9R | GGTCCTGGAATGCCTCACTA | SEQ ID NO: 394 |
| SLC3'10F | GCATCTTCGTGTGAGCTTGA | SEQ ID NO: 395 |
| SLC3'10R | TGGGAAGAGACAAGCCATCT | SEQ ID NO: 396 |
| SLC3'11F | GAAAGTAAGGCAGGGGCTCT | SEQ ID NO: 397 |
| SLC3'11R | CCCAACCCCTTACCAAGAAT | SEQ ID NO: 398 |
| SLC3'12F | TACAGGTTCAAGGTTTGGGG | SEQ ID NO: 399 |
| SLC3'12R | ATGCATCAGCAAGCAGGAC | SEQ ID NO: 400 |
| SLC3'13F | GCCTGCTTGTGGACCTACTC | SEQ ID NO: 401 |
| SLC3'13R | AGAGCGGAAAAGCCATACCT | SEQ ID NO: 402 |
| SLC3'14F | ACAGCCTCCTTAGGCTCCAG | SEQ ID NO: 403 |
| SLC3'14R | AACACTTGACCGCTAGCACC | SEQ ID NO: 404 |
| SLC3'15F | GTTGAGGCTGTGCTGTCAAA | SEQ ID NO: 405 |
| SLC3'15R | AGCCGATGCAAGCCTAACTA | SEQ ID NO: 406 |

TABLE 2-continued

Sequences of PCR primers used to construct "high definition" FISH probes

| Primer Name | Primer Sequence (5'-3') | Sequence Identity Number |
|---|---|---|
| SLC3'16F | CACTGCTTCACCCCATAGGT | SEQ ID NO: 407 |
| SLC3'16R | ATGGCAAATGCTCTGAGGTC | SEQ ID NO: 408 |
| SLC3'17F | ACACGAATAGAGGCACCCAG | SEQ ID NO: 409 |
| SLC3'17R | AACCCTGAGATCTGCCCC | SEQ ID NO: 410 |
| SLC3'18F | TTTTCAGGAGCAGAGGAGGA | SEQ ID NO: 411 |
| SLC3'18R | AGCGGAGGGAAAACTGATCT | SEQ ID NO: 412 |
| SLC3'19F | CCTCAAAGAATGCTGAAGGG | SEQ ID NO: 413 |
| SLC3'19R | CCTTCTGAGTCCTCCCACAG | SEQ ID NO: 414 |
| SLC3'20F | TGACCTTGAAGGATGGAAGG | SEQ ID NO: 415 |
| SLC3'20R | CCCAGGACCCAAAATCTTCT | SEQ ID NO: 416 |

Immuno-DNA FISH

Immunofluorescence was performed as above and cells were post-fixed with 3.7% formaldehyde/PBS for 20 min at room temperature. DNA FISH hybridization was performed as follows. Cells were washed twice in PBS for 5 min each and permeabilized in 0.5% Triton X-100 for 10 minutes. Cells were treated with 10 U of RNAseA in 2×SCC for 1 hr at 37° C. Cells were then washed twice with 2×SSC, and dehydrated in 70%, 85% and 100% ethanol for 2 min each. After air-drying, cells were denatured in 70% formamide, 2×SCC for 3 min at 73° C., and dehydrated in ice-cold 70%, 85% and 100% ethanol for 2 min each. Cells were then hybridized overnight in a humidified chamber at 37° C. in 10 µl of Hyb buffer (10% dextran sulfate, 50% formamide, 4×SSC) combined with 30 ng of DNA FISH probes that were freshly denatured for 5 min at 72° C. and cooled on ice. Coverslips were then washed 3×(5 min each on the orbital shaker) in each of three wash buffers—1) 50% formamide, 2×SCC, 2) 1×SSC and 3) 4×SSC, 0.01% Tween 20. Cells were counter stained with DAPI, mounted in glox buffer (3.7 µg/µl glucose oxidase, 1 U catalase) and imaged.

Repair Construct

The repair construct pCR-SAMD4A-IRES-GFP includes two segments, SAMD4A 5' Intron 1 and SAMD4A 3' Intron 1 of 564 bp and 563 bp respectively which are homologous to regions either side of the SAMD4A intron 1 TALEN cleavage site. Segment SAMD4A 5' Intron 1 includes 3' splice acceptor site and 52 bp of 3' intronic sequence derived from a modified chimeric intron used in the mammalian expression vector pCI-neo (Promega, WI, USA). Similarly, segment SAMD4A 3' Intron 1 includes a 5' splice donor site and 52 bp of 5' intronic sequence derived from a modified chimeric intron used in the mammalian expression vector pCI-neo (Promega, WI, USA). The resulting artificial exon, which includes an IRES-GFP cassette, allowed for independent in situ GFP expression off the SAMD4A promoter following repair (homologous recombination) and splicing. The primers used to amplify the 564 bp 5' SAMD4A fragment were as follows: SAMD4A 5' Intron F: 5'-TGC TGC TGC AGG AGG GTG-3' (SEQ ID NO:17); SAMD4A 5' Intron R: 5'-GAT CGC TAG CAC CTGTGGAGAGAAAGGCAAAGTGGATGTCAGTAAG ACCAATAGGTGCCTATCATG GCC CTC CAG CTA TTT ATA AAC GTG-3' (SEQ ID NO:18) (Bold=splice acceptor site; Underlined=intron extension from a modified chimeric intron derived from pCI-neo [Promega]). The primers used to amplify the 563 bp 3' SAMD4A fragment were as follows: SAMD4A 3' Intron F: 5'-GAT CGC TAG CAG GTAAGTATCAAGGTTACAAGACAGGTTTAAGGAGA CCAATAGAAACTGGGG CCT CCT TCA CTG GGG TGT G-3' (SEQ ID NO:19) (Bold=splice donor site; Underlined=intron extension from a modified chimeric intron derived from pCI-neo [Promega]); SAMD4A 3' Intron R: 5'-CTT TTG TAT ATC TAC ATC ATT TAG CAG CAT G-3' (SEQ ID NO:20). Both amplicons were digested with NheI (NEB) and ligated. Full length ligated products were selected by PCR with primers SAMD4A 5' intron F and SAMD4A 3' intron R and cloned into the TA vector pCR.2.1 (Invitrogen) to produce pCR-SAMD4A-5/3. The (HCV) IRES-GFP sequence was amplified from pHIV7-IRES-GFP (a gift from John Rossi) and cloned into the NheI site of pCR-SAMD4A-5/3 to produce pCR-SAMD4A-IRES-GFP. The primers used for amplification include: IRES F: 5'-GAT CGC TAG CCC CCC TAA CGT TAC TGG CCG-3' (SEQ ID NO:21) and GFP R: 5'-GAT CGC TAG CGG ATC CTC ACT TGT ACA GCT CGT CCA TGC C-3' (SEQ ID NO:22). To generate double stranded PCR product harboring the 20 and 18 bp homologous arms, the following primers were used: 5'-CCA CAC CCC AGT GAA GGA G-3' (SEQ ID NO:23) and 5'-TAA ATA GCT GGA GGG CCA TG-3' (SEQ ID NO:24). The PCR product was purified by QIAquick PCR Purification Kit (Qiagen) prior to transfection.

The Transcriptional Response of Co-Regulated Genes in a Multigene Complex is Asymmetric.

Figure 4:
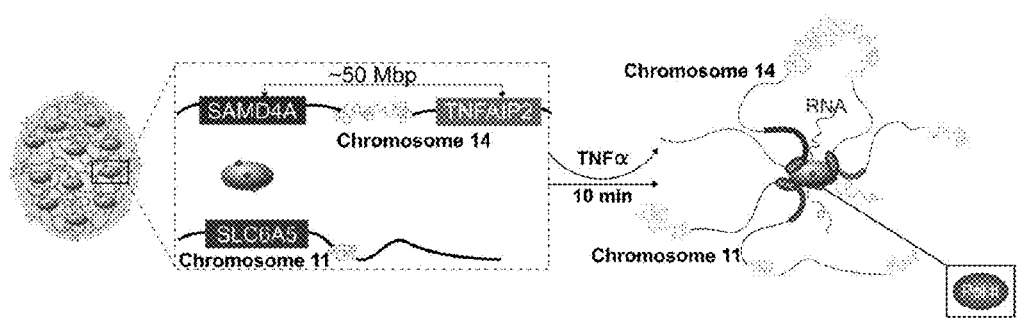
FIG. 4: The transcriptional response of co-regulated genes in a multigene complex is asymmetric. The promoters of genes located on the same chromosome (SAMD4A and TNFAIP) and on a different chromosome (SLC6A5) associate via RNA Polymerase II (orange) to form a NF-κB-dependent multigene complex. BMP4 and RCOR1 are non-responsive to TNFα, do not interact with SAMD4A (blue), TNFAIP2 (green) or SLC6A5 (red), and therefore serve as controls in this study.
Figure 5:
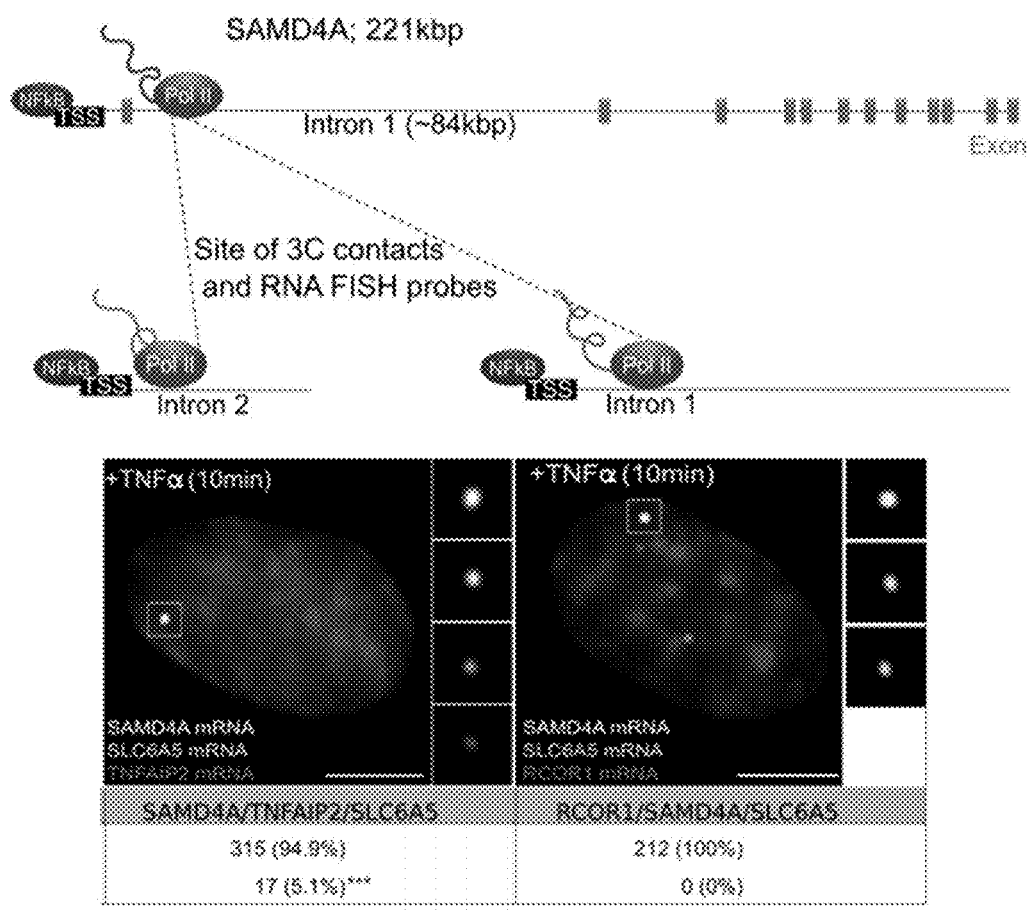
FIG. 5: The transcriptional response of co-regulated genes in a multigene complex is asymmetric. Chromosomal contact in a multigene complex is associated with cotranscription. Spectrally distinct RNA FISH intronic probes targeting the region of these genes involved in chromosomal contact reveal co-localization of nascent intronic RNA, as visualized by overlapping foci. Two-tailed Fisher exact test; ***P=4.5E-4, n, number of alleles.
Figure 6:
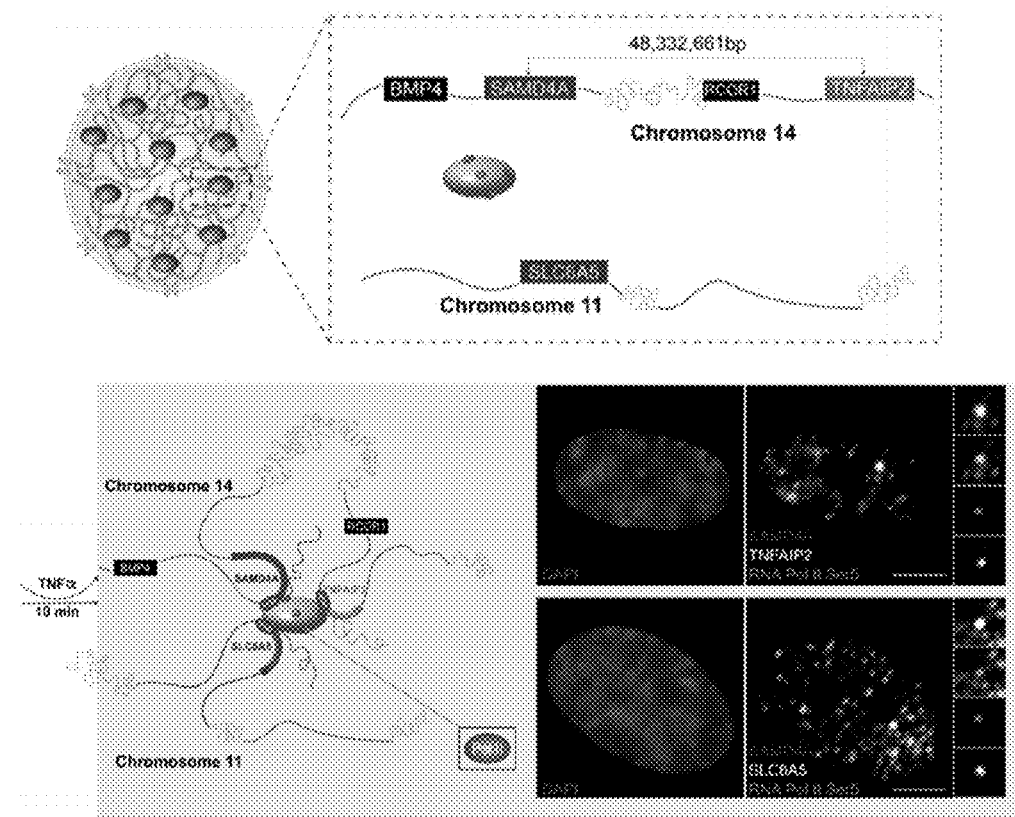
FIG. 6: RNA Pol II-mediated SAMD4A, TNFAIP2 and SLC6A5 co-transcription may occur within TADs. Overlapping SAMD4A, TNFAIP2 and/or SLC6A5 RNA FISH foci consistently co-localize with the active, poised form of RNA Pol II (phosphorylated at Serine 5). Bar, 10 μm.
Figure 7:
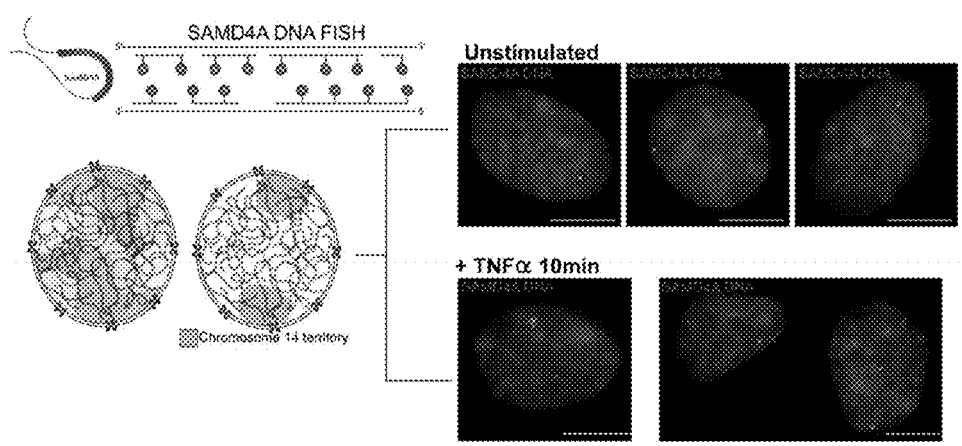
FIG. 7: RNA Pol II-mediated SAMD4A, TNFAIP2 and SLC6A5 co-transcription may occur within TADs. HUVECs always display two spatially distinct DNA FISH foci, both before and after TNFα treatment. Cells were counterstained with DAPI. Bar, 5 μm.
Figure 8:
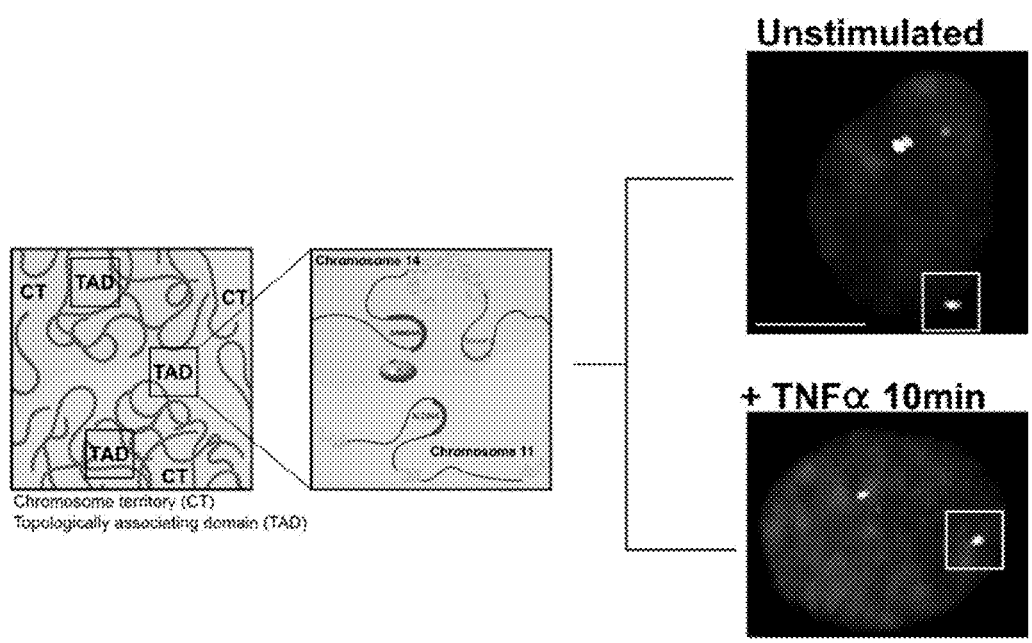
FIG. 8: RNA Pol II-mediated SAMD4A, TNFAIP2 and SLC6A5 co-transcription may occur within TADs. Analysis of overlapping DNA FISH foci revealed co-localized foci in both the unstimulated and the TNFα-treated HUVEC population. Cells were counterstained with DAPI. Bar, 5 μm.

TNFα has been shown to rapidly and synchronously shape the transcriptional response in early passage human umbilical vein endothelial cells (HUVECs) by systematically inducing the formation of a large variety of different multigene complexes (Papantonis et al., 2012). Interacting genes in TNFα-induced multigene complexes are activated by NF-κB (Papantonis et al., 2010). The SAMD4A, TNFAIP2 and SLC6A5 genes associate in a NF-κB dependent multigene complex (FIG. 4), which has been extensively characterized by 3C, 4C (3C capture-on-chip), tiling microarray and FISH, and thus is an ideal model to interrogate the role chromosomal contacts play in cotranscription at a single cell level (Papantonis et al., 2010; Papantonis et al., 2012). HUVECs were arrested in the G0 phase of the cell cycle by serum deprivation. Importantly, the transcription of SAMD4A, TNFAIP2 and SLC6A5 is rapidly induced 10 mins post TNFα stimulation (FIG. 5; Papantonis et al., 2010). Concurrent to their expression at 10 mins, prior 3C data including our own (data not shown) (Papantonis et al., 2010), indicate that chromosomal contacts between these genes occur at sites ~1.5 kbp downstream of the TSS (FIG. 5). To interrogate whether the formation of these contacts are associated with cotranscription, we designed RNA FISH probes to target the intronic sites where these contacts occur 10 mins post TNFα treatment (FIG. 5). As these introns are typically spliced and degraded co-transcriptionally, these probes label the transcriptional start site (TSS). Each set of gene-specific RNA FISH intronic probes was conjugated to spectrally distinct fluorophores. By simultaneously performing RNA FISH on the 3 NF-κBregulated genes, we were able to investigate the frequency of these interactions across a population of cells. Consistent with previous studies (Papantonis et al., 2010, Papantonis et al., 2012), analysis of overlapping RNA FISH foci revealed co-localized foci in only a fraction of all alleles in the total population (~5%) (FIG. 5). Chromosomal interactions between transcribed genes have been shown to occur at discrete foci of active RNA Pol II, as well as at nuclear speckles. Overlapping SAMD4A, TNFAIP2 and/or SLC6A5 RNA FISH foci consistently co-localize with the active, poised form of RNA Pol II (phosphorylated at Ser5) (FIG. 6). Collectively, these data suggest that the co-transcription of these genes at RNA pol II foci may only occur in a small fraction of the HUVEC population. Chromosomes in primary cells occupy distinct territories in the nucleus. As HUVECs are primary cells, they always display two spatially distinct DNA FISH foci, both before and after TNFα treatment (FIG. 7). Within territories, chromosomes are segregated further into topologically associating domains (TADs). As a consequence of this compartmentalization, interacting genes in multigene complexes may be confined within much smaller genomic neighborhoods. By simultaneously performing DNA FISH on these 3 co-regulated genes, we were able to investigate whether the DNA of these 3 genes were in close vicinity prior to activation by TNFα. Interestingly, analysis of overlapping DNA FISH foci revealed proximal foci in both the unstimulated and the TNFα-treated HUVEC population (FIG. 8). This data suggest that in a fraction of the HUVEC population, the DNA of the SAMD4A, TNFAIP2 and SLC6A5 genes may be constrained within a TAD, prior to TNFα induction.

Figure 9:
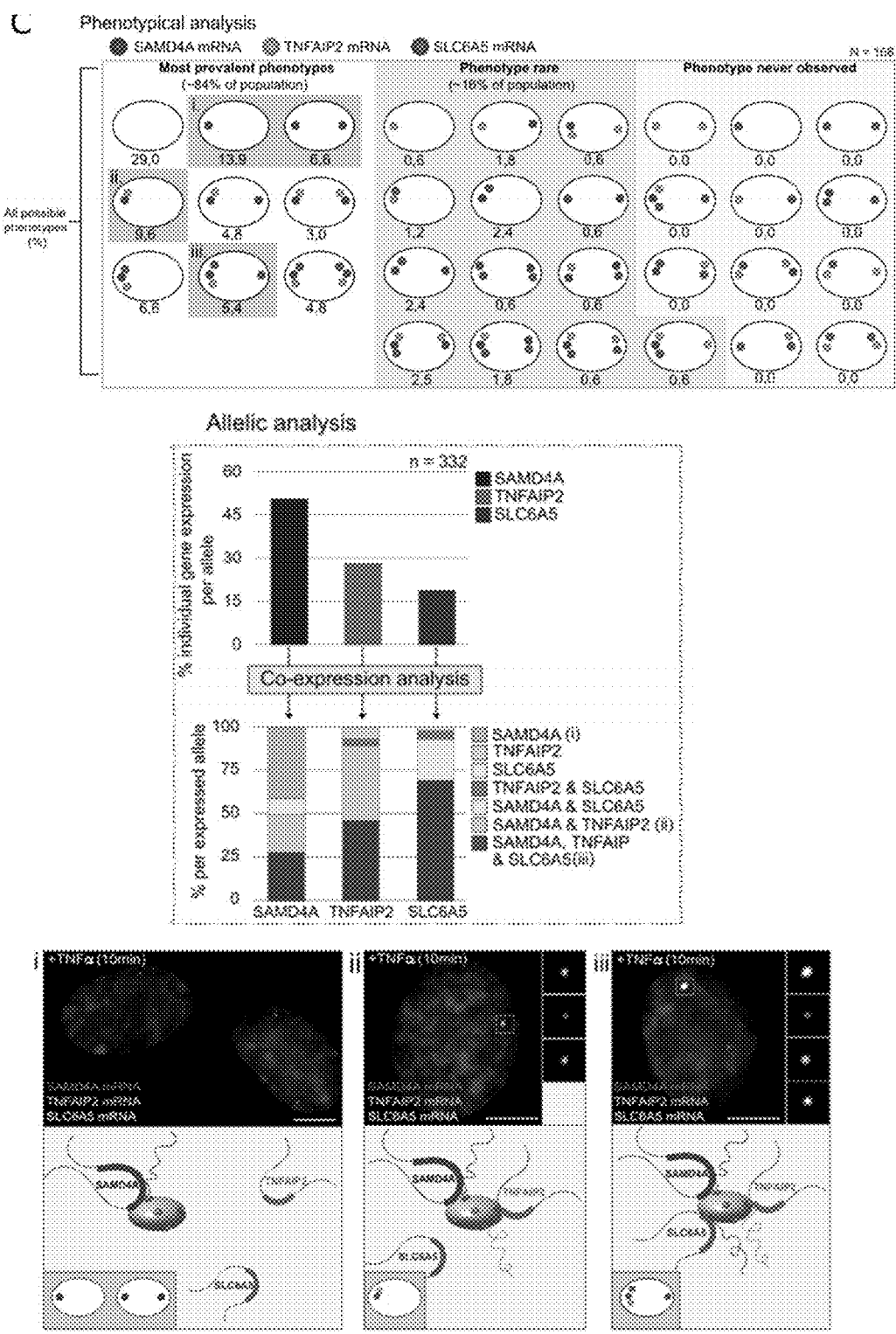
FIG. 9: The transcriptional response of co-regulated genes in a multigene complex is asymmetric. The response to TNFα is asymmetric in diploid HUVECs. Allelic expression of each gene in the population of cells is shown. TNFAIP2 transcription occurs predominantly when SAMD4A is also transcribed (~86%) and SLC6A5 transcription occurs mainly when SAMD4A (~92%), or both SAMD4A and TNFAIP2 are transcribed (~62%). N, number of cells (N=166), n, number of alleles (n=332).

Through an enrichment of chromosomal interactions in TADs, and higher levels of transcription, "jackpot" cells may contribute to variable, or stochastic effects, in gene expression (Noordermeer et al., 2011). As these NF-κBregulated genes respond stochastically to TNFα (Papantonis et al., 2010), we assessed the monoallelic and biallelic expression of the three genes. Nine of the 33 possible phenotypes were observed in the majority of the population (~84%) (FIG. 9). With the exception of cells displaying no foci (~29%), all cells in this category displayed either a single or dual SAMD4A foci. With respect to the individual expression of each of the 3 genes, not all cells respond similarly to TNFα, with approximately half of the alleles expressing SAMD4A, a lower proportion expressing TNFAIP2 and approximately one fifth expressing SLC6A5 (FIG. 9). As chromosomal contact occurs between these 3 genes (FIG. 5; Papantonis et al., 2010), the asymmetric transcriptional response of these genes to TNFα suggests a hierarchical regulation in the assembly of this multigene complex. Supporting this hypothesis, TNFAIP2 transcription occurs predominantly when SAMD4A is also transcribed (~86%) and SLC6A5 transcription occurs mainly when SAMD4A (~92%), or both SAMD4A and TNFAIP2 are transcribed (~62%) (FIG. 9).

Figure 10:
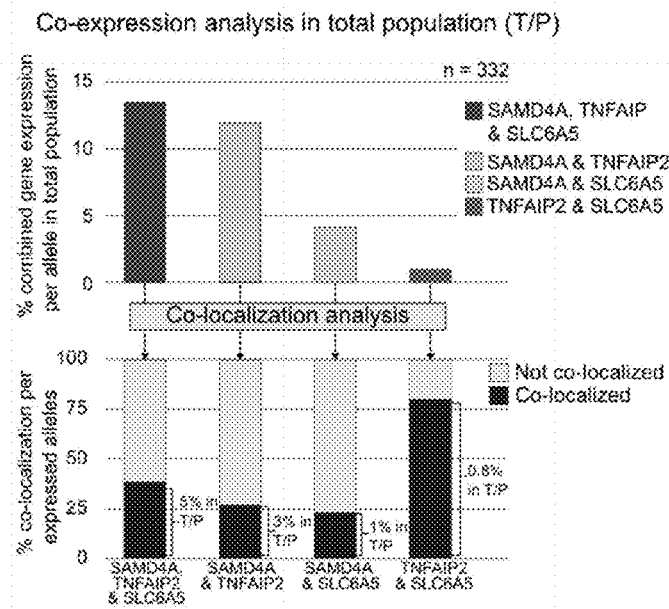
FIG. 10: The transcriptional response of co-regulated genes in a multigene complex is asymmetric. Data in (C) was replotted to show the combined allelic transcriptional status of SAMD4A, TNFAIP2 and SLC6A5 in the total population (T/P). Colocalization frequencies relative to cells co-expressing SAMD4A, TNFAIP2 and/or SLC6A5 is also shown. n, number of alleles, Bar, 5 μm. See also FIGS. 6, 7 and 8.

As SAMD4A, TNFAIP2 and SLC6A5 are not always co-expressed (FIG. 9), we also represented the co-localization frequencies relative to cells coexpressing SAMD4A, TNFAIP2 and/or SLC6A5 (FIG. 10). Allelic coexpression analyses between the 3 genes revealed that co-expression of SAMD4A and TNFAIP2, as well as triple expression of the 3 genes was most prevalent across the population (~12% and ~14% respectively) (FIG. 10). SLC6A5 was rarely expressed (~4%) in the absence of TNFAIP2 expression at the corresponding allele (FIG. 10). Moreover, co-transcription of TNFAIP2 and SLC6A5 in the absence of SAMD4A transcription was extremely rare (~1%) (FIG. 10). This provides further evidence for a relationship between the transcriptional status of SAMD4A and the transcriptional activation of TNFAIP2 and SLC6A5. With respect to coexpressed alleles, SAMD4A and TNFAIP2 were co-localized at ~26% of coexpressed alleles (3% in the total population (T/P)), whilst SAMD4A, TNFAIP2 and SLC6A5 were co-localized at ~40% of all co-expressed alleles (5% in the T/P) (FIG. 10). Collectively, these data suggest a hierarchical mode of regulation between these genes, in which chromosomal contact favors cotranscriptional activation.

Visualization of TALEN-Mediated Gene Loop Disruption

Figure 11:
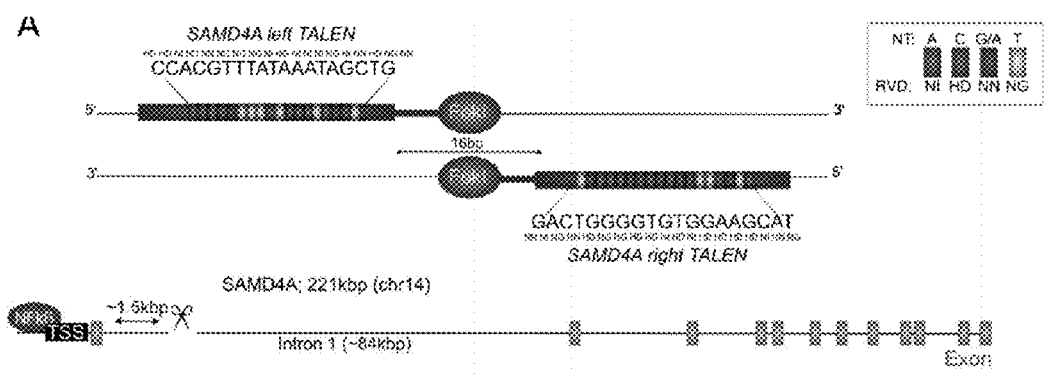
FIG. 11: Visualization of TALEN-mediated disruption of a gene loop. The SAMD4A TALEN targets the region in intron 1 involved in chromosomal contact 10 mins post TNFα stimulation. TALE repeat domains are colored to indicate the identity of repeat variable diresidues (RVD); each RVD is related to the cognate targeted DNA base by the following code; NI=A, HD=C, NN=G/A, NG=T.
Figure 12:
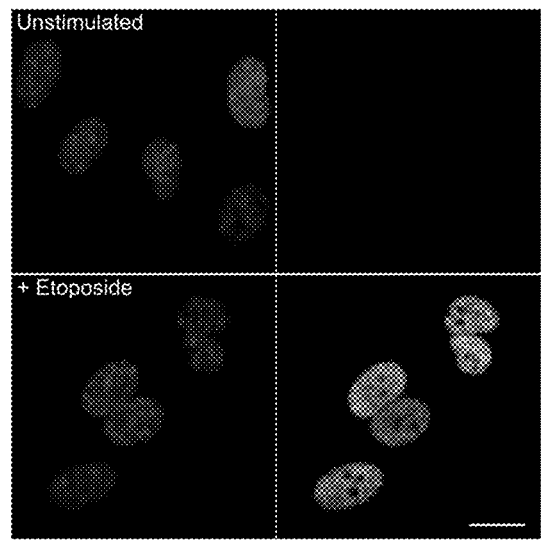
FIG. 12: Detection of double strand breaks in HUVECs. Indirect immunofluorescence was performed using an antibody specific to Ser139 phosphorylation of histone variant, H2A.X. DSBs labeled by H2A.X were detected with a donkey-anti rabbit antibody conjugated to Atto488. Distinct nuclear staining was evident in HUVECs treated with 100 μM Etoposide, a DSB-inducer, for 1 hr. Cells were counterstained with DAPI. Bar, 5 μm.
Figure 13:
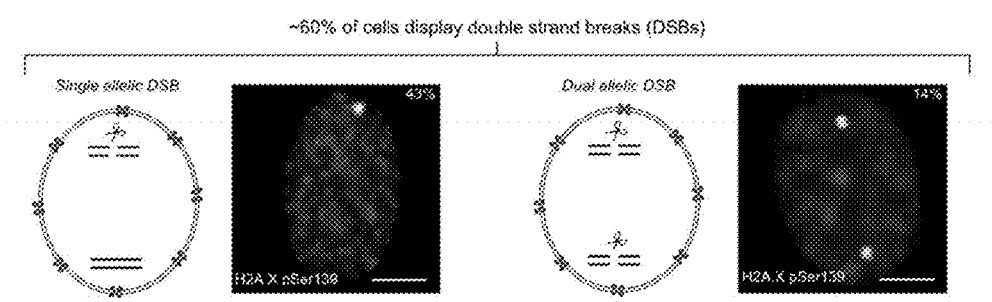
FIG. 13: Visualization of TALEN-mediated disruption of a gene loop. Successful detection of TALEN transfection at a single cell level. Discrete sites of H2A.X pSer139 were evident in ~60% of HUVECs transfected with the SAMD4A TALEN. A higher portion of successfully transfected cells displayed single allelic DSBs than dual allelic DSBs.
Figure 14:
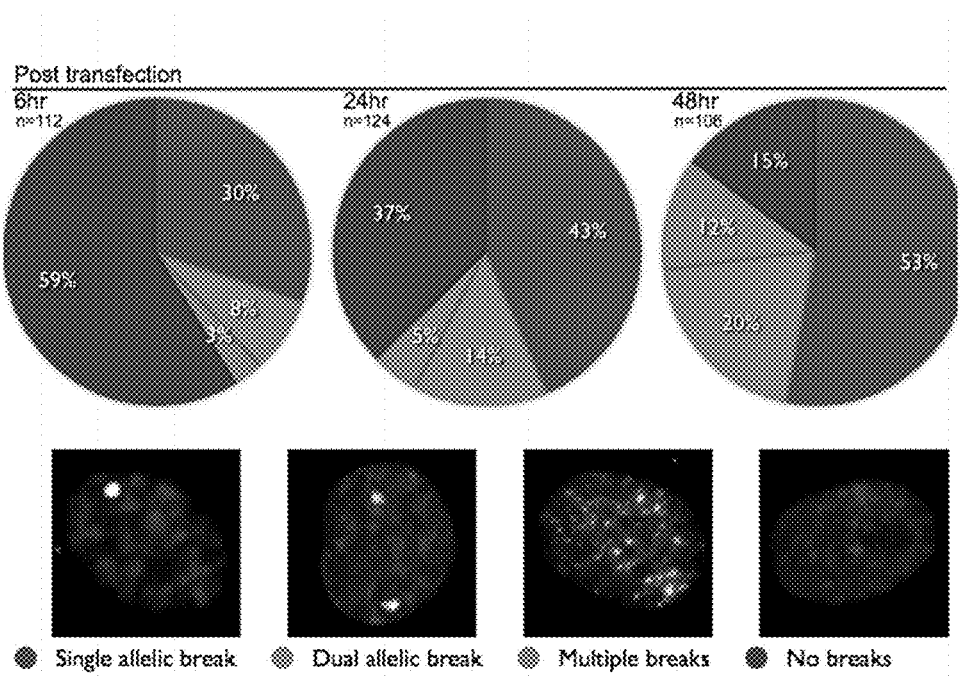
FIG. 14: A time course of SAMD4A TALEN nuclease activity. DSBs, labeled by an H2A.X pSer139 primary antibody, were detected with a donkey-anti rabbit secondary antibody conjugated to Atto488. Nuclease activity (a measure of transfection efficiency) was first evident after 6 hr as evidenced by distinct sites of H2A.X pSer139 in ~40% of HUVECs transfected with the SAMD4A pcDNA TALENs. At this time point, the majority of cell displayed no H2A.X foci and low levels of apoptotic cells, as evidenced by cells displaying multiple breaks (more than 2). Post 24 hr transfection, ~60% of cells displayed DSBs, with slightly higher levels of apoptotic cells (~5%). After 48 hr post transfection, ~70% of cells displayed DSBS and the level of apoptotic cells increased to ~12%. At all time points, a higher portion of transfected cells displayed single allelic DSBs than dual allelic DSBs (at a ratio of ~3:1).
Figure 15:
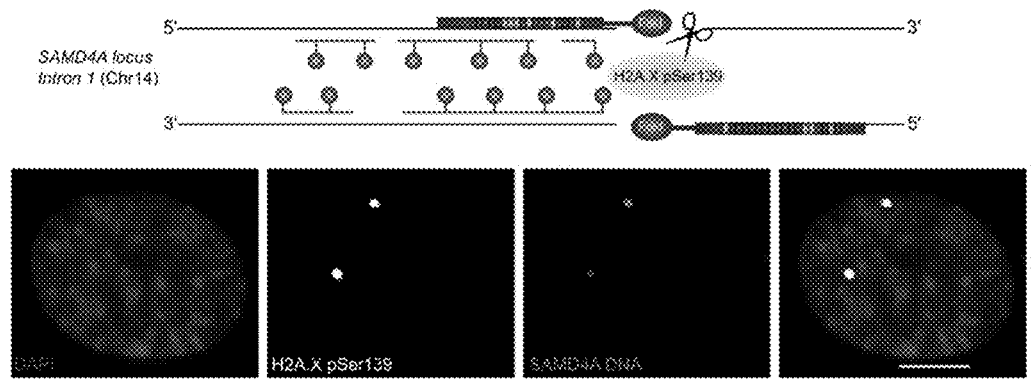
FIG. 15: Visualization of TALEN-mediated disruption of a gene loop. H2A.X immunofluorescence accurately labels the sites of the disrupted SAMD4A gene loop. SAMD4A DNA FISH foci consistently co-localize with SAMD4A TALEN-induced DSBs.
Figure 16:
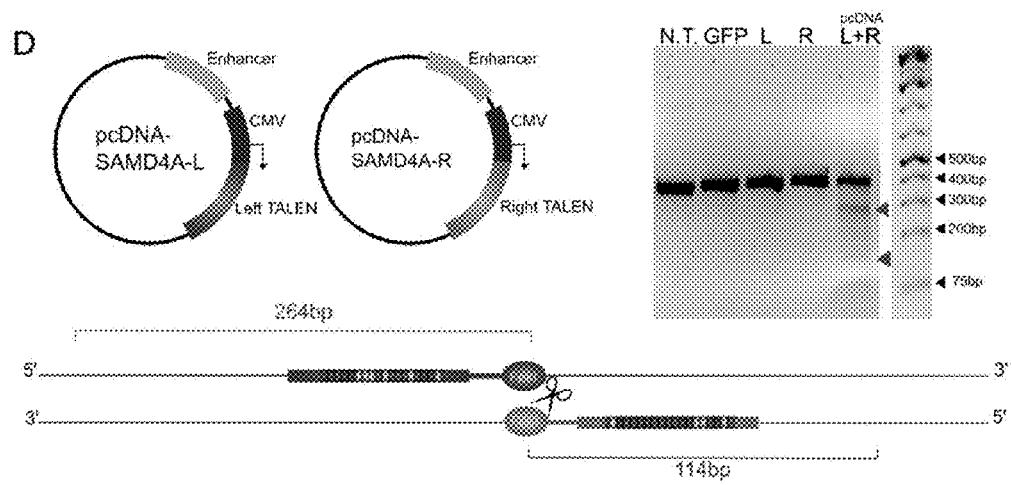
FIG. 16: Visualization of TALEN-mediated disruption of a gene loop. Gel showing the surveyor nuclease result from the SAMD4A TALEN pair. NT, un-transfected control; GFP, GFP transfected cells; L, SAMD4A left TALEN only; R, SAMD4A right TALEN only; L+R, cells transfected with pcDNA left and right TALENs. Red arrow, 246 bp, blue arrow, 114 bp. Cells were counterstained with DAPI. Bar, 5 μm. See also FIGS. 12, 14, 21, 32 and 41.

Hierarchical regulation dependent on chromosomal contact was revealed in the GREB1 multigene complex (Li et al., 2012). qPCR analysis revealed that siRNAs targeting ERα disrupted not only GREB1 transcription, but were sufficient to cause more than a 2 to 4-fold reduction in the transcription of interacting members. siRNA approaches cannot be applied to the TNFα-induced multigene complex, as these 3 genes are transcriptionally activated by NF-κB (Papantonis et al., 2010). Toward this end, we developed a single cell assay allowing the discrete disruption of individual gene loops at the sites of chromosomal contacts (FIG. 5). In parallel, to decrypt the role of a single individual gene loop on co-transcription in the same multigene complex, we visualized transcriptional activity of other genes in the multigene complex using highly sensitive RNA FISH (FIG. 5). We constructed our microscopy-based assay upon TALENs, the orthogonal and robust, well established genome editing tool derived from TAL effectors of *Xanthomonas* sp. (Christian et al., 2010, Li et al., 2011). Within the TALE structure, a central repeat domain mediates highly specific DNA recognition (Boch et al., 2009; Christian et al., 2010). Fusion of this domain to FokI endonuclease enables TALENs to induce site-specific double strand breaks (DSB) (Christian et al., 2010, Li et al., 2011). As the TALENs used in this study induce a DSB at the approximate site of chromosomal contact that occurs 10 mins post TNFα treatment (FIG. 11), we reasoned that should loop-mediated contact be required for co-transcription, the DSB would serve to rupture chromosomal contact between these genes. To ascertain whether the TALEN had successfully disrupted a gene loop, we stained for induction of a DSB using histone variant H2A.X (FIGS. 12 and 13). Rapidly phosphorylated at Ser139 within minutes following DNA rupture, this modification persists throughout the entire DNA repair process. To initially test our TALEN system and its ability to disrupt a single gene loop and concurrent assembly of the multigene complex, we introduced into HUVECs, by high efficiency microporation, our TALEN vectors that were able to disrupt the gene loop of the longest gene in the multigene complex, SAMD4A. We used H2A.X staining of DSBs to carefully establish a time course of TALEN activity (also a measure of transfection efficiency), noting that nuclease activity was first evident after ~6 hrs, and was sustained until ~48 hrs (FIG. 14). We chose to assay for nuclease activity after 24 hrs, as there were high levels of DSBs and low levels of cytotoxicity at this time point. Discrete sites of H2A.X phosphorylation were evident in ~60% of cells 24 hrs post transfection, with a higher proportion of these cells displaying single allelic DSBs, with fewer cells displaying dual allelic DSBs (FIG. 13). The high specificity of the SAMD4A TALEN was demonstrated by the consistent co-localization of SAMD4A DNA with the DSB, visualized by DNA FISH (FIG. 15). TALEN cleavage efficiency was further supported by the results of "surveyor assays" (FIGS. 16, 21, 32 and 42). Thus, we were able to assay uniquely for the disruption of the SAMD4A gene loop in its native environment at a single cell level.

TALEN-Mediated Disruption of a Gene Loop Abrogates RNA and Protein Expression

Figure 17:
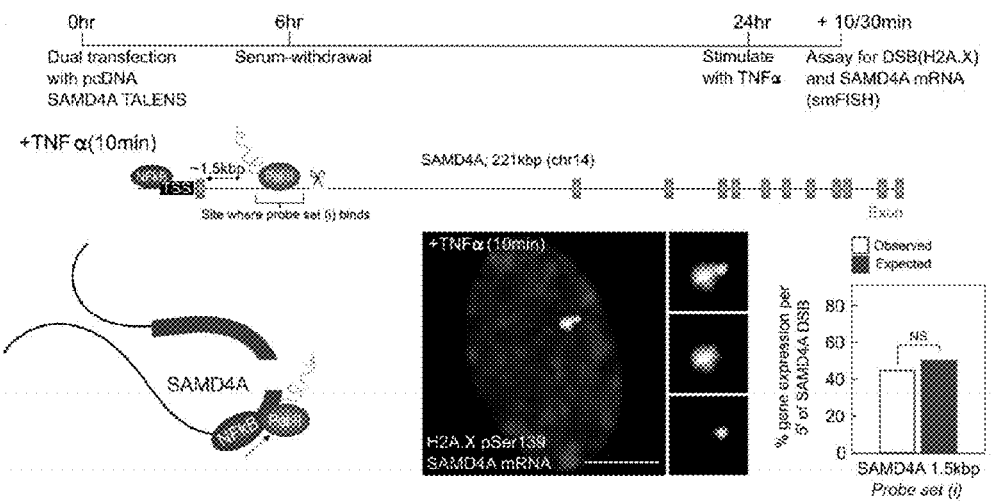
FIG. 17: TALEN-mediated disruption of the SAMD4A gene loop abrogates SAMD4A RNA and protein expression. SAMD4A TALEN-induced DSB does not alter transcription up to the DSB. Nascent intronic SAMD4A RNA (detected by probe set i) transcribed 5' of the DSB was evident in 42% of HUVECs displaying DSB, as evidenced by H2A.X staining. n, number of alleles (n=194), NS, no significant difference.
Figure 18:
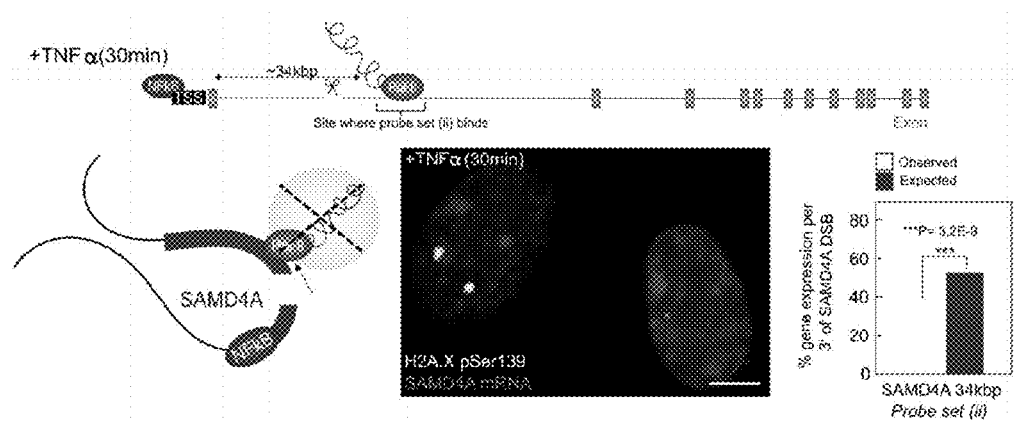
FIG. 18: TALEN-mediated disruption of the SAMD4A gene loop abrogates SAMD4A RNA and protein expression. The SAMD4A TALEN abrogates transcription downstream of the DSB. Nascent intronic SAMD4A RNA (detected by probe set ii) transcribed 3' of the DSB was never observed. n, number of alleles (n=84), Two-tailed Fisher exact test; ***P<0.001.

Upon stimulation by TNFα, RNA pol II engages the SAMD4A promoter, triggering a wave of transcription that propagates down the gene. RNA FISH tiling array analysis revealed that the transcriptional cycle takes approximately 85 min (Papantonis et al., 2010). Accordingly, RNA transcribed ~1.5 kbp downstream of the TSS appears within 10 mins (probe set i, FIG. 17), and ~34 kbp into intron 1 after 30 mins post TNFα stimulation (probe set ii, FIG. 18). Importantly, the DSB induced by the SAMD4A TALEN occurs at a site in between these two regions where different sets of intronic RNA FISH probes bind. HUVECs were dual transfected for 24 hrs with the SAMD4A TALENs and exposed to TNFα for 10 mins. This recapitulated SAMD4A transcriptional activity, allowing for the first ~1.5 kb of SAMD4A to be transcribed. By using RNA FISH to monitor intronic RNA transcription 10 mins post TNFα stimulation, SAMD4A transcription was frequently detected (~42%), either overlapping or in close proximity to the DSB (FIG. 17). Thus, these data indicate that despite disrupting the SAMD4A gene loop, the DSB did not appear to influence the ability of RNA Pol II to access the SAMD4A promoter, permitting transcriptional initiation and elongation up to the DSB. The half-life of SAMD4A intronic RNA transcripts transcribed at 10 mins is between 3 and 6 mins. Consequently, RNA transcripts transcribed downstream of the TSS at 10 mins, have degraded by the 30 mins time point. In a separate experiment, dual-transfected HUVECs were stimulated with TNFα for 30 mins to allow for the first ~34 kbp of SAMD4A to be transcribed (FIG. 18). Notably, the TALEN-induced perturbation was able to abrogate transcription of SAMD4A in this region, as no transcription of the intronic region of SAMD4A was ever evident beyond the DSB (FIG. 18)

Figure 19:
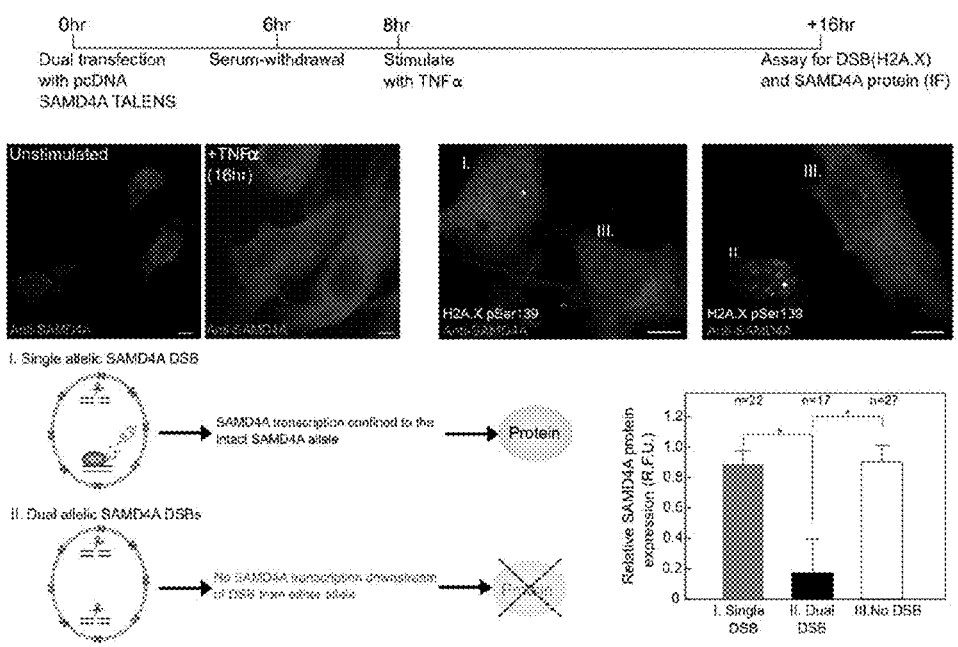
FIG. 19: TALEN-mediated disruption of the SAMD4A gene loop abrogates SAMD4A RNA and protein expression. Disrupting the SAMD4A gene loop is sufficient to abrogate protein expression. TNFα induces SAMD4A protein expression 16 hr post TNFα stimulation. Cells harboring dual allelic DSBs, as detected by H2A.X, displayed a significant reduction in protein expression, whilst cells harboring single allelic DSBs still express SAMD4A protein. R.F.U., relative fluorescent units, mean±SD, *P<0.01, Two-tailed unpaired Students t test, cells were counterstained with DAPI, Bar, 5 μm.

It has been published that DNA lesions alter RNA Polymerase II occupancy distal to DSBs, resulting in transcriptional inhibition (Shanbhag et al., 2010). This effect is mediated by ATM kinase activity, which results in the abrogation of Pol II-dependent elongation beyond the DSB. Importantly, ATM-mediated local inhibition of Pol II occurs in cis to DSBs (Shanbhag et al., 2010). Hence, in this study, the local inhibition of Pol II that occurs distal to the DSB, should not affect the intact allele in cells displaying single allelic DSBs.) IF in untransfected cells revealed that TNFα induction resulted not only in the robust transcription of members of the multigene complex, but also in an increase in protein expression (FIG. 19). Consistent with the ability of the TALEN to abrogate transcription, there was a significant reduction in SAMD4A protein expression in cells harboring dual allelic DSBs as detected by IF, whilst cells harboring single allelic DSBs were still able to express SAMD4A protein presumably from the intact allele (FIG. 19). Overall this robust assay offered an unprecedented perspective into the dynamics of TALEN activity, transcriptional status of the targeted gene and related protein levels at single cell resolution. Importantly, the observed disruption in SAMD4A RNA (FIG. 18) and protein expression (FIG. 19) strengthened our assay, as it validates that the DSB occurs at the intended site of TALEN activity where H2A.X staining occurred.

TALEN-Mediated Disruption of a Gene Loop Abrogates Expression of Interacting Members Satisfied that our TALEN assay was able to discretely disrupt SAMD4A at the site that engages in chromosomal contact, we repeated the prior experiment with an important modification: we used RNA FISH to visualize transcription of two other interacting genes that engage in intra- and inter-chromosomal with the region of SAMD4A that had been disrupted. By simultaneously monitoring SAMD4A gene loop disruption, as well as transcription of additional members of this multigene complex, we were able to interrogate discretely the effect of the disrupted SAMD4A gene loop on the transcriptional status of two other members of the complex.

Figure 20:
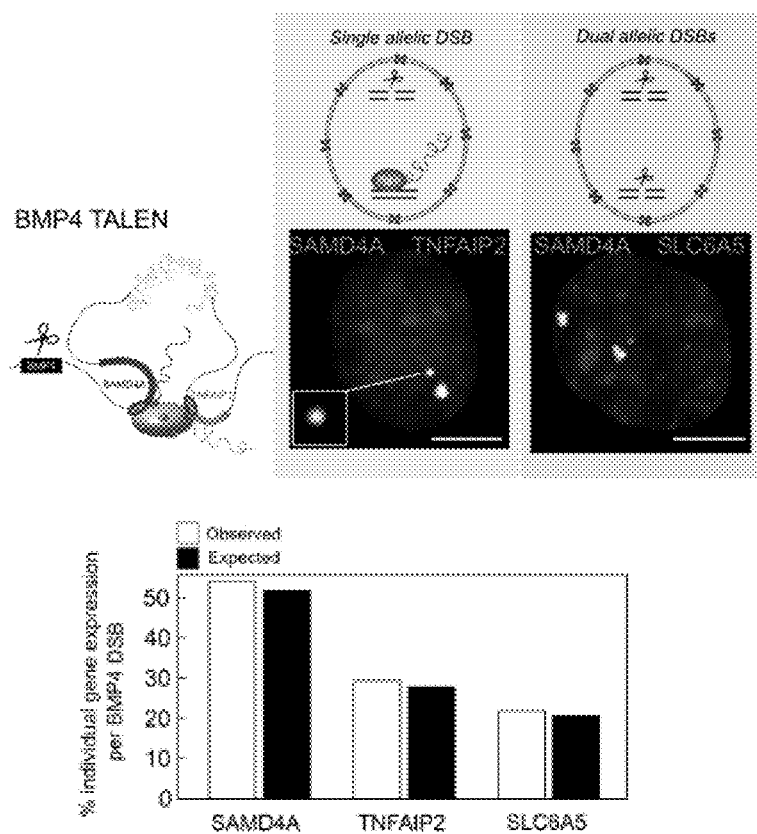
FIG. 20: TALEN-mediated disruption of a single gene loop and the associated chromosomal contacts in a multi-gene complex alters the transcriptional status of other genes occupying the same complex. A DSB induced in the non-TNFα responsive gene, BMP4, did not alter transcription of SAMD4A, TNFAIP2 or SLC6A5 relative to the normal TNFα response (FIG. 9).
Figure 21:
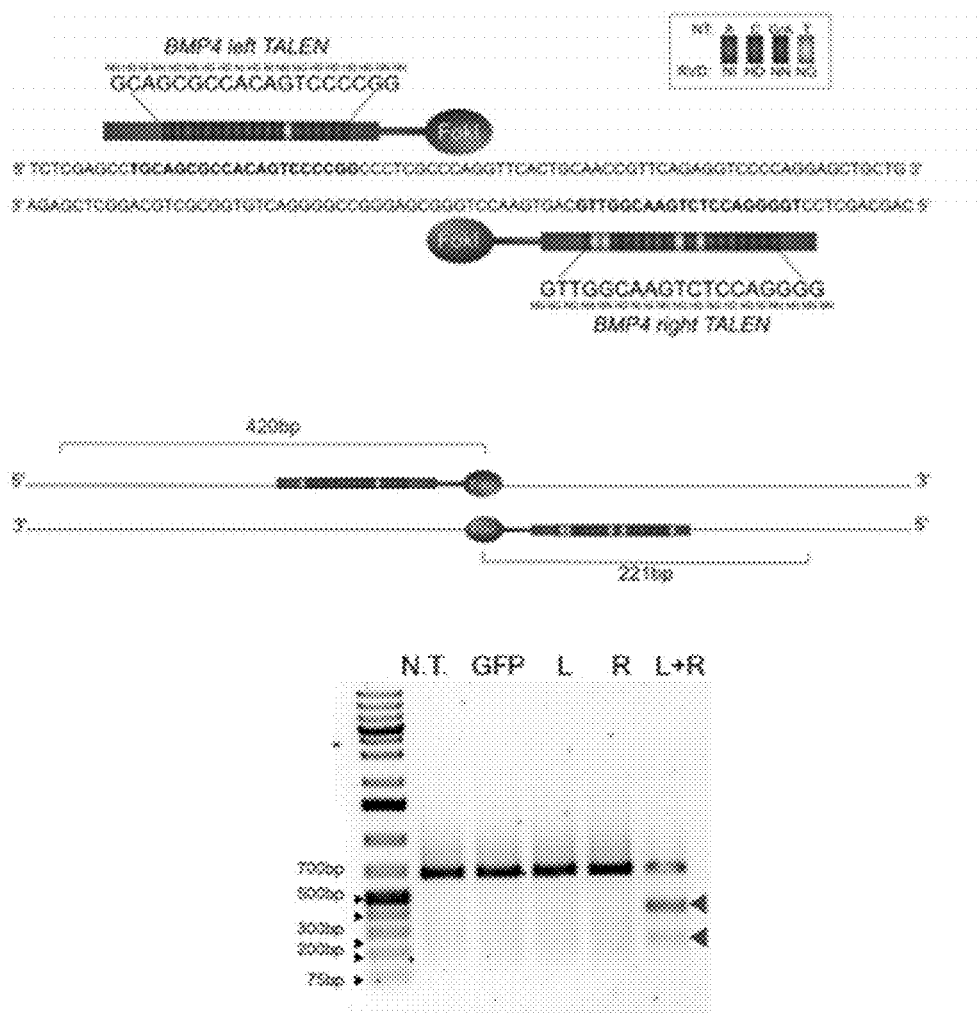
FIG. 21: Detection of TALEN efficiency. Gel showing the surveyor nuclease result from the BMP4 TALEN pair. NT, control from un-transfected cells; GFP, cells transfected with GFP; L, BMP4 left TALEN only; R, BMP4 right TALEN only; L+R, cells transfected with the BMP4 pcDNA left and right TALENs. MW, O'GeneRuler 1 kp Plus DNA ladder.

Firstly, to exclude the possibility that the DSB was capable of inducing cell cycle arrest, thereby altering global transcription, we designed a TALEN to rupture BMP4, a non-TNFα responsive gene, located ~600 kb 5' of SAMD4A on chromosome 14 (FIG. 20). We observed no change in the transcription of any of the three members of the multigene complex relative to the normal TNFα-induced transcriptional response (FIG. 9). Therefore, inducing a DSB 5' of SAMD4A has no effect on transcription of members of the multigene complex.

Figure 22:
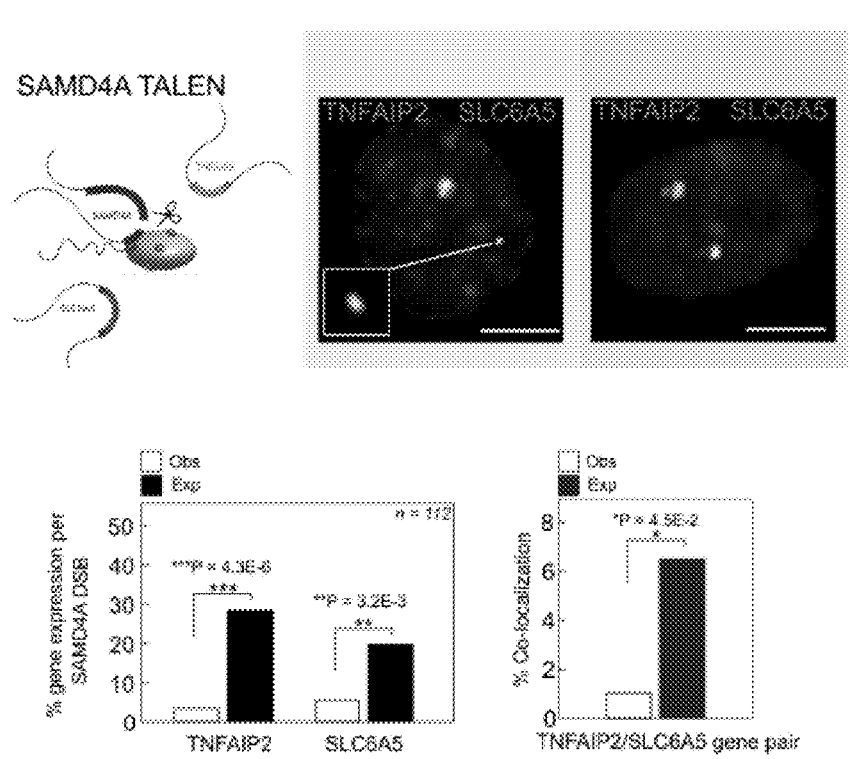
FIG. 22: TALEN-mediated disruption of a single gene loop and the associated chromosomal contacts in a multi-gene complex alters the transcriptional status of other genes occupying the same complex. The disruption of the SAMD4A gene loop abrogates TNFAIP2 and SLC6A5 transcription and co-localization. SAMD4A loop disruption detected by H2A.X was simultaneously monitored with transcription of TNFAIP2 and SLC6A5 by RNA FISH.
Figure 23:
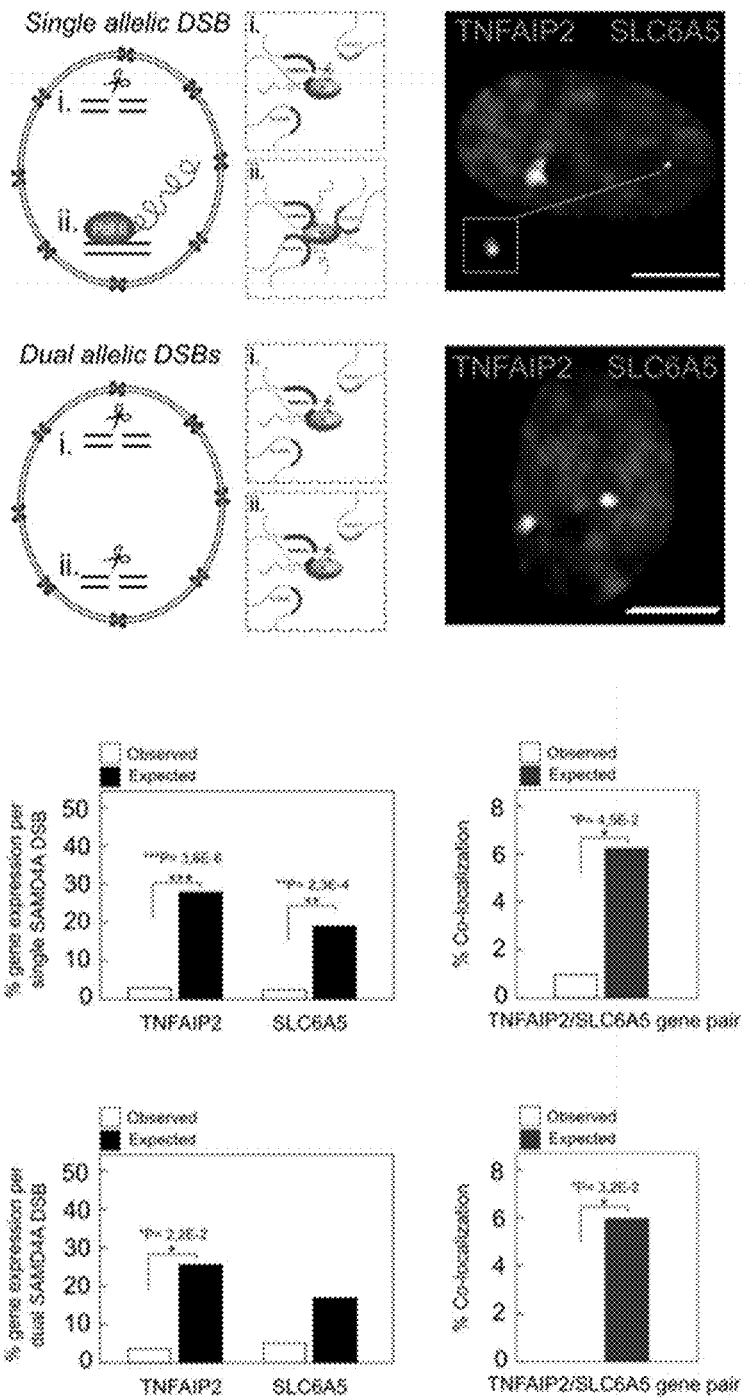
FIG. 23: Comparison between the phenotype in cells displaying a single allelic DSB to cells displaying dual allelic DSBs. In cells where a single allele of SAMD4A was targeted, virtually all transcription of TNFAIP2 and SLC6A5 was lost at the corresponding allele, with multi-gene transcription confined to the intact allele. Where both SAMD4A alleles were targeted, most transcription from TNFAIP2 and SLC6A5 was lost at both alleles. There was a significant reduction in TNFAIP2/SLC6A5 colocalization frequencies in both cells displaying single and dual allelic DSBs. Two-tailed Fisher exact test; *P<0.05, ***P<0.001, n, number of DSBs. Cells were counterstained with DAPI. Bar, 5 μm.

We then monitored the effects of perturbation of the chromatin loop of SAMD4A at its first intron. We observed a significant reduction of transcription of TNFAIP2 and SLC6A5 at the SAMD4A TALEN-induced DSB (FIG. 22). In cells where a single allele of SAMD4A was targeted, virtually all transcription of TNFAIP2 and SLC6A5, as assessed by RNA FISH, was lost at the corresponding allele or DSB, with multigene transcription confined to the intact allele (FIG. 23). Importantly, as the SAMD4A protein is still observed in cells harboring a single allelic DSB (FIG. 18), this observation excludes the possibility that the SAMD4A protein is required for the transcription of TNFAIP2 and SLC6A5.

Figure 24:
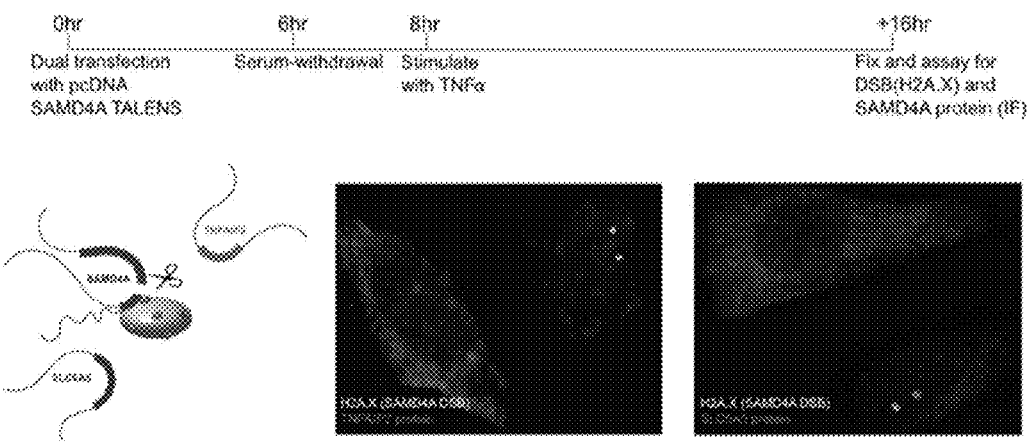
FIG. 24: TALEN-induced dual allelic DSBs abrogate protein expression of other members of the NF-kB multi-gene complex. Disrupting the SAMD4A gene loop is sufficient to abrogate protein expression of TNFAIP2 and SLC6A5. Dual indirect immunofluorescence was performed using a donkey-anti rabbit antibody conjugated to Atto488 to detect H2A.X and donkey-anti-goat secondary antibody conjugated to Atto565 to detect TNFAIP2 or SLC6A5. Cells displaying dual SAMD4A-induced DSBs, as detected by H2A.X, displayed a severe reduction in protein expression of TNFAIP2 and SLC6A5.
Figure 26:
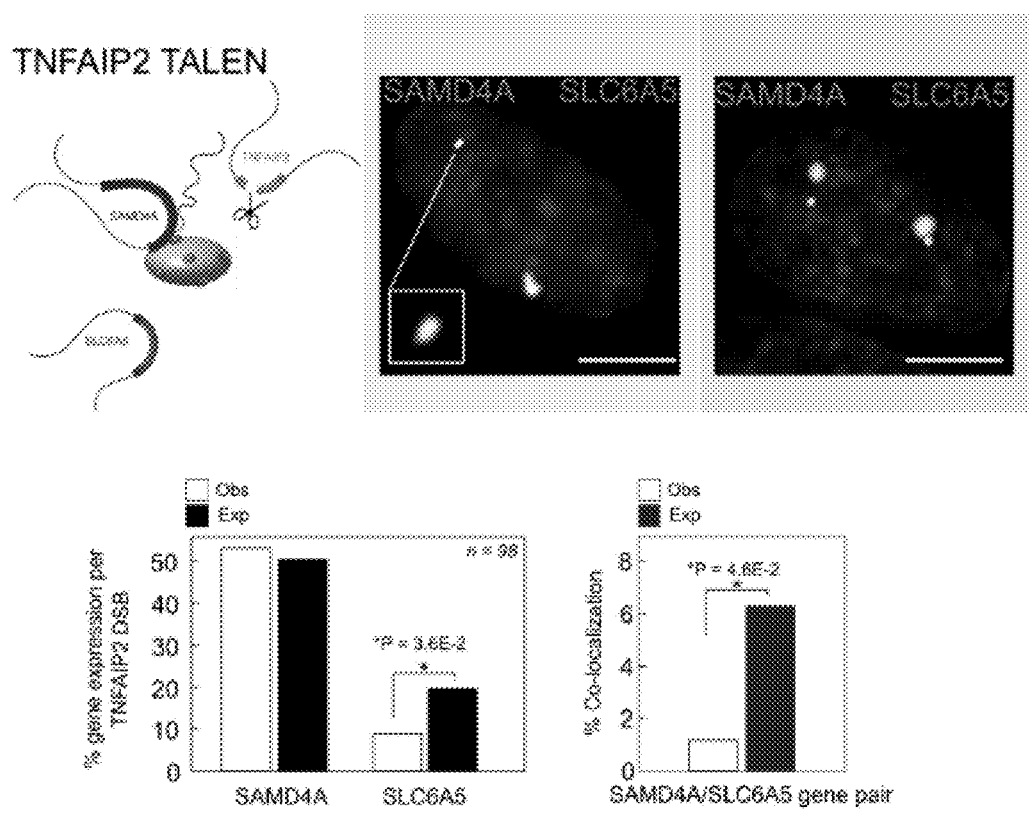
FIG. 26: TALEN-mediated disruption of a single gene loop and the associated chromosomal contacts in a multi-gene complex alters the transcriptional status of other genes occupying the same complex. Disruption of the TNFAIP2 gene loop does not affect SAMD4A gene expression, but alters SLC6A5 transcription and SAMD4A/SLC6A5 colo-calization.
Figure 33:
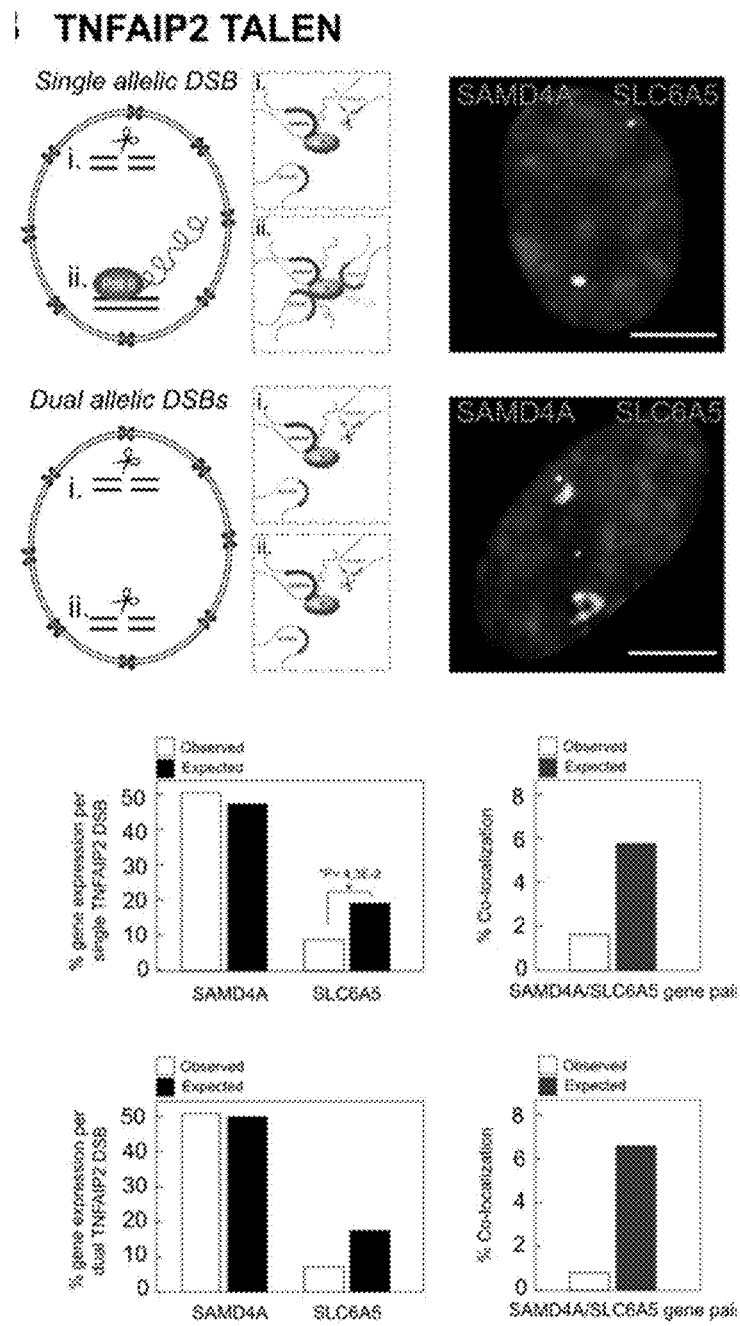
FIG. 33: Comparison between the phenotype in cells displaying a single allelic DSB to cells displaying dual allelic DSBs. In cells displaying single allelic TNFAIP2 TALEN-induced DSBs, SAMD4A transcription remained unaffected, whilst SLC6A5 transcription was limited to the intact TNFAIP2 allele. SLC6A5 transcription was rarely observed in cells harboring dual allelic DSBs, whereas SAMD4A transcription remained unaffected. There was a reduction in SAMD4A/SLC6A5 co-localization frequencies in both cells displaying single and dual allelic DSBs. Two-tailed Fisher exact test; *P<0.05, cells were counterstained with DAPI. Bar, 5 µm.
Figure 34:
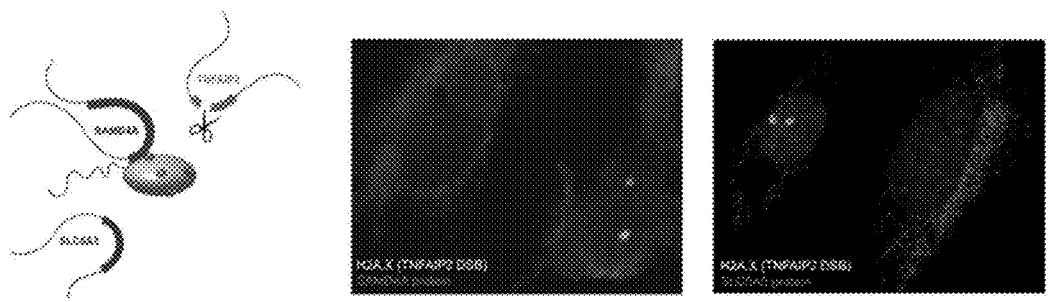
FIG. 34: TALEN-induced dual allelic DSBs abrogate protein expression of other members of the NF-kB multi-gene complex. Disrupting the TNFAIP2 gene loop is sufficient to abrogate SLC6A5, but not SAMD4A protein expression. Dual indirect immunofluorescence of SAMD4A or SLC6A5 and DSBs was performed using a donkey-anti rabbit antibody conjugated to Atto488 and donkey-anti-goat conjugated to Atto565 respectively. Cells displaying dual TNFAIP2-induced DSBs, as detected by H2A.X, displayed a reduction in protein expression of SLC6A5, whereas SAMD4A protein expression did not appear to be affected.
Figure 42:
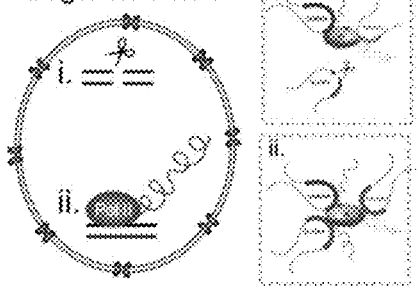
Figure 42:
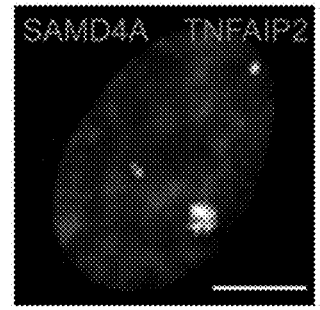
Figure 42:
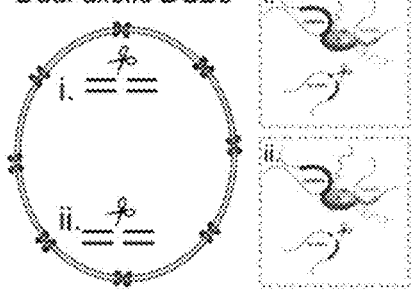
Figure 42:
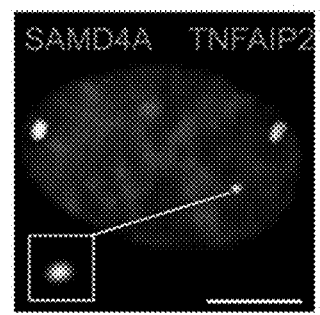
Figure 42:
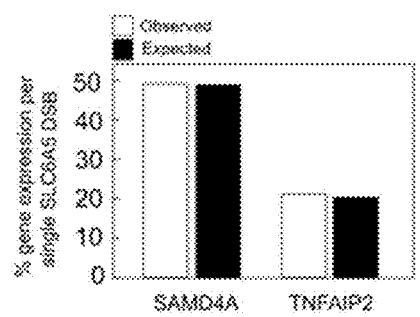
Figure 42:
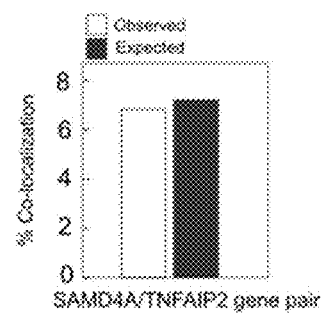
Figure 42:
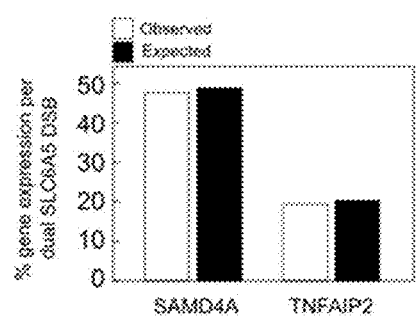
Figure 42:
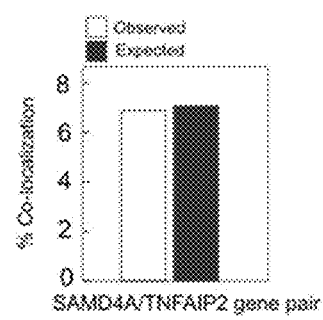
Figure 43:
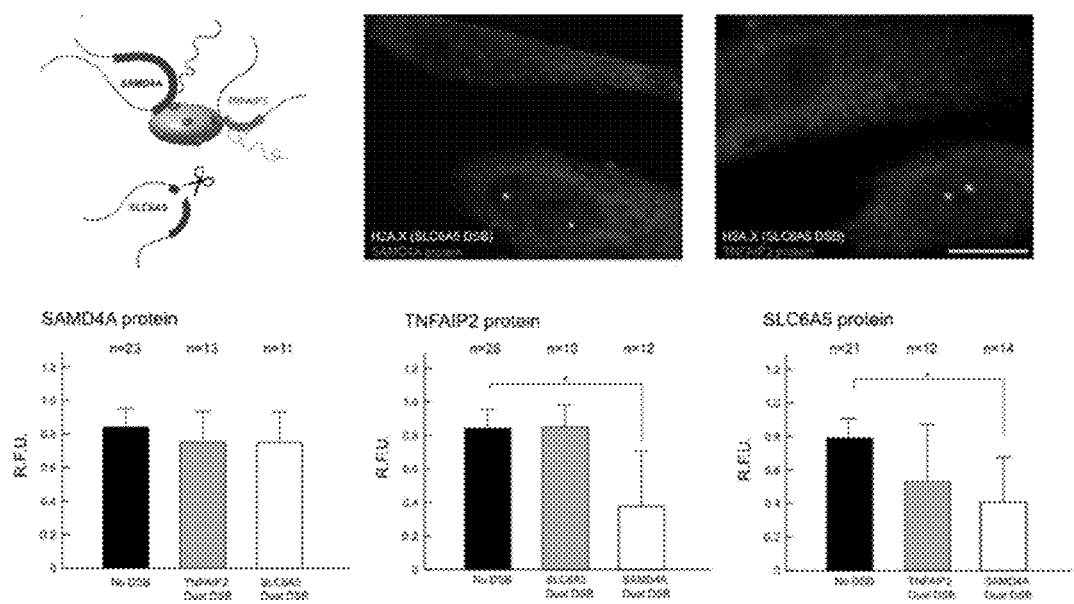
FIG. 43: TALEN-induced dual allelic DSBs abrogate protein expression of other members of the NF-kB multi-gene complex. Disrupting the SLC6A5 gene loop does not alter protein expression of SAMD4A or TNFAIP2. Dual indirect immunofluorescence of SAMD4A or TNFAIP2 and DSBs was performed using a donkey-anti rabbit antibody conjugated to Atto488 and donkey-anti-goat conjugated to Atto565 respectively. Cells displaying dual SLC6A5-induced DSBs, as detected by H2A.X, did not display any alteration in protein expression of TNFAIP2 and SLC6A5. R.F.U., relative fluorescent units, mean±SD, Mann Whitney U test, *P<0.05, cells were counterstained with DAPI, Bar, 5 µm.

Initially, a possible explanation for the transcriptional response observed in FIGS. 20, 22, 26 and 35 could be that the SAMD4A protein is required for the expression of TNFAIP2 and SLC6A5. However, microarray analysis demonstrates that it takes ~85 mins for RNA Pol II to transcribe the SAMD4A gene. The observed reduction in TNFAIP2 and SLC6A5 expression by the SAMD4A TALEN-induced DSB is observed 10 mins post TNFα stimulation (FIGS. 22 and 26). No transcription, or chromosomal contact, is observed between these co-regulated genes in unstimulated HUVECs (Papantonis et al., 2010). Therefore, these effects cannot be attributed to the entire SAMD4A transcript, or protein, as neither is present at the 10 mins time point. HUVECs are primary cells with defined chromosomal territories, and therefore always display two spatially distinct DNA FISH foci (FIG. 7). The comparison between cells harboring single allelic DSBs and dual allelic DSBs (FIG. 19) offers a unique perspective on the influence of protein expression in the assembly of the multigene complex. In cells displaying a single allelic break (disrupted SAMD4A transcription at one allele) the following is observed; reduced transcription of two other genes that interact with SAMD4A near to the TALEN-induced DSB (FIG. 23), and translation of SAMD4A protein, presumably from the intact allele (FIG. 19). The reduction of TNFAIP2 and SLC6A5 transcription was also observed in cells harboring dual allelic DBSs for SAMD4A (FIG. 23). Cells displaying dual allelic SAMD4A TALEN induced DSBs also have reduced protein expression (FIG. 19). Collectively, these data clearly show that the protein product of the SAMD4A gene is not required for the expression of TNFAIP2 and SLC6A5. Currently, no other biochemical technique offers the same insight.) Supporting the observed reduction in transcription at single allelic DSBs, in cells where both SAMD4A alleles were targeted, virtually all transcription from TNFAIP2 and SLC6A5 was lost at both alleles (FIGS. 23, 33 and 42). Furthermore, protein levels of TNFAIP2 and SLC6A5 were also severely reduced, as assessed by IF, in cells where both SAMD4A alleles were successfully targeted (FIGS. 24, 34 and 43). Hence, in a manner analogous to GREB1 (Li et al., 2012), SAMD4A appeared to be influencing the transcription of other co-regulated and interacting genes within the same multigene complex.

Figure 25:
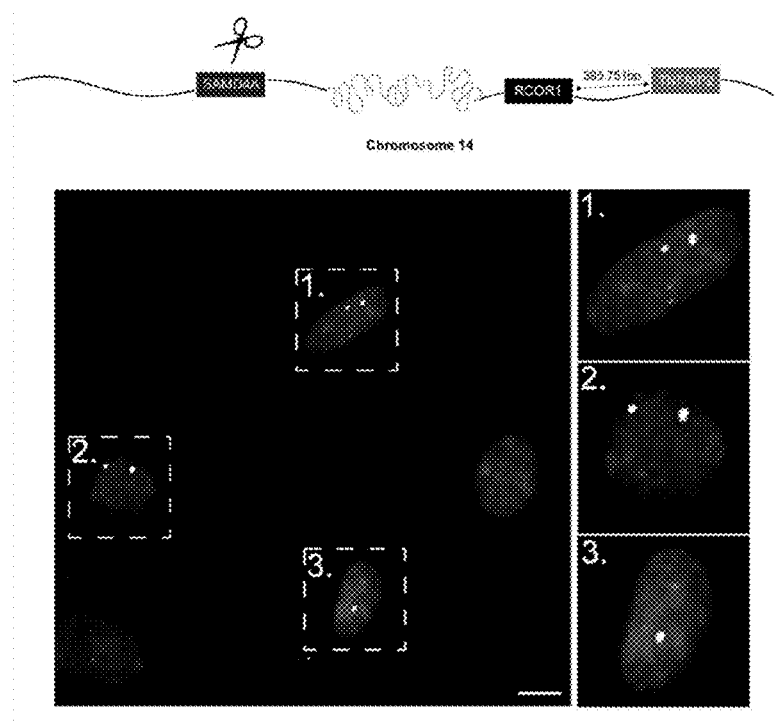
FIG. 25: The SAMD4A TALEN does affect the transcriptional status of RCOR1. RCOR1, a gene with transcriptional activity comparable to GAPDH, located approximately 400 kb 5' of TNFAIP2 was unaffected by the SAMD4A TALEN. Two foci of RCOR1 are evident in each cell in the field of view. Cells were counterstained with DAPI. Bar, 10 μm

We sought to determine whether the loss of transcription of TNFAIP2 was due to the DSB abrogating the transcription of genes located between SAMD4A and TNFAIP2, on chromosome 14. RCOR1 is a gene located 400 kb 5' of TNFAIP2 and displays transcriptional activity comparable to GAPDH (Papantonis et al., 2012). We repeated the TALEN-mediated disruption of SAMD4A gene loop whilst monitoring transcription of RCOR1 (FIG. 25). Transcription remained unaffected at the RCOR1 locus (FIG. 25). This observation concurred with the hypothesis that loop-mediated chromosomal contact of SAMD4A specifically impacts the transcription of other members of the multigene complex but has no effect on genes outside of the complex. This extended to genes on the same chromosome that were interspersed between two genes in the multigene complex.

Figure 27:
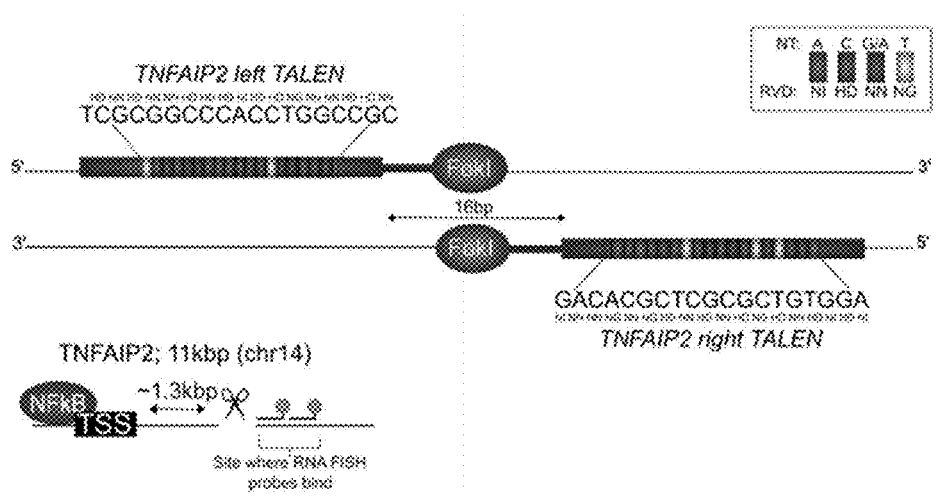
FIG. 27: TALEN-mediated disruption of the TNFAIP2 gene loop abrogates TNFAIP2 gene expression. The TNFAIP2 TALEN targets the approximate region in intron 2 involved in chromosomal contact at 10 mins post TNFα stimulation. Left and right TALENs were designed to contain 18 full monomer repeats and target a 20 bp target region, where the first and last space specify the T at the N terminus and the 0.5 repeat respectively.
Figure 28:
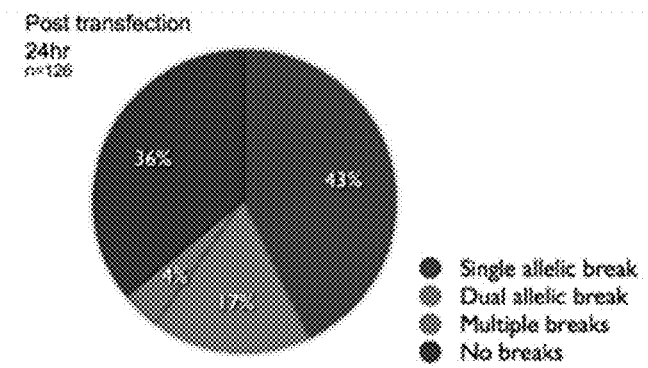
FIG. 28: TALEN-mediated disruption of the TNFAIP2 gene loop abrogates TNFAIP2 gene expression. Post 24 hr transfection, ~60% of cells displayed TNFAIP2 TALEN-induced DSBs and low levels of apoptotic cells, as evidenced by cells displaying multiple breaks (more than 2). A higher portion of transfected cells displayed single allelic DSBs as opposed to dual allelic DSBs.
Figure 29:
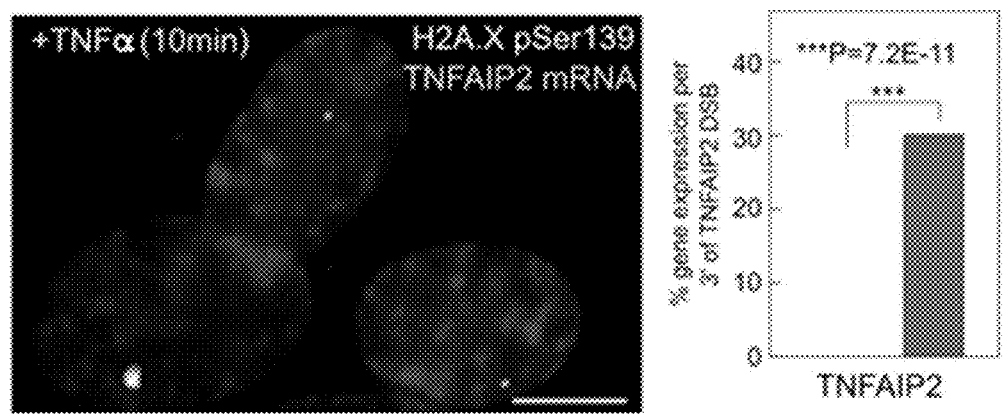
FIG. 29: TALEN-mediated disruption of the TNFAIP2 gene loop abrogates TNFAIP2 gene expression. The TNFAIP2 TALEN abrogates transcription downstream of the DSB. Dual-transfected HUVECs were stimulated with TNFα for 10 mins to allow for the first ~1.5 kbp of the TNFAIP2 to be transcribed. Nascent intronic TNFAIP2 RNA (Atto565) transcribed downstream of the DSB (H2A.X-Atto488) was never observed. Two-tailed Fisher exact test; ***P<0.001. Cells were counterstained with DAPI. Bar, 5 μm.
Figure 30:
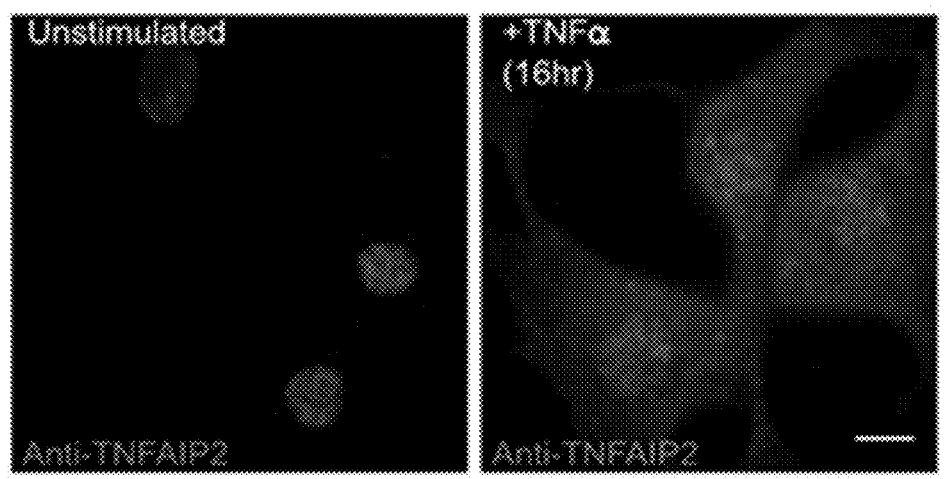
FIG. 30: TALEN-mediated disruption of the TNFAIP2 gene loop abrogates TNFAIP2 gene expression. TNFα induces TNFAIP2 protein expression 16 hr post stimulation. Cells were counterstained with DAPI. Bar, 5 μm.
Figure 31:
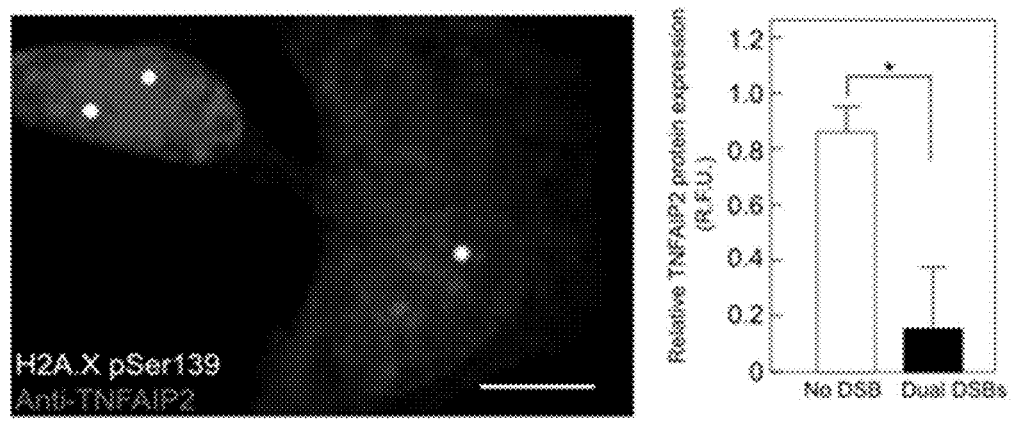
FIG. 31: TALEN-mediated disruption of the TNFAIP2 gene loop abrogates TNFAIP2 gene expression. Disrupting the TNFAIP2 gene loop is sufficient to abrogate protein expression. Dual indirect immunofluorescence of TNFAIP2 and H2A.X (DSBs) was performed using a donkey-anti rabbit antibody conjugated to Atto488 and donkey-anti-goat conjugated to Atto565 respectively. DSBs, as detected by H2A.X, displayed a severe reduction in protein expression. R.F.U., relative fluorescent units, mean±SD, **P<0.01, Two-tailed unpaired Students t test, cells were counter-stained with DAPI, Bar, 5 μm.
Figure 32:
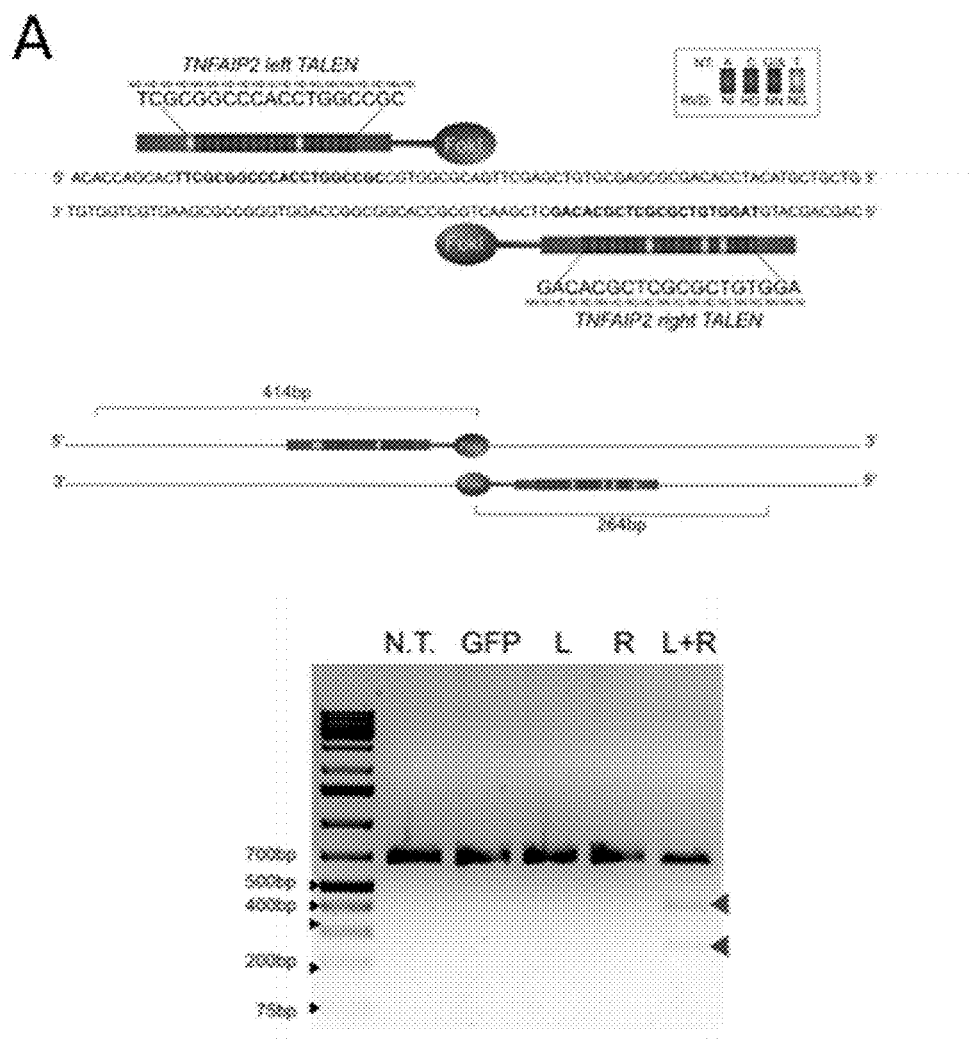
FIG. 32: Detection of TALEN efficiency. Gel showing the surveyor nuclease result from the TNFAIP2 TALEN pair. NT, control from un-transfected cells; GFP, cells transfected with GFP; L, TNFAIP2 left TALEN only; R, TNFAIP2 right TALEN only; L+R, cells transfected with the pcDNA left and right TNFAIP2 TALENs.
Figure 35:
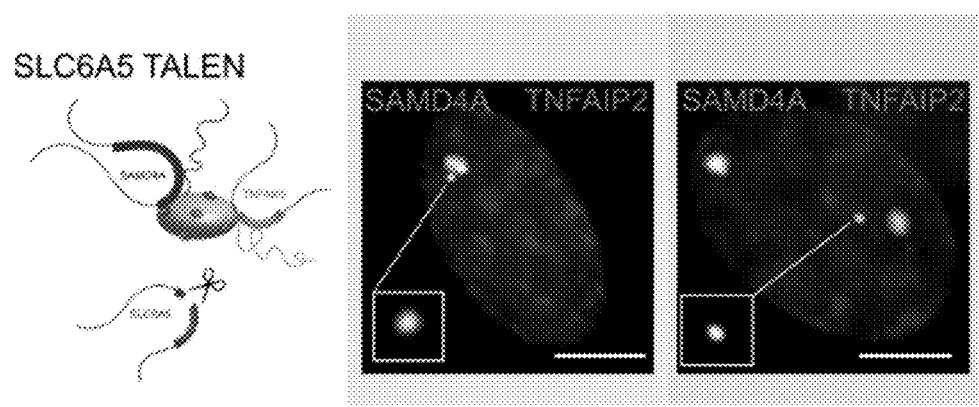
FIG. 35: TALEN-mediated disruption of a single gene loop and the associated chromosomal contacts in a multi-gene complex alters the transcriptional status of other genes occupying the same complex. Disruption of the SLC6A5 gene loop does not alter SAMD4A/TNFAIP2 transcription or co-localization. Two-tailed Fisher exact test; *P<0.05, P<0.01, *P<0.001, n, number of DSBs. Cells were counterstained with DAPI. Bar, 5 µm. See also
Figure 35:
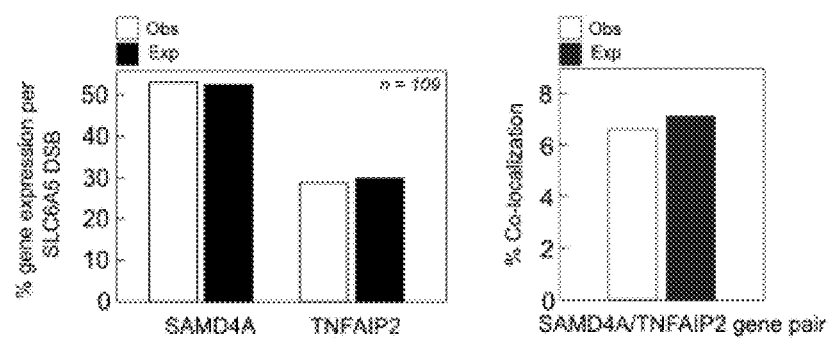
Figure 36:
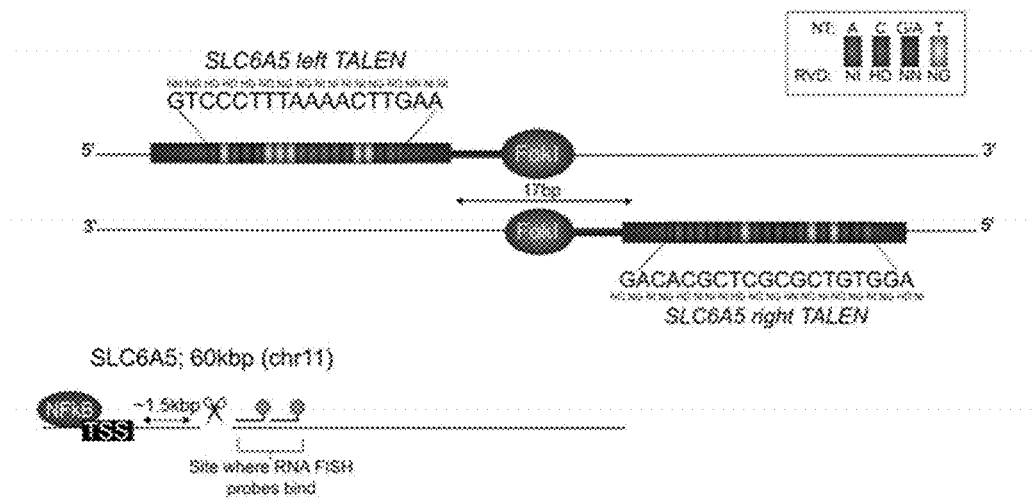
Figure 37:
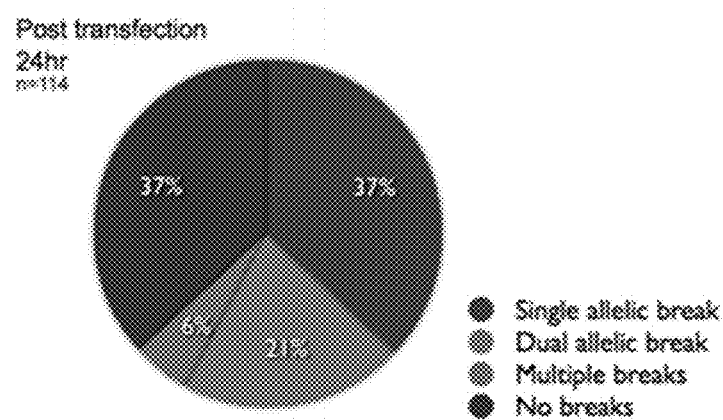
Figure 38:
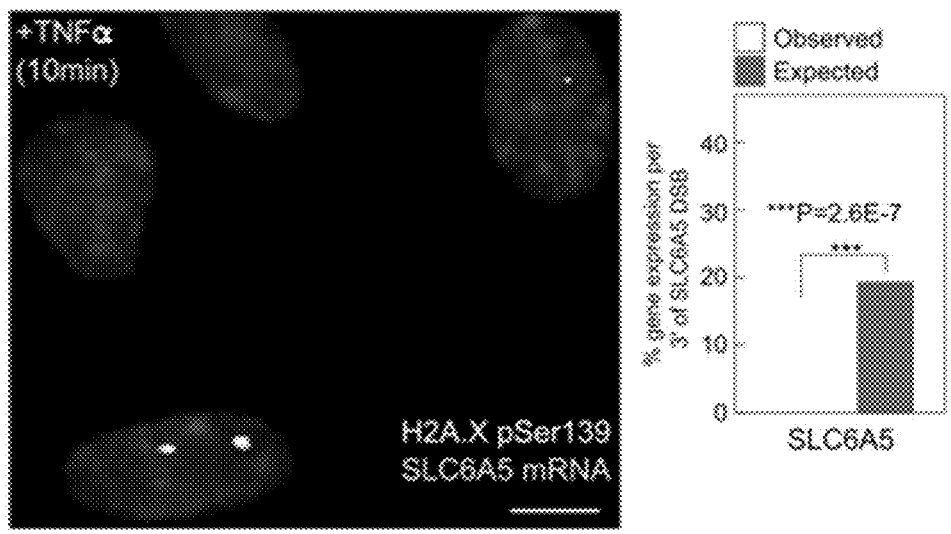
Figure 39:
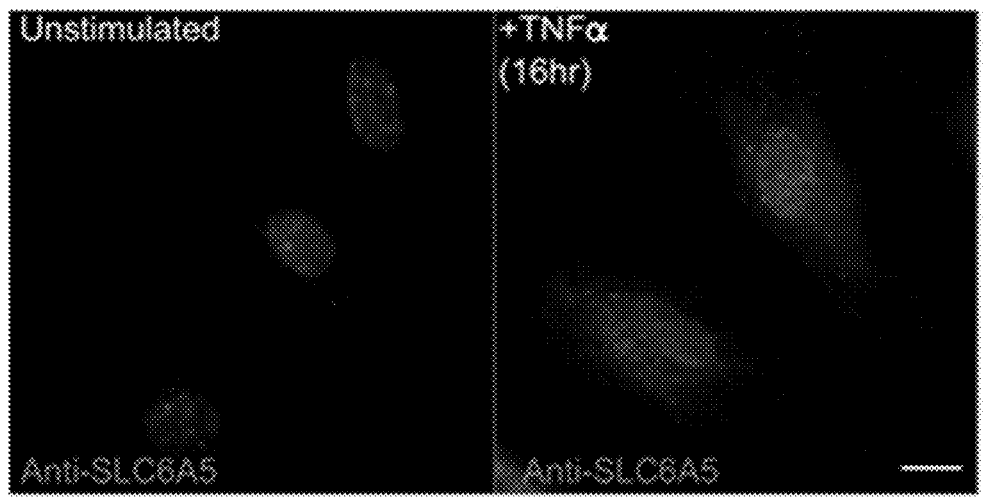
Figure 40:
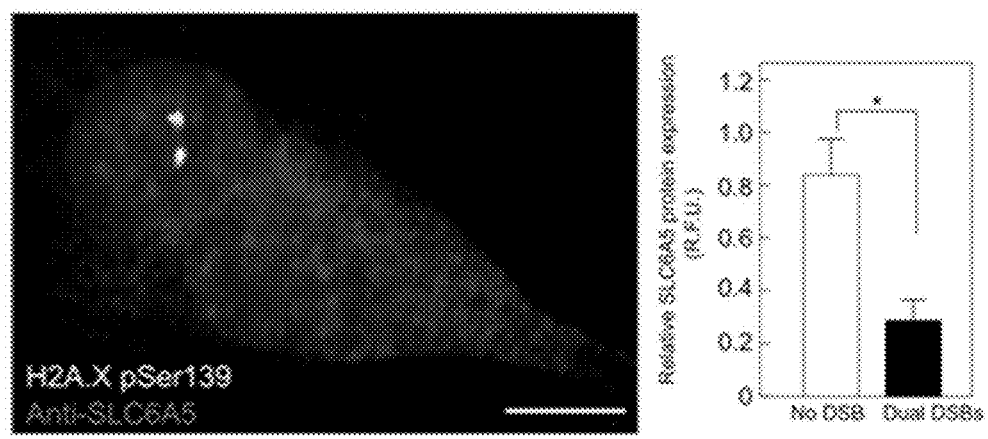
Figure 41:
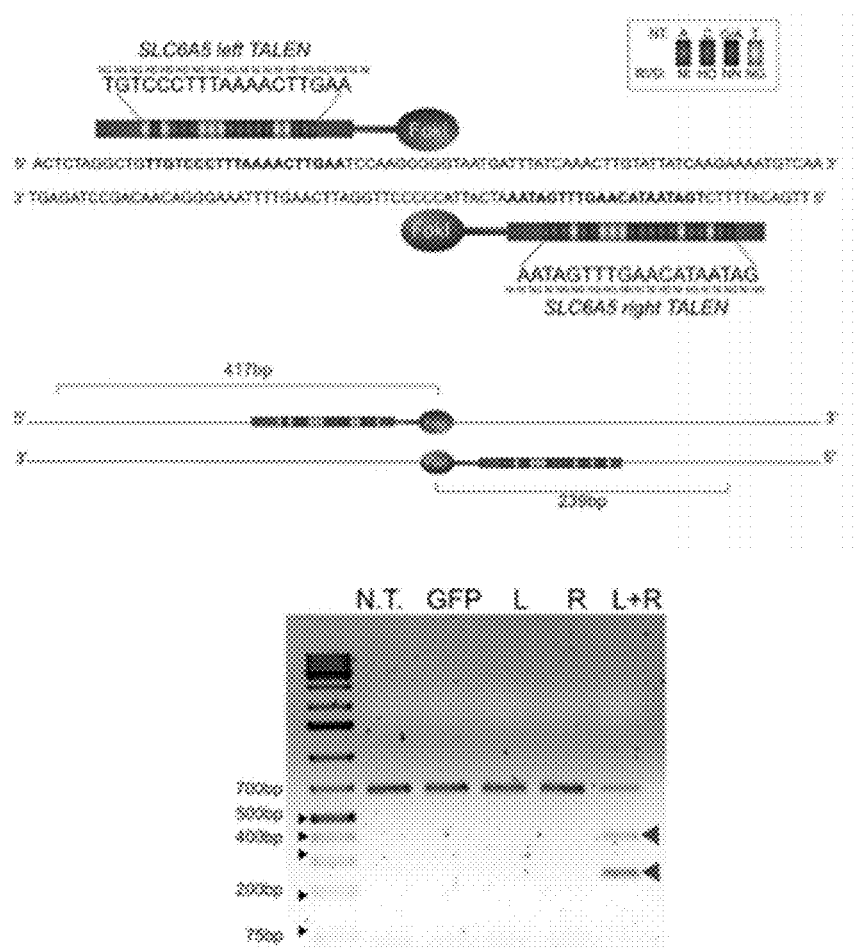
FIG. 41: Detection of TALEN efficiency. Gel showing the surveyor nuclease result from the SLC6A5 TALEN pair. NT, control from un-transfected cells; GFP, cells transfected with GFP; L, SLC6A5 left TALEN only; R, SLC6A5 right TALEN only; L+R, cells transfected with the SLC6A5 pcDNA left and right TALENs.

We sought to determine whether the presence of other gene loops in the multigene complex were equally required for co-transcription, since all genes in the multigene complex were bound by the NF-κB transcription factor (Papantonis et al., 2010). We hypothesized that if gene loops were equally required for co-transcription, then the disruption of any other gene loop would have a similar effect to that observed for SAMD4A. Alternatively, an asymmetrical relationship between gene loops infers that the disruption of one gene loop may have no bearing on the transcriptional status of other genes in the complex. To differentiate between these two hypotheses we designed TALENs targeted to TNFAIP2 (FIGS. 27, 28, 29, 30 and 31) and SLC6A5 (FIGS. 36, 37, 38, 39 and 40). The sites for these TALENs were identified by 3C (Papantonis et al., 2010) indicating where the chromosomal contacts occurred between these genes. Using an identical approach to our initial assay, we delivered a TALEN to TNFAIP2 whilst monitoring transcription of SAMD4A and SLC6A5. The TNFAIP2 TALEN targets the site of chromosomal contact (~1.5 kbp downstream of the TSS), whilst our RNA FISH probes interrogated a region downstream of this site (FIG. 27). Remarkably, we observed that the disruption of the TNFAIP2 loop had no significant effect on SAMD4A transcription, yet transcription of both TNFAIP2 (FIG. 29) and SLC6A5 was reduced (FIG. 26). Transcriptional loss was observed at either a single or both targeted alleles (FIG. 33). When we repeated the experiment with a TALEN targeting the SLC6A5 gene loop on chromosome 11 (FIG. 36), the hierarchical effect was more pronounced with transcription unaffected in both SAMD4A and TNFAIP2 (FIG. 35 and FIG. 42). However at all successfully targeted single and dual alleles of SLC6A5, transcription was lost (FIG. 38). This result lends credence to the hypothesis that the disrupted site of chromosomal contact precludes the ability of the gene loop to access critical transcriptional machinery due to a requirement for loop-mediated chromosomal contacts. This unique single cell perspective reveals a highly unexpected hierarchical organization within the TNFα-induced multigene complex, providing the first direct evidence that chromosomal contacts play a central role in supporting transcription and determining the hierarchy.

Disrupted SAMD4A Gene Loops can be Successfully Repaired

Figure 44:
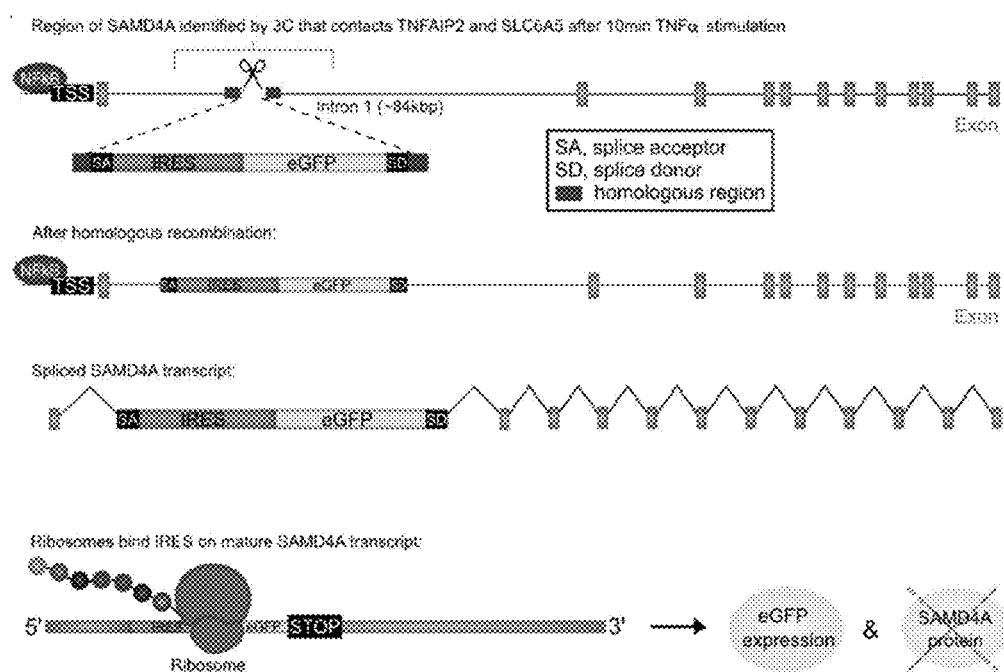
FIG. 44: The SAMD4A gene loop was successfully repaired. Graphical representation of the repair strategy. The repair construct consists of an IRES and eGFP, flanked by splice sites.
Figure 45:
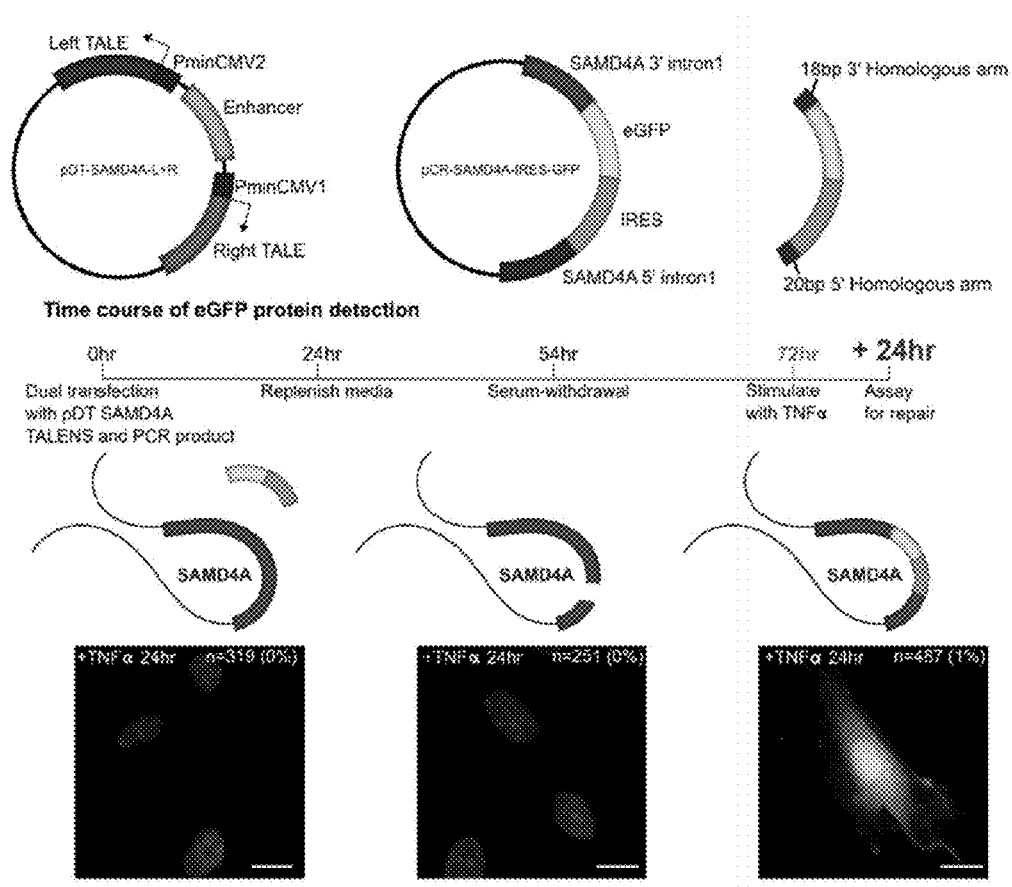
FIG. 45: The SAMD4A gene loop was successfully repaired. TNFα-induced activation of SAMD4A induces eGFP expression. eGFP signal was observed in ~1% of HUVECs dual transfected with the pDT vector and PCR product for 72 hr and stimulated with TNFα for 24 hr. Cells were counterstained with DAPI. n, number of cells. Bar, 5 µm. See also FIGS. 46 and 47.
Figure 46:
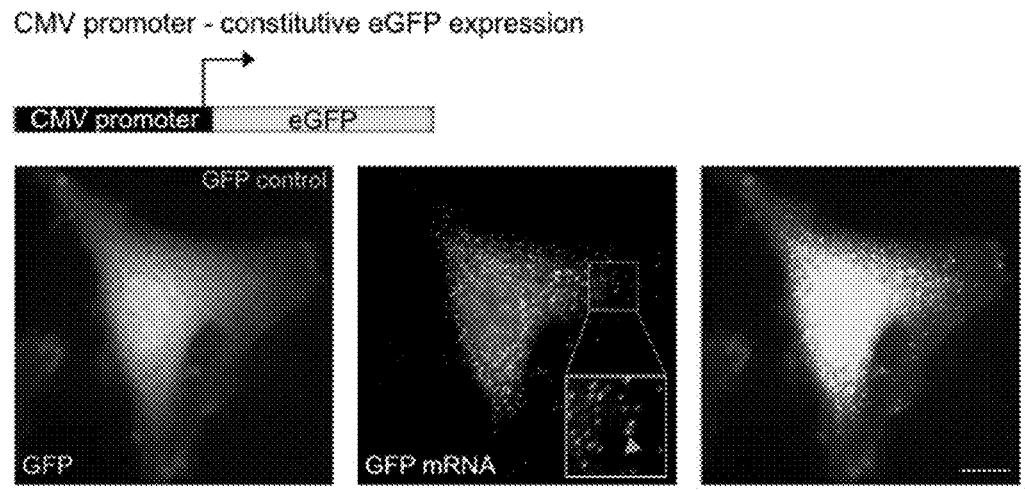
FIG. 46: The SAMD4A gene loop was successfully repaired with the IRES-GFP construct. HUVECs were transfected with a CMV-eGFP construct. eGFP positive or 'green' cells coincided with a large number of RNA FISH foci.
Figure 47:
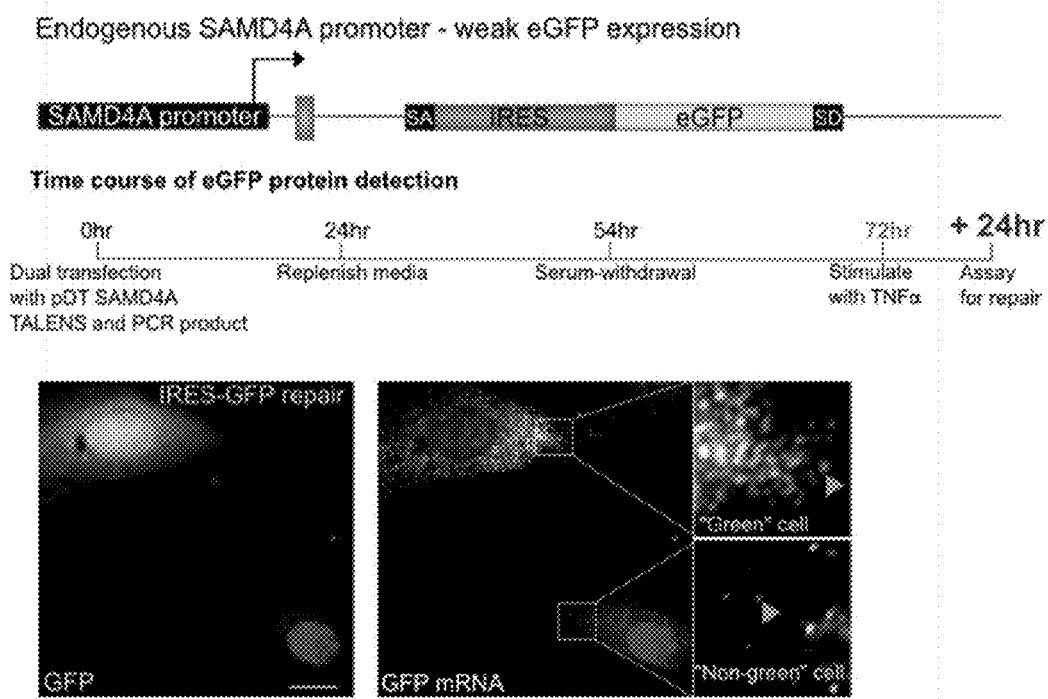
FIG. 47: The SAMD4A gene loop was successfully repaired with the IRES-GFP construct. The SAMD4A promoter does not constitutively express the IRES-eGFP mRNA. eGFP signal was observed in ~1% of HUVECs dual transfected with the pDT vector and PCR product for 72 hr and stimulated with TNFα for 24 hr. ~90% of cells displaying eGFP mRNA transcripts were not visualized as a 'green' cell. Cells were counterstained with DAPI. Bar 10 µm.

If the integrity of the gene loop topology and chromosomal contacts were essential for co-transcription, then we hypothesized that restoring the chromosomal contacts would restore transcription of interacting genes in the multigene complex. DSBs are generally repaired in most cells by two highly conserved mechanisms: rapid but error-prone non-homologous end joining (NHEJ), or the slower, but highly precise, homology-directed repair (HDR). We generated a repair construct designed to span the SAMD4A TALEN target site, to exploit HDR to restore SAMD4A gene loop integrity by inserting an exonic eGFP sequence into intron 1 of SAMD4A (FIG. 44). We included an internal ribosome entry sequence (IRES), as well as splice sites flanking the IRES-eGFP, to facilitate the co-transcriptional splicing and independent translation of the repair construct (FIG. 44). Once repaired, through the activation of SAMD4A, TNFα stimulation would then be able to induce SAMD4A/IRES-eGFP transcription. We used the identification of eGFP positive cells to establish a time course for TNFα treatment. Due to HDR being rare, and as the IRES-eGFP is under the control of the endogenous SAMD4A promoter, we sought to enhance the efficiency of the repair. We constructed a novel bidirectional TALEN system able to combine both targeting arms of the TALEN into a single bi-directional promoter plasmid (pDT; FIG. 45), to ensure that equimolar quantities of both left and right TALENs were synthesized in the same cell throughout the DSB-induction process. HUVECs dual transfected with the pDT and the repair plasmids demonstrated poor repair efficiency in the transfected cells as evidenced by the lack of eGFP signal (data not shown). To modify the repair construct, we amplified the IRES-eGFP sequence with associated flanking splice sites and included short 5' 20 bp and 3' 18 bp homologous extensions on either side of the SAMD4A DSB to induce efficient HDR (FIG. 45). Notably, eGFP protein signal was observed in ~1% of HUVECs dual transfected with the pDT plasmid and PCR product for 72 hr and stimulated with TNFα for 24 hr (FIG. 45). However, eGFP mRNA transcripts, which can only arise following successful HDR, were observed in ~10% of cells in the population (FIGS. 46 and 47). Notably, eGFP positive or 'green' cells coincided with a large number of RNA FISH foci (FIGS. 46 and 47). As the SAMD4A promoter does not constitutively express the IRES-eGFP mRNA, it is reasonable that very few cells in the population would transcribe sufficient IRES-eGFP mRNA to enable the detection of a 'green' cell. Therefore, detection of IRES-eGFP mRNA was the more sensitive approach to identifying successful HDR and was used to interrogate the effects of a repaired gene loop.

Figure 48:
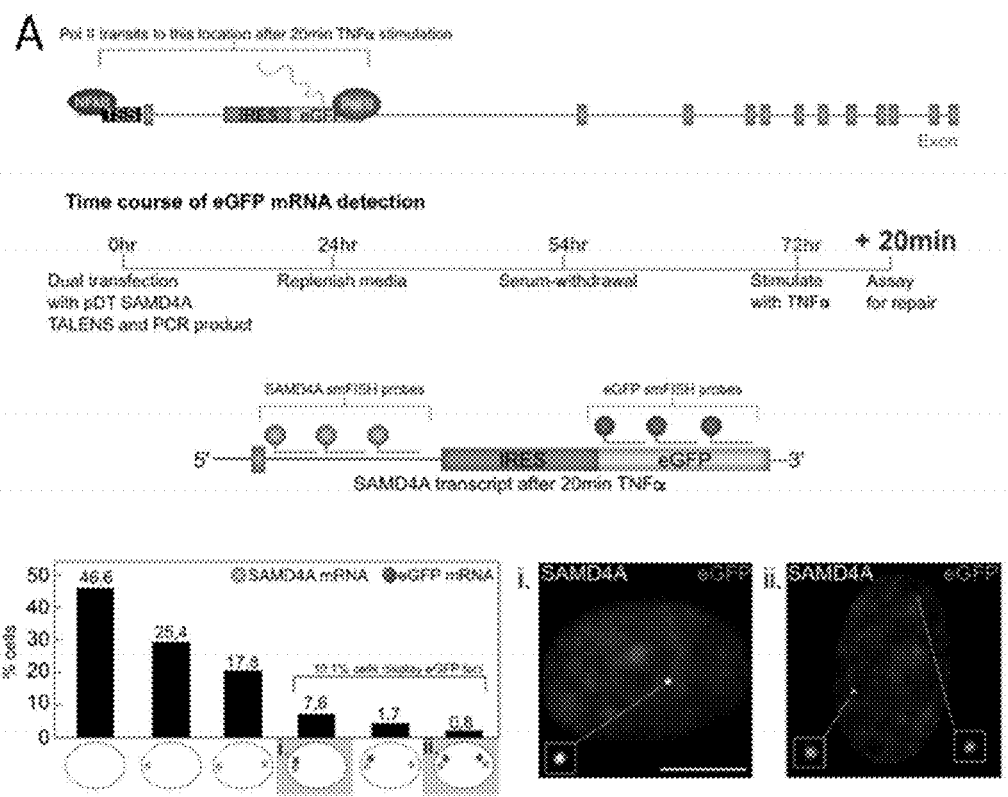
FIG. 48: Repairing the disrupted SAMD4A gene loop restores transcription of genes in a multigene complex. HUVECs were stimulated for 20 min with TNFα, recapitulating transcription of the first ~1.5 kbp of SAMD4A as well as the IRES-eGFP. Distinct eGFP foci were evident in ~10% of transfected cells, and these foci overlapped with SAMD4A mRNA. n, number of cells (n=118), Bar, 5 µm.
Figure 49:
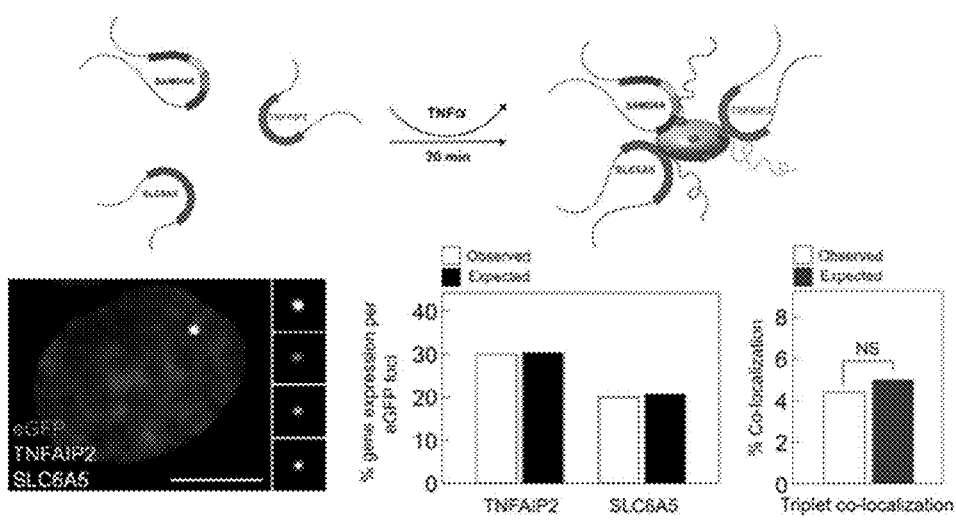
FIG. 49: Repairing the disrupted SAMD4A gene loop restores transcription of genes in a multigene complex. There was no significant difference in the co-localization frequencies between eGFP/SAMD4A, TNFAIP2 and SLC6A5 and mock-transfected cells. Cells were counterstained with DAPI. N, number of cells (N=448), n, number of eGFP foci (n=45), NS, no significant difference, Bar, 5 µm.

Restoration of the SAMD4A Gene Loop Restores Transcription of Interacting Members in a Sequence-Independent Manner Satisfied that the repair experiment was fully functional, we sought to investigate whether the re-establishment of contact was sufficient to restore transcription of interacting genes. We stimulated HUVECs for 20 mins with TNFα, recapitulating transcription of the first ~1.5 kbp of SAMD4A and IRESeGFP. We detected transcription of eGFP using RNA FISH probes binding to its RNA (FIGS. 46 and 47), and related the position of eGFP transcription to members of the multigene complex. Distinct eGFP foci were evident in ~10% of transfected cells and these foci overlapped with SAMD4A intronic mRNA (FIG. 48). In the instances where we had successful HDR mediated repair, we observed no change in the transcription of any of TNFAIP2 and SLC6A5 relative to the normal TNFα-induced transcriptional response (FIG. 49). Moreover, there was no significant difference in the co-localization frequencies between eGFP/SAMD4A, TNFAIP2 and SLC6A5 in the repaired and mock-transfected cells (FIG. 49). This result indicates that reestablishment of an intact SAMD4A loop, in a sequenceindependent manner, restores chromosomal contacts as well as transcription of TNFAIP2 and SLC6A5 in this multigene complex.

EXAMPLE 2

Disrupting the IL8 Enhancer Abroagtes IL8 Expression

Recently, Hi-C studies revealed that the pro-inflammatory chemokines CC Chr.17 (CCL2, CCL7, CCL11) and CXC Chr.4 (IL8, CXCL1, CXCL3, CXCL2) are organized into TADs and engage in chromosomal contact.

Using intronic smFISH, we were able to show that the CXC chemokines are only induced following TNF induction. Furthermore, the smFISH foci of co-expressed CXC genes always co-localize.

Deeper bioinformatic analysis of both Hi-C and ChIA-PET data in the CC and CXC TADs identified a large cluster of transcriptional enhancers. At the 5' end of the CXC TAD, we identified a putative 'super-enhancer' region, spanning ~80 kb and forming extensive chromosomal contacts with the proinflammatory genes (unpublished data). Typically, such regions are densely occupied by chromatin regulators over tens of kb. Accordingly, this region is highly enriched for eRNA chromatin marks, H3K4me1 and H3K27Ac. Using the recently published 'eRNA encyclopedia', we identified several eRNAs transcribed from this region in a tissue- and cell-specific manner. Using smFISH, we were able to detect some of these eRNAs across different primary cell types and observed different expression patterns (unpublished data).

Through their interaction with the mediator complex, eRNAs have been proposed to be the architects of chromatin organization and therefore putatively TADs. We found that depleting Mediator 12 (Med12) abrogates the expression of all the CXC cytokines. We designed TALENs to induce a DSB at various sites within the superenhancer region that was established by ChIA-PET to engage in contact. In one instance the DSB was induced at the site of an eRNA. The DSB, or site of disruption, was detected by immunofluorescent staining of H2A.X pSer139, a factor of the DSB repair process. In parallel to the detection of the DSB, transcriptional activity of interacting genes in the multigene complex was determined using intronic RNA FISH. We observed that perturbing the superenhancer in the CXC TAD silenced all of the pro-inflammatory CXC genes (IL8, CXCL2, CXCL1 and CXCL3).

EXAMPLE 3

Figure 52:
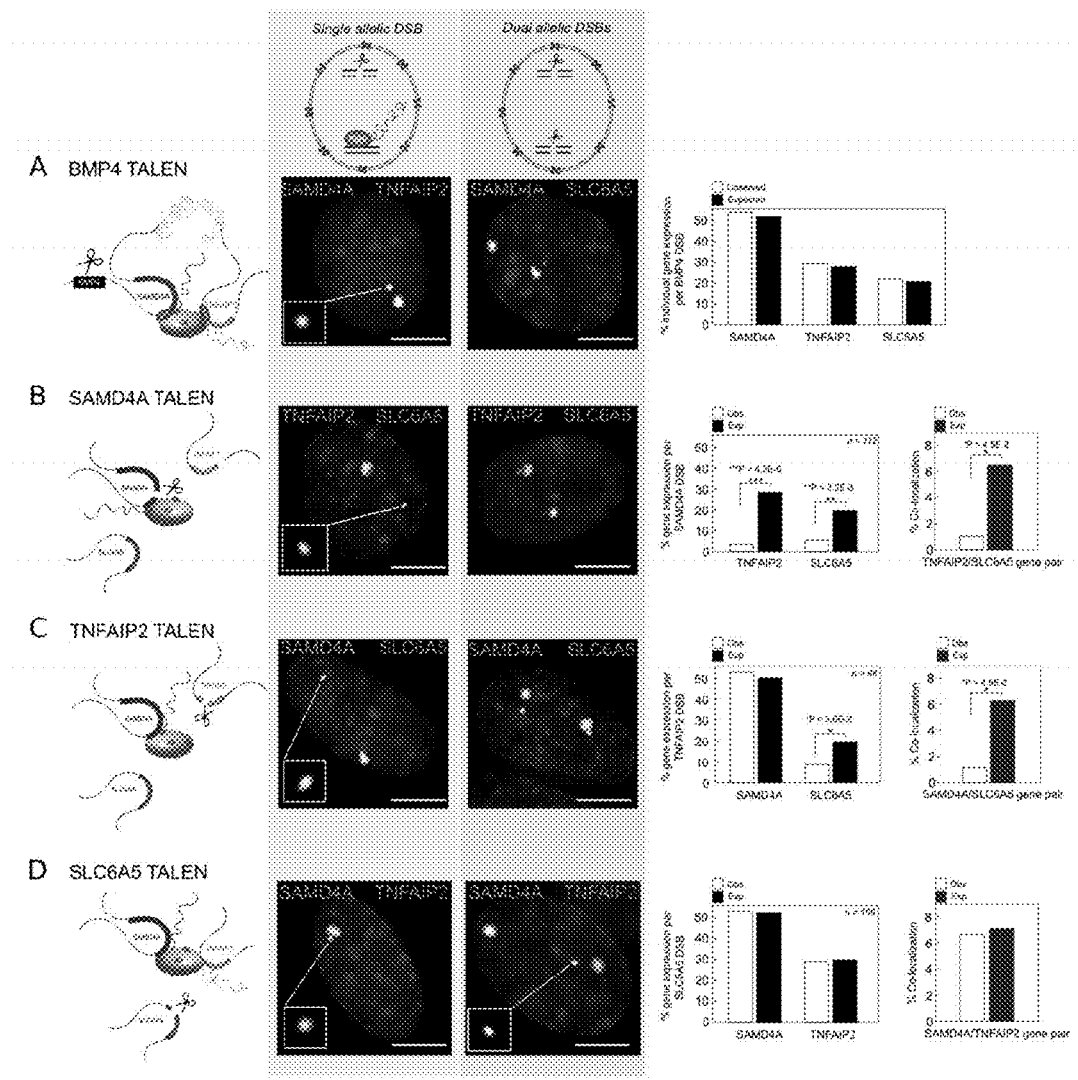
FIG. 52: TALEN-mediated disruption of a single gene loop and the associated chromosomal contacts in a multigene complex alters the transcriptional status of other genes occupying the same complex. (A) A DSB induced in the non-TNFα responsive gene, BMP4, did not alter transcription of SAMD4A, TNFAIP2 or SLC6A5 relative to the normal TNFα response. (B) The disruption of the SAMD4A gene loop abrogates TNFAIP2 and SLC6A5 transcription and co-localization. SAMD4A loop disruption detected by H2A.X was simultaneously monitored with transcription of TNFAIP2 and SLC6A5 by RNA FISH. (C) Disruption of the TNFAIP2 gene loop does not affect SAMD4A gene expression, but alters SLC6A5 transcription and SAMD4A/SLC6A5 co-localization. (D) Disruption of the SLC6A5 gene loop does not alter SAMD4A/TNFAIP2 transcription or co-localization. Two-tailed Fisher exact test; *P<0.05, P<0.01, *P<0.001, n, number of DSBs. Cells were counterstained with DAPI. Bar, 5 µm.

Disrupting Intra- or Interchromosomal Contact in Multigene Complexes Abrogates the Transcription of Interacting Genes (See FIG. 52)

TNFα, a major proinflammatory cytokine, is a stimulus that induces the coordinated assembly of coregulated genes in NF-κB-dependent multigene complexes (Papantonis et al., 2012). SAMD4A, a ~221 Kb gene on chromosome 14, is rapidly switched on by TNFα in primary human umbilical vein endothelial cells (HUVEC). 4C analysis reveals that prior to stimulation with TNFα, SAMD4A seldom interacts with other genes.

After activation by TNFα, SAMD4A interacts with multiple coregulated genes to form a multigene complex. TNFAIP2, a gene located on the same chromosome but ~50 Mb downstream, and SLC6A5 on chromosome 11, are two well-characterized interacting partners of SAMD4A. siRNA approaches cannot be utilized to interrogate loop-mediated dynamics in the SAMD4A/TNFAIP2/SLC6A5 multigene complex, as all three genes are activated by the same transcription factor. This exposes the necessity to develop functional assays able to discretely alter gene loop topology, without the global ablation of transcriptional regulators.

We used TALENs to discretely perturb sites within gene loops that are established to engage in chromosomal contact in the well-characterized NF-κB-regulated multigene complex (Papantonis et al., 2010).

Using the TALEN single cell assay, we observed that perturbing the SAMD4A gene loop did not alter transcription 5' of the DSB. However, consistent with other studies, we observed silencing of SAMD4A transcription 3' of the DSB. Intriguingly, despite occupying distal genomic locations, the transcription of TNFAIP2 and SLC6A5 were also significantly reduced (FIG. 52(I)). Further, the effect on co-transcription was hierarchical, with the disruption of TNFAIP2 altering SLC6A5 expression, but having no influence on SAMD4A (FIG. 52(II)), whereas perturbing SLC6A5 did not influence SAMD4A or TNFAIP2 transcription (FIG. 52(III)). This suggests a hierarchical assembly between these three genes, whereby TNFAIP2 'collects' RNA Pol II from SAMD4A, which are then able to recruit SLC6A5 to the multigene complex.

EXAMPLE 4

Perturbing CTCF Sites Flanking TNFAIP2 Abrogates Transcription

Figure 53:
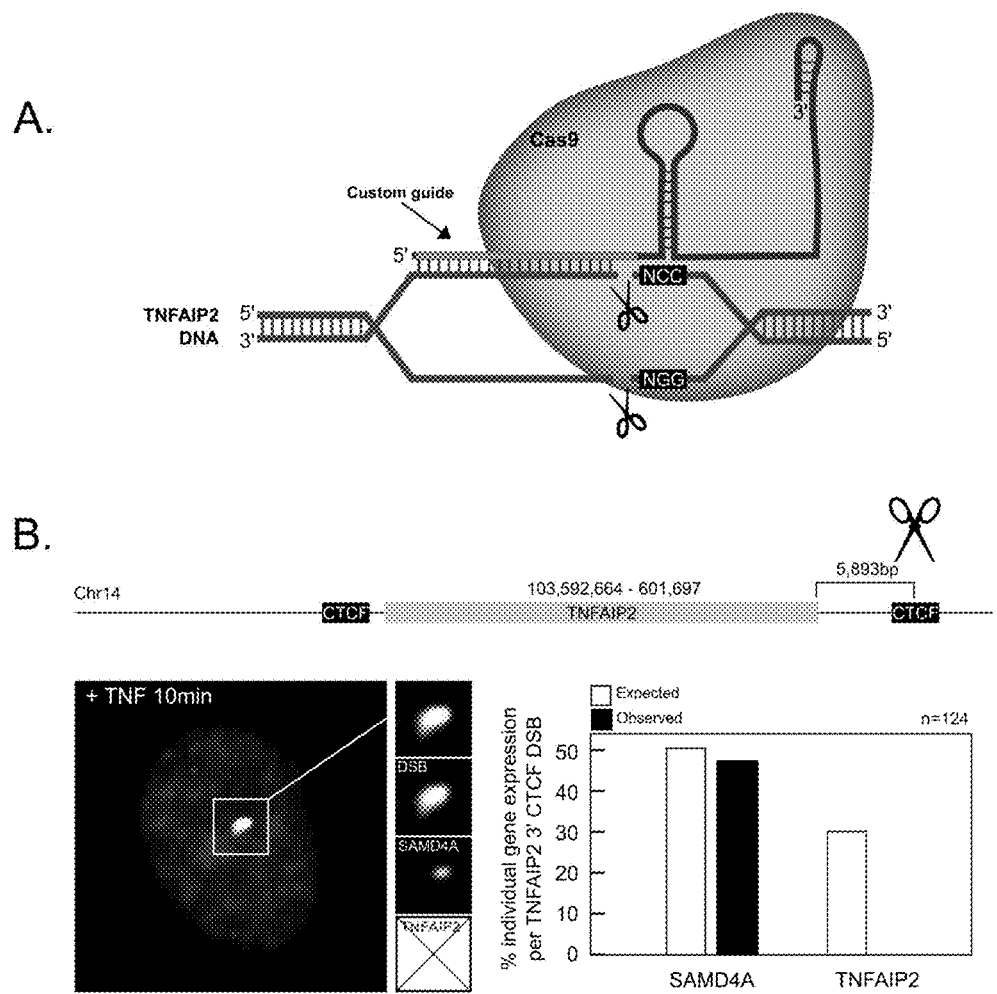
FIG. 53: Disrupting the CTCF site 3' of the TNFAIP2 gene abrogates transcription of TNFAIP2. (A) A CRISPR was designed to induce a DSB in the the consensus CTCF site located 3' of the TNFAIP2 gene. (B) The disruption of the 3' CTCF site was detected by H2A.X was simultaneously monitored with transcription of TNFAIP2 by RNA FISH. Two-tailed Fisher exact test; *P<0.05, P<0.01, *P<0.001, n, number of DSBs. Cells were counterstained with DAPI. Bar, 5 µm.

CTCF, binds to consensus sites that frequently flank genes. TNFAIP2, a ~11 Kb gene on chromosome 14, is flanked by CTCF consensus binding sites. We used CRISPRs to discretely perturb sites within CTCF consensus binding site (FIG. 53). We observed that perturbing the 3' CTCF binding site with a DSB in the silenced the expression of TNFAIP2.

Discussion

Figure 50:
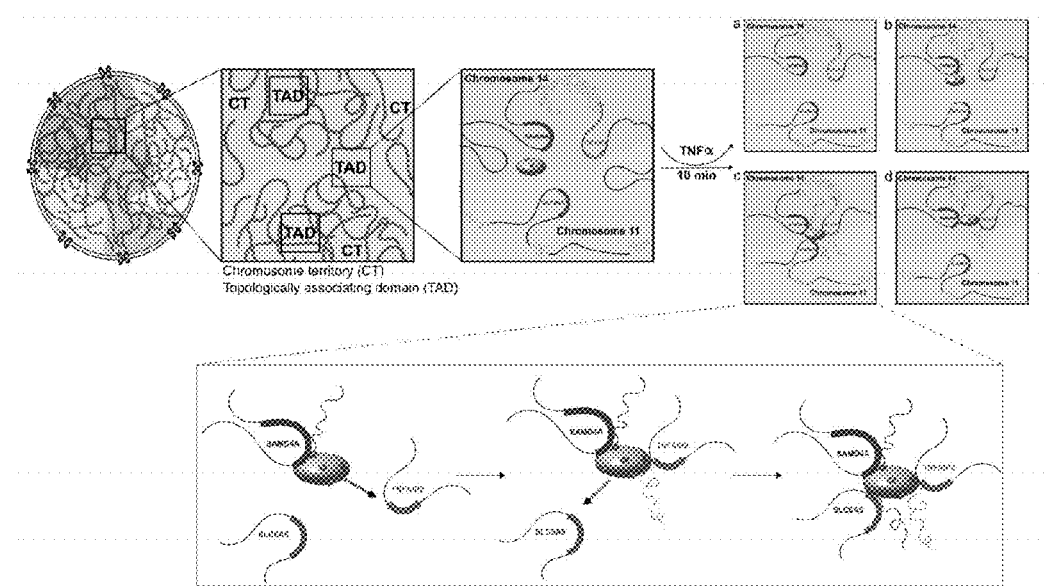
FIG. 50: Hypothetical model of hierarchical transcription between coregulated genes in a multigene complex. TADs constrain genes to compartments in the nucleus that are admissible to long-range chromosomal interactions. Upon induction by TNFα, NF-kB responsive genes engage in chromosomal interactions. As two of these genes reside on the same chromosome but almost 50 Mbp apart, and another resides on a different chromosome, these interactions most likely occur within a TAD. Single cell analysis 10 mins post TNFα stimulation, reveals that the transcriptional response of interacting genes in a multigene complex is asymmetric (FIG. 9). Allelic analysis revealed the following 4 categories were most prevalent; (a) no transcription of any gene, (b) SAMD4A expression only, (c) SAMD4A, SLC6A5 and TNFAIP2 combined expression and (d) combined expression of SAMD4A and TNFAIP2. Despite the low frequency of these interactions (FIG. 10), disrupting the sites within the gene loops that engage in chromosomal contact revealed a hierarchical organization between this TNFα-induced multigene complex.
Figure 51:
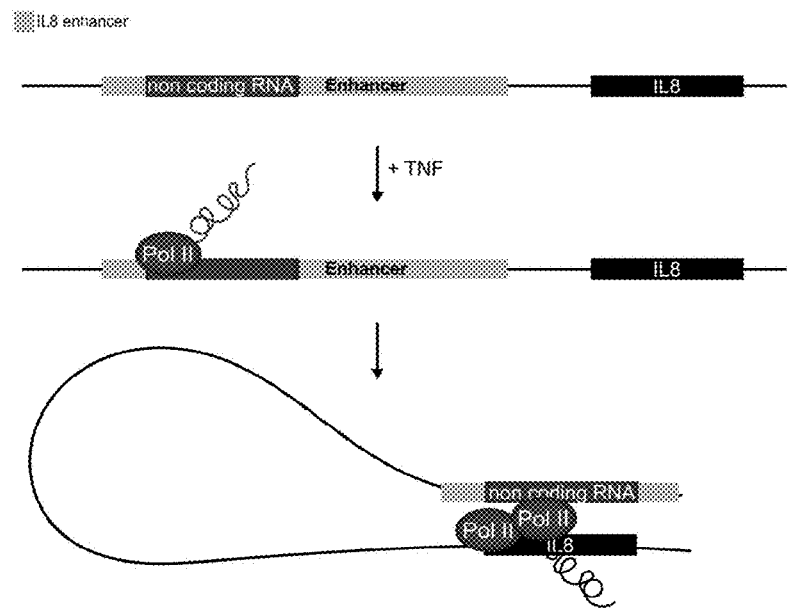
FIG. 51: Disrupting the IL8 enhancer abrogates transcription of the CXC proinflammatory genes. (A) The IL-8 enhancer is brough in close proximity to the IL8 by chromosomal looping. (B) Inducing a DSB in the IL8 promoter abrogates IL8 expression as well as the expression of a non coding RNA that is transcribed in the enhancer. Two-tailed Fisher exact test; *P<0.05, P<0.01, *P<0.001, n, number of DSBs. Cells were counterstained with DAPI. Bar, 5 µm.
Figure 51:
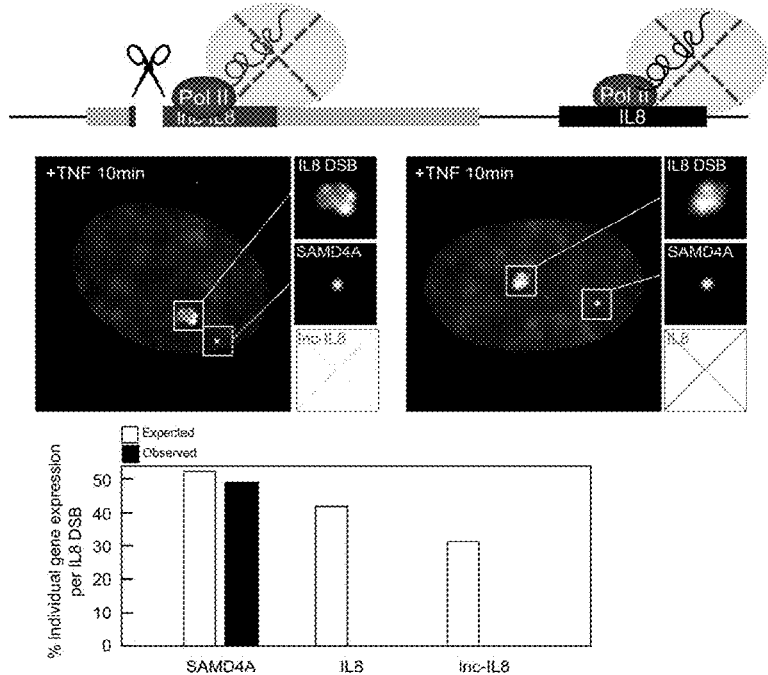

Here we show that disrupting sites within gene loops that engage in chromosomal contact significantly impacts the transcription of interacting genes in a multigene complex. We revealed this level of gene regulation by implementing a novel single cell strategy that allows discrete perturbation within chromatin loops. Initial evidence for this regulation was our single cell based observation of the hierarchical transcriptional response of these 3 genes to TNFα induction (FIG. 9). Despite the clear asymmetric transcriptional response, co-localization of RNA FISH foci was only observed in a subset of the population (FIG. 5). The functional relationship between chromosomal contact and co-transcription of interacting members of a multigene complex remains opaque. However, if loop-mediated contact is indeed a prerequisite for co-transcription, the RNA FISH co-localization data suggests that only certain cells in the population may possess the correct spatial arrangements of their chromosomes to permit such regulation (FIG. 5). Such variegated gene expression is suggested to occur in TADs, highly conserved compartments within mammalian chromosome territories (Dixon et al., 2012). We speculate that TADs may ensure robust SAMD4A, TNFAIP2 and SLC6A5 gene regulation by constraining these genes to areas permissible to long-range interactions (FIG. 50). Indeed, analysis of DNA in unstimulated HUVECs revealed that despite occupying distal genomic locations, in a fraction of the HUVEC population, the SAMD4A, TNFAIP2 and SLC6A5 DNA are in close proximity prior to TNFα induction (FIG. 8). The enrichment of chromosomal interactions in these 'jackpot' cells, may contribute to hierarchical SAMD4A, TNFAIP2 and SLC6A5 gene expression. However, current biochemical and imaging technologies lack the spatiotemporal resolution to interrogate whether loop-mediated co-transcription between these genes can only occur in these 'jackpot' cells. Alternatively, given more time, whether these chromosomal interactions may occur in most cells across the population.

Chromosomal translocations are natural perturbations in chromosome structure, which alter the spatial positioning of DNA within chromosome territories. Interestingly, these discrete perturbations in chromosome structure do not only influence genes located near to the breakpoint, but are sufficient to modify gene expression in cis and trans. Therefore, through the repositioning of chromosomes and relocation of DNA into different TADs, translocations may alter transcription by disrupting intra- and interchromosomal interactions. We were able to reveal that perturbing the SAMD4A gene loop has a direct effect on the transcriptional status of TNFAIP2 and SLC6A5 (FIG. 22). In addition, corresponding to the transcriptional response (FIG. 9), the effect on co-transcription was hierarchical, with the perturbation of TNFAIP2 altering SLC6A5 expression, but having no influence on SAMD4A (FIG. 26). Furthermore, perturbing SLC6A5 did not impact either SAMD4A or TNFAIP2 transcription (FIG. 35). This observation raises the question: if all the factors necessary for transcription are present, why does transcription of these interacting genes not occur? A possible explanation is that the recruitment of the multitude of repair proteins to the DSB acts as an obstruction to the normal chromatin contacts between these genes loops. Alternatively, contacts between interacting genes may still be present but are 'bridged' by the repair machinery. Although this "bridging" maintains the contact between gene loops, it is still inadequate for transcriptional activity to occur. It is important to note that the DNA of these 3 loci appear to be in close proximity in unstimulated HUVECs, despite the absence of 3C contact (Papantonis et al., 2010). Thus, it would be very difficult to definitively show that the disruption of a gene loop abrogates contact between other interacting genes, at least as measured by diffraction limited co-localized DNA FISH foci. Another possible explanation could be that the DNA repair machinery is occluding the entry of RNA Pol II to the other interacting genes. However, the observed unidirectional loss of transcription between these three genes (FIGS. 20, 22, 26 and 35) excludes this possibility. Thus, taken together, the most likely conclusion is that the DSB serves to disrupt chromosomal contact between interacting genes. The repair experiment reveals that restoration of an intact SAMD4A gene loop, in a sequence-independent manner, is sufficient to restore co-transcription, as well as co-localization, of TNFAIP2 and SLC6A5 (FIG. 49). Therefore, we speculate that by disrupting chromosomal interactions, the topological framework (comprised of gene loops and RNA Pol II) is unable to assemble, thus, disrupting transcription. Collectively, these data provide strong evidence that intact chromatin is a requirement for loop-mediated co-transcription.

One way enhancer-promoter interactions are proposed to enhance transcription, is by bringing protein complexes to the promoter (Deng et al., 2012). In an analogous manner, through interchromosomal interactions, NF-κB has been shown to be delivered to the promoter of inducible genes. Similarly, we propose SAMD4A to be the dominant member of the NF-κB multigene complex that "organizes" transcription through loop-mediated contact. Recent published data in live cells reveals that RNA Pol II is mobile and clustering precedes transcriptional elongation and is linked to transcriptional initiation (Cisse et al., 2013). Therefore, we speculate that the SAMD4A gene loop provides a topological platform that serves as a scaffold on which a focus of many RNA Pol II molecules can cluster and engage in transcription of subordinate members of the multigene complex. When TNFAIP2 or SLC6A5 cannot engage in chromosomal contact, their ability to access the focus of Pol II is limited. The strict hierarchical relationship between the interacting members further suggests a hand off or "collector" process, where dynamic chromosomal contacts with the dominant gene loop are formed (FIG. 50). This could occur by a mechanism where TNFAIP2 via chromosomal contact "collects" its Pol II from an intact SAMD4A gene loop and in turn SLC6A5 from an intact TNFAIP2 loop. Therefore, these data argue neither in favor of nor against putative "transcription factories," as they are currently defined, but suggest that such factories may be dynamically assembled rather than immobile structures. A recent study revealed that sequences within the promoter might drive the co-localization between these NFkB-regulated genes (Papantonis et al., 2013). Therefore, an alternative model might involve sequence specific elements within the promoters that facilitate the accumulation of different thresholds of general transcription factors for the 3 genes. Therefore, only upon the creation of a nuclear subcompartment of sufficient activity by SAMD4A can TNFAIP2 and then SLC6A5 be activated.

Our observation shifts the general paradigm of how transcriptional regulation in three dimensions occurs. Although these chromosomal interactions are rare and stochastic (Noordermeer et al., 2011), our single cell view strongly suggests that chromosomal contact between genes engaged in multigene complexes have a significant impact on co-transcription of interacting genes. Such long-range interactions of co-transcribed genes could serve to organize transcription in nuclear space, using hierarchical relationships between gene loops. Without gene loops of dominant members, subordinate members of the multigene complex cannot engage in long-range chromosomal contacts, nor can they participate in transcription. Finally, as looping enables stochastic chromosomal contact between genes in multigene complexes, this study provides supporting evidence to prior work showing that gene looping is a fundamental requirement of transcriptional activity (Tan-Wong et al., 2012). Importantly, such chromatin looping within multigene complexes (Li et al., 2012) may be governed by similar hierarchical regulation. Perturbation of members of multigene complexes, through knockouts, gene deletions, chromosomal translocations or silencing of transcription factors, all of which disrupt loop-mediated contact, may inadvertently result in unintended consequences to transcription of other members of a given multigene complex.

REFERENCES

Boch, J., et al. (2009) *Science* 326, 1509-1512.
Christian, M., et al. (2010) *Genetics* 186, 757-761.
Cisse, I. I., et al. (2013) *Science* 341, 664-7.
Dekker, J., et al. (2002) *Science* 295, 1306-1311.
Deng, W., et al. (2012) *Cell* 149, 1233-1244.
Dixon, J. R., et al. (2012) *Nature* 485, 376-380.
Fanucchi et al. (2013) *Cell* 155, 606-20.
Fullwood, M. J., et al. (2009) *Nature* 462, 58-64.
Li, T., et al. (2011) *Nucl. Acids Res.* 39, 359-372.
Li, G., et al. (2012) *Cell* 148, 84-98.
Lieberman-Aiden, E., et al. (2009) *Science* 326, 289-293.
Noordermeer, D., et al. (2011) *Nat Cell Biol* 13, 944-951.
Papantonis, A., et al. (2010) *PLoS Biol* 8: e1000419.

Tan-Wong, S. M., et al. (2012) *Science* 338, 671-675.
Bienko, M., et al. (2013) *Nat Methods.* 10, 122-124.
Keogh, M. C., et al. (2005) *Nature* 439, 497-501.
Shanbhag, N. M., et al. (2010) *Cell* 141, 970-981.

The invention claimed is:

1. A method for silencing gene expression at a single cell level in vitro, the method comprising the steps of:
  (i) perturbing at least one chromosomal contact in the cell by by inducing a site specific double stranded break in a region of DNA involved in chromosomal contact; (ii) detecting the site of at least one double-stranded break; and (iii) detecting the effect of at least one perturbation on the transcriptional activity of at least one gene of interest, wherein the effect of the perturbation is abrogation of the transcriptional activity of the gene of interest and further wherein the site specific double stranded break in not induced in the gene of interest.

2. The method of claim 1, wherein the transcriptional activity of at least one gene of interest may be abrogated by a mechanism selected from the group consisting of:
  (i) the recruitment of proteins involved in a repair process of the double stranded break, which when bound to the DNA obstruct at least one chromosomal contact,
  (ii) the enhancement of mobility of the region of DNA containing the double stranded break, which results in a reduction in the capacity of a gene loop to engage in chromosomal contact; and
  (iii) the loss of structural integrity of a gene loop, which results in the abrogation of chromosomal contact.

3. The method of claim 1, wherein at least one chromosomal contact may be an intergenic contact, an intragenic contact or both.

4. The method of claim 1, wherein the region of DNA that is perturbed comprises a gene or regulatory element selected from the group consisting of: (i) an enhancer and/or promoter, (ii) a site within a DNA loop that engages in intra- or inter-chromosomal contact, and (iii) a regulatory site within a DNA loop which determines the loop structure.

5. The method of claim 1, wherein at least one chromosomal contact is between DNA located either inter-chromosomally, intra-chromosomally or both.

6. The method of claim 1, wherein the double-stranded break is induced by a site-specific nuclease.

7. The method of claim 6, wherein the site-specific nuclease is selected from a group consisting of a meganuclease, a zinc finger nuclease, a TALE nuclease, a BUD1 nuclease, and a CrispR nuclease.

8. The method of claim 6, wherein the site-specific nuclease is delivered to the cell by transfection of the cell with a vector encoding the site-specific nuclease wherein the site-specific nuclease is expressed in the cell.

9. The method of claim 1, wherein the double-stranded break is detected by immunofluorescent staining of a protein involved in the cellular repair process, or by detecting the location of a recombinant protein expressing a fluorescent label which is involved in the cellular repair process.

10. The method of claim 1, wherein the effect of the double-stranded break on the transcriptional activity of the gene of interest is detected using a method selected from the group consisting of RNA fluorescent in situ hybridisation, live RNA fluorescent in situ hybridisation, immunogold labelling, molecular beacons and MS2 tagging.

11. The method of claim 1, wherein the cell is a eukaryotic cell or prokaryotic cell.

12. The method of claim 6, wherein the site-specific nuclease is exogenously expressed and delivered to the cell.

* * * * *

```
                          SEQUENCE LISTING

<160> NUMBER OF SEQ ID NOS: 416

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tccacgttta taaatagctg                                                   20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
cactggggtg tggaagcata                                                   20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
ttcgcggccc acctggccgc                                                   20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
ctgtgcgagc gcgacaccta                                                   20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
ttgtcccttt aaaacttgaa                                                   20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
ttatcaaact tgtattatca                                                   20

<210> SEQ ID NO 7
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
tgcagcgcca cagtccccgg                                              20

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
caaccgttca gaggtcccca g                                            21

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
tgagggagat tccattgagc                                              20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
ggaaaaagtg ctgctccaac                                              20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
tgcaggacag actcaggaca                                              20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
atttgggttg agcattccac                                              20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
```

```
tgatttaacc ccctccttcc                                              20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
ctttaggagc cacagccaac                                              20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
ctagtacctc cgcacgtggt                                              20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
tccagcacca ctattggaaa                                              20

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide

<400> SEQUENCE: 17
tgctgctgca ggagggtg                                                18

<210> SEQ ID NO 18
<211> LENGTH: 90
<212> TYPE: DNA
<213> ORGANISM: Artificial Sequence
<220> FEATURE:
<223> OTHER INFORMATION: Oligonucleotide

<400> SEQUENCE: 18
gatcgctagc acctgtggag agaaaggcaa agtggatgtc agtaagacca ataggtgcct    60
atcatggccc tccagctatt tataaacgtg                                    90

<210> SEQ ID NO 19
<211> LENGTH: 82
<212> TYPE: DNA
<213> ORGANISM: Artificial Sequence
<220> FEATURE:
<223> OTHER INFORMATION: Oligonucleotide

<400> SEQUENCE: 19
gatcgctagc aggtaagtat caaggttaca agacaggttt aaggagacca atagaaactg    60
gggcctcctt cactggggtg tg                                            82
```

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide

<400> SEQUENCE: 20
cttttgtata tctacatcat ttagcagcat g                             31

<210> SEQ ID NO 21
<211> LENGTH: 30
<212> TYPE: DNA
<213> ORGANISM: Artificial Sequence
<220> FEATURE:
<223> OTHER INFORMATION: Oligonucleotide

<400> SEQUENCE: 21
gatcgctagc cccctaacg ttactggccg                                30

<210> SEQ ID NO 22
<211> LENGTH: 40
<212> TYPE: DNA
<213> ORGANISM: Artificial Sequence
<220> FEATURE:
<223> OTHER INFORMATION: Oligonucleotide

<400> SEQUENCE: 22
gatcgctagc ggatcctcac ttgtacagct cgtccatgcc                    40

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide

<400> SEQUENCE: 23
ccacacccca gtgaaggag                                           19

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide

<400> SEQUENCE: 24
taaatagctg gagggccatg                                          20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
attcatgcta ccgtagctac                                          20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
ggaaactgca tgagagaaaa                                            20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
gacctgactt acttatttcc                                            20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide

<400> SEQUENCE: 28
ccagaaaatc cagactctac                                            20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
ggaggaagga aaaacacac                                             20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
agccacgttg cccaaaagaa                                            20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
catgtgttgc tgaaatccag                                            20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
atccaagctt ggcttctgaa                                            20

<210> SEQ ID NO 33

```
<210> SEQ ID NO 33
<211> LENGTH: 20
<212> TYPE: DNA
<213> ORGANISM: Artificial Sequence
<220> FEATURE:
<223> OTHER INFORMATION: Oligonucleotide

<400> SEQUENCE: 33
ttcatgtact cctcacacag                                          20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide

<400> SEQUENCE: 34
ccagaatatc tgtggggaaa                                          20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
ttctgaagac gaagctctaa                                          20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
ttactagtct ctagcgtcac                                          20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
gcagtaagct taaccgcatt                                          20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
caagatccgt atcaatatgg                                          20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39
```
cctttctcca agacccttttt 20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
aagtaaccca cttcatgcct 20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide

<400> SEQUENCE: 41
gcagggtaat atgaaacgat 20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
catactagtt gaggtgtctg 20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
gctggacctt tcgactatat 20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
ccacgctagc aaataggaaa 20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide

<400> SEQUENCE: 45
cctaccctcc aggatataat 20

<210> SEQ ID NO 46
<211> LENGTH: 20
<212> TYPE: DNA

<213> ORGANISM: Artificial Sequence
<220> FEATURE:
<223> OTHER INFORMATION: Oligonucleotide

<400> SEQUENCE: 46
tcacaaccat cagactttcc                                                   20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide

<400> SEQUENCE: 47
gcagcagcat gaactaaaga                                                   20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
taaacactgg ggactctgtt                                                   20

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide

<400> SEQUENCE: 49
accctgcatt cttttctctg                                                   20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50
aacatggaac agctggaaga                                                   20

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide

<400> SEQUENCE: 51
accttgtcat caaatggcag                                                   20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
actcacttta gtgtctccca                                                   20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide

<400> SEQUENCE: 53
tcgcttcttg ctgctctgaa                                              20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide

<400> SEQUENCE: 54
atactaggga ggaggaatga                                              20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide

<400> SEQUENCE: 55
tgttttcacc atcgtgcaca                                              20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide

<400> SEQUENCE: 56
atatggaagc atcccattct                                              20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide

<400> SEQUENCE: 57
cacttccacc ctatgattct                                              20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide

<400> SEQUENCE: 58
aactgtgaag atttccagcg                                              20

<210> SEQ ID NO 59
<211> LENGTH: 20
<212> TYPE: DNA
<213> ORGANISM: Artificial Sequence
<220> FEATURE:

<223> OTHER INFORMATION: Oligonucleotide

<400> SEQUENCE: 59
agtcctgtct ggtcaggaaa                                          20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide

<400> SEQUENCE: 60
ttggccatgc aggatctttc                                          20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide

<400> SEQUENCE: 61
atggaatctc cctcaatgtg                                          20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide

<400> SEQUENCE: 62
aaacgtggag ctcaaccaaa                                          20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
aattatgctt ccacacccca                                          20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
agagggtgga tcatcagtta                                          20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide

<400> SEQUENCE: 65
ccgctgaaat taaggaagga                                          20

```
<210> SEQ ID NO 66
<211> LENGTH: 20
<212> TYPE: DNA
<213> ORGANISM: Artificial Sequence
<220> FEATURE:
<223> OTHER INFORMATION: Oligonucleotide

<400> SEQUENCE: 66
aaaaccgagc aggtaaacca                                               20

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
ccttgtttgt caaacctgag                                               20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide

<400> SEQUENCE: 68
gcgtaaatcc tctgcaatct                                               20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide

<400> SEQUENCE: 69
ccagcactga aatcaagcat                                               20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide

<400> SEQUENCE: 70
agatgagttt gaacagtccc                                               20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide

<400> SEQUENCE: 71
gtgctgctcc aacatttgaa                                               20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide
```

<400> SEQUENCE: 72
ctccattact caaagggaaa                                              20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide

<400> SEQUENCE: 73
ccccacccaa tatgaatgaa                                              20

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide

<400> SEQUENCE: 74
ctgttgagac tcattcttgt                                              20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide

<400> SEQUENCE: 75
gctttaaaat gtcgctgggt                                              20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide

<400> SEQUENCE: 76
gtgatggccc tttgatttac                                              20

<210> SEQ ID NO 77
<211> LENGTH: 20
<212> TYPE: DNA
<213> ORGANISM: Artificial Sequence
<220> FEATURE:
<223> OTHER INFORMATION: Oligonucleotide

<400> SEQUENCE: 77
taatcctgcc attcctaagc                                              20

<210> SEQ ID NO 78
<211> LENGTH: 20
<212> TYPE: DNA
<213> ORGANISM: Artificial Sequence
<220> FEATURE:
<223> OTHER INFORMATION: Oligonucleotide

<400> SEQUENCE: 78
ccactgttta accgcaacaa                                              20

<210> SEQ ID NO 79
<211> LENGTH: 20

<212> TYPE: DNA
<213> ORGANISM: Artificial Sequence
<220> FEATURE:
<223> OTHER INFORMATION: Oligonucleotide

<400> SEQUENCE: 79
aattccaaca ttggagcctc                                               20

<210> SEQ ID NO 80
<211> LENGTH: 20
<212> TYPE: DNA
<213> ORGANISM: Artificial Sequence
<220> FEATURE:
<223> OTHER INFORMATION: Oligonucleotide

<400> SEQUENCE: 80
cacacagaca caagattcaa                                               20

<210> SEQ ID NO 81
<211> LENGTH: 20
<212> TYPE: DNA
<213> ORGANISM: Artificial Sequence
<220> FEATURE:
<223> OTHER INFORMATION: Oligonucleotide

<400> SEQUENCE: 81
ggtttctgcc taaaacagca                                               20

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide

<400> SEQUENCE: 82
attctctcca agtcatcagc                                               20

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide

<400> SEQUENCE: 83
taagagtgtc tgaggggtta                                               20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide

<400> SEQUENCE: 84
gtctagccag actgtagttt                                               20

<210> SEQ ID NO 85
<211> LENGTH: 20
<212> TYPE: DNA
<213> ORGANISM: Artificial Sequence
<220> FEATURE:
<223> OTHER INFORMATION: Oligonucleotide

<400> SEQUENCE: 85

| | |
|---|---|
| ctcaccccaa agtctttaag | 20 |

<210> SEQ ID NO 86
<211> LENGTH: 20
<212> TYPE: DNA
<213> ORGANISM: Artificial Sequence
<220> FEATURE:
<223> OTHER INFORMATION: Oligonucleotide

<400> SEQUENCE: 86

| | |
|---|---|
| tctaaggact tagcaccatc | 20 |

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide

<400> SEQUENCE: 87

| | |
|---|---|
| gccttcggag ttttcttctt | 20 |

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide

<400> SEQUENCE: 88

| | |
|---|---|
| tttctctcca acatggttgc | 20 |

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide

<400> SEQUENCE: 89

| | |
|---|---|
| gtttctacat tgcttccctc | 20 |

<210> SEQ ID NO 90
<211> LENGTH: 20
<212> TYPE: DNA
<213> ORGANISM: Artificial Sequence
<220> FEATURE:
<223> OTHER INFORMATION: Oligonucleotide

<400> SEQUENCE: 90

| | |
|---|---|
| tttctgtcct gctttctcct | 20 |

<210> SEQ ID NO 91
<211> LENGTH: 20
<212> TYPE: DNA
<213> ORGANISM: Artificial Sequence
<220> FEATURE:
<223> OTHER INFORMATION: Oligonucleotide

<400> SEQUENCE: 91

| | |
|---|---|
| aaagaagtct ctggtaccag | 20 |

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide

<400> SEQUENCE: 92
gtctagccca agtgagagaa                                           20

<210> SEQ ID NO 93
<211> LENGTH: 20
<212> TYPE: DNA
<213> ORGANISM: Artificial Sequence
<220> FEATURE:
<223> OTHER INFORMATION: Oligonucleotide

<400> SEQUENCE: 93
taaaccagaa gcctgtctct                                           20

<210> SEQ ID NO 94
<211> LENGTH: 20
<212> TYPE: DNA
<213> ORGANISM: Artificial Sequence
<220> FEATURE:
<223> OTHER INFORMATION: Oligonucleotide

<400> SEQUENCE: 94
atctaatcca tggccagcca                                           20

<210> SEQ ID NO 95
<211> LENGTH: 20
<212> TYPE: DNA
<213> ORGANISM: Artificial Sequence
<220> FEATURE:
<223> OTHER INFORMATION: Oligonucleotide

<400> SEQUENCE: 95
aaagggcatt gattccacag                                           20

<210> SEQ ID NO 96
<211> LENGTH: 20
<212> TYPE: DNA
<213> ORGANISM: Artificial Sequence
<220> FEATURE:
<223> OTHER INFORMATION: Oligonucleotide

<400> SEQUENCE: 96
acttggaaag atgtcccaag                                           20

<210> SEQ ID NO 97
<211> LENGTH: 20
<212> TYPE: DNA
<213> ORGANISM: Artificial Sequence
<220> FEATURE:
<223> OTHER INFORMATION: Oligonucleotide

<400> SEQUENCE: 97
cccagttaat cctaaggaaa                                           20

<210> SEQ ID NO 98
<211> LENGTH: 20
<212> TYPE: DNA
<213> ORGANISM: Artificial Sequence
<220> FEATURE:
<223> OTHER INFORMATION: Oligonucleotide

<400> SEQUENCE: 98
gcttcttctt tgtacagtga                                           20

<210> SEQ ID NO 99
<211> LENGTH: 20
<212> TYPE: DNA
<213> ORGANISM: Artificial Sequence
<220> FEATURE:
<223> OTHER INFORMATION: Oligonucleotide

<400> SEQUENCE: 99
cagtcctcta gcaatggaaa                                               20

<210> SEQ ID NO 100
<211> LENGTH: 20
<212> TYPE: DNA
<213> ORGANISM: Artificial Sequence
<220> FEATURE:
<223> OTHER INFORMATION: Oligonucleotide

<400> SEQUENCE: 100
gtgtgtgtgt gtgtgtgtat                                               20

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide

<400> SEQUENCE: 101
tttcgtgtgt gtgtgtgtgt                                               20

<210> SEQ ID NO 102
<211> LENGTH: 20
<212> TYPE: DNA
<213> ORGANISM: Artificial Sequence
<220> FEATURE:
<223> OTHER INFORMATION: Oligonucleotide

<400> SEQUENCE: 102
aaagccactg tctgtgctat                                               20

<210> SEQ ID NO 103
<211> LENGTH: 20
<212> TYPE: DNA
<213> ORGANISM: Artificial Sequence
<220> FEATURE:
<223> OTHER INFORMATION: Oligonucleotide

<400> SEQUENCE: 103
aaaggaagta tcttcatccc                                               20

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide

<400> SEQUENCE: 104
cagaagagac tagaacagac                                               20

<210> SEQ ID NO 105
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 105
actagtttct gttccacgca                                          20

<210> SEQ ID NO 106
<211> LENGTH: 20
<212> TYPE: DNA
<213> ORGANISM: Artificial Sequence
<220> FEATURE:
<223> OTHER INFORMATION: Oligonucleotide

<400> SEQUENCE: 106
cttcatctcc ttaagctagc                                          20

<210> SEQ ID NO 107
<211> LENGTH: 20
<212> TYPE: DNA
<213> ORGANISM: Artificial Sequence
<220> FEATURE:
<223> OTHER INFORMATION: Oligonucleotide

<400> SEQUENCE: 107
catgtcattc ccacaagaac                                          20

<210> SEQ ID NO 108
<211> LENGTH: 20
<212> TYPE: DNA
<213> ORGANISM: Artificial Sequence
<220> FEATURE:
<223> OTHER INFORMATION: Oligonucleotide

<400> SEQUENCE: 108
tgagaaggtt tctgtccatg                                          20

<210> SEQ ID NO 109
<211> LENGTH: 20
<212> TYPE: DNA
<213> ORGANISM: Artificial Sequence
<220> FEATURE:
<223> OTHER INFORMATION: Oligonucleotide

<400> SEQUENCE: 109
aaagcttccc aattctagcc                                          20

<210> SEQ ID NO 110
<211> LENGTH: 20
<212> TYPE: DNA
<213> ORGANISM: Artificial Sequence
<220> FEATURE:
<223> OTHER INFORMATION: Oligonucleotide

<400> SEQUENCE: 110
ccgaaggtga atgtcttaag                                          20

<210> SEQ ID NO 111
<211> LENGTH: 20
<212> TYPE: DNA
<213> ORGANISM: Artificial Sequence
<220> FEATURE:
<223> OTHER INFORMATION: Oligonucleotide

<400> SEQUENCE: 111
atctcctaat gctatccctc                                          20

<210> SEQ ID NO 112
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 112
ctgcacccat taactcatca                                              20

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide

<400> SEQUENCE: 113
tatacatgtg ccgtgttggt                                              20

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide

<400> SEQUENCE: 114
caacgtgcag gtttgttaca                                              20

<210> SEQ ID NO 115
<211> LENGTH: 20
<212> TYPE: DNA
<213> ORGANISM: Artificial Sequence
<220> FEATURE:
<223> OTHER INFORMATION: Oligonucleotide

<400> SEQUENCE: 115
gagagaatgt aagaaggcga                                              20

<210> SEQ ID NO 116
<211> LENGTH: 20
<212> TYPE: DNA
<213> ORGANISM: Artificial Sequence
<220> FEATURE:
<223> OTHER INFORMATION: Oligonucleotide

<400> SEQUENCE: 116
tttagcctga caggcatgaa                                              20

<210> SEQ ID NO 117
<211> LENGTH: 20
<212> TYPE: DNA
<213> ORGANISM: Artificial Sequence
<220> FEATURE:
<223> OTHER INFORMATION: Oligonucleotide

<400> SEQUENCE: 117
gtgcacttga agtaacaagg                                              20

<210> SEQ ID NO 118
<211> LENGTH: 20
<212> TYPE: DNA
<213> ORGANISM: Artificial Sequence
<220> FEATURE:
<223> OTHER INFORMATION: Oligonucleotide

<400> SEQUENCE: 118
```
tgatgtcctt gatactggtc					20

<210> SEQ ID NO 119
<211> LENGTH: 20
<212> TYPE: DNA
<213> ORGANISM: Artificial Sequence
<220> FEATURE:
<223> OTHER INFORMATION: Oligonucleotide

<400> SEQUENCE: 119
gctgcatttc caagaagatc					20

<210> SEQ ID NO 120
<211> LENGTH: 20
<212> TYPE: DNA
<213> ORGANISM: Artificial Sequence
<220> FEATURE:
<223> OTHER INFORMATION: Oligonucleotide

<400> SEQUENCE: 120
attcagtagg tctgcagtgt					20

<210> SEQ ID NO 121
<211> LENGTH: 20
<212> TYPE: DNA
<213> ORGANISM: Artificial Sequence
<220> FEATURE:
<223> OTHER INFORMATION: Oligonucleotide

<400> SEQUENCE: 121
tacctgccct atcacccctc					20

<210> SEQ ID NO 122
<211> LENGTH: 20
<212> TYPE: DNA
<213> ORGANISM: Artificial Sequence
<220> FEATURE:
<223> OTHER INFORMATION: Oligonucleotide

<400> SEQUENCE: 122
accttcctct caccttctcc					20

<210> SEQ ID NO 123
<211> LENGTH: 20
<212> TYPE: DNA
<213> ORGANISM: Artificial Sequence
<220> FEATURE:
<223> OTHER INFORMATION: Oligonucleotide

<400> SEQUENCE: 123
agaggacatg ctcaggagca					20

<210> SEQ ID NO 124
<211> LENGTH: 20
<212> TYPE: DNA
<213> ORGANISM: Artificial Sequence
<220> FEATURE:
<223> OTHER INFORMATION: Oligonucleotide

<400> SEQUENCE: 124
tagctctgct cagctccaga					20

<210> SEQ ID NO 125
<211> LENGTH: 20
<212> TYPE: DNA

<213> ORGANISM: Artificial Sequence
<220> FEATURE:
<223> OTHER INFORMATION: Oligonucleotide

<400> SEQUENCE: 125
atcacttgga actctcctgc    20

<210> SEQ ID NO 126
<211> LENGTH: 20
<212> TYPE: DNA
<213> ORGANISM: Artificial Sequence
<220> FEATURE:
<223> OTHER INFORMATION: Oligonucleotide

<400> SEQUENCE: 126
taacaagaca cgtggcccta    20

<210> SEQ ID NO 127
<211> LENGTH: 20
<212> TYPE: DNA
<213> ORGANISM: Artificial Sequence
<220> FEATURE:
<223> OTHER INFORMATION: Oligonucleotide

<400> SEQUENCE: 127
acagggtaac cctacacaat    20

<210> SEQ ID NO 128
<211> LENGTH: 20
<212> TYPE: DNA
<213> ORGANISM: Artificial Sequence
<220> FEATURE:
<223> OTHER INFORMATION: Oligonucleotide

<400> SEQUENCE: 128
tgtactcagc agggtacca    20

<210> SEQ ID NO 129
<211> LENGTH: 20
<212> TYPE: DNA
<213> ORGANISM: Artificial Sequence
<220> FEATURE:
<223> OTHER INFORMATION: Oligonucleotide

<400> SEQUENCE: 129
atctatggag tcaagggacg    20

<210> SEQ ID NO 130
<211> LENGTH: 20
<212> TYPE: DNA
<213> ORGANISM: Artificial Sequence
<220> FEATURE:
<223> OTHER INFORMATION: Oligonucleotide

<400> SEQUENCE: 130
atgcagaccg tgcgaatgac    20

<210> SEQ ID NO 131
<211> LENGTH: 20
<212> TYPE: DNA
<213> ORGANISM: Artificial Sequence
<220> FEATURE:
<223> OTHER INFORMATION: Oligonucleotide

<400> SEQUENCE: 131
acactgcagt aagcctctct    20

<210> SEQ ID NO 132
<211> LENGTH: 20
<212> TYPE: DNA
<213> ORGANISM: Artificial Sequence
<220> FEATURE:
<223> OTHER INFORMATION: Oligonucleotide

<400> SEQUENCE: 132
acaataacag cccctggact                                               20

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide

<400> SEQUENCE: 133
ttcacactag gatctggggc                                               20

<210> SEQ ID NO 134
<211> LENGTH: 20
<212> TYPE: DNA
<213> ORGANISM: Artificial Sequence
<220> FEATURE:
<223> OTHER INFORMATION: Oligonucleotide

<400> SEQUENCE: 134
ctccaggctt ccttcctaaa                                               20

<210> SEQ ID NO 135
<211> LENGTH: 20
<212> TYPE: DNA
<213> ORGANISM: Artificial Sequence
<220> FEATURE:
<223> OTHER INFORMATION: Oligonucleotide

<400> SEQUENCE: 135
acactgccca cactgtctat                                               20

<210> SEQ ID NO 136
<211> LENGTH: 20
<212> TYPE: DNA
<213> ORGANISM: Artificial Sequence
<220> FEATURE:
<223> OTHER INFORMATION: Oligonucleotide

<400> SEQUENCE: 136
ttcaacacga actgagccca                                               20

<210> SEQ ID NO 137
<211> LENGTH: 20
<212> TYPE: DNA
<213> ORGANISM: Artificial Sequence
<220> FEATURE:
<223> OTHER INFORMATION: Oligonucleotide

<400> SEQUENCE: 137
atccttctgc cagaggctga                                               20

<210> SEQ ID NO 138
<211> LENGTH: 20
<212> TYPE: DNA
<213> ORGANISM: Artificial Sequence
<220> FEATURE:

<223> OTHER INFORMATION: Oligonucleotide

<400> SEQUENCE: 138
ctctccactg gacccttcct                                              20

<210> SEQ ID NO 139
<211> LENGTH: 20
<212> TYPE: DNA
<213> ORGANISM: Artificial Sequence
<220> FEATURE:
<223> OTHER INFORMATION: Oligonucleotide

<400> SEQUENCE: 139
tatgccctgc tgactcctct                                              20

<210> SEQ ID NO 140
<211> LENGTH: 20
<212> TYPE: DNA
<213> ORGANISM: Artificial Sequence
<220> FEATURE:
<223> OTHER INFORMATION: Oligonucleotide

<400> SEQUENCE: 140
ttatctctcc cgtggcccct                                              20

<210> SEQ ID NO 141
<211> LENGTH: 20
<212> TYPE: DNA
<213> ORGANISM: Artificial Sequence
<220> FEATURE:
<223> OTHER INFORMATION: Oligonucleotide

<400> SEQUENCE: 141
agcaagcggg aactggctct                                              20

<210> SEQ ID NO 142
<211> LENGTH: 20
<212> TYPE: DNA
<213> ORGANISM: Artificial Sequence
<220> FEATURE:
<223> OTHER INFORMATION: Oligonucleotide

<400> SEQUENCE: 142
catttcctgg tgagtcagga                                              20

<210> SEQ ID NO 143
<211> LENGTH: 20
<212> TYPE: DNA
<213> ORGANISM: Artificial Sequence
<220> FEATURE:
<223> OTHER INFORMATION: Oligonucleotide

<400> SEQUENCE: 143
tcactgggac agaaagactg                                              20

<210> SEQ ID NO 144
<211> LENGTH: 20
<212> TYPE: DNA
<213> ORGANISM: Artificial Sequence
<220> FEATURE:
<223> OTHER INFORMATION: Oligonucleotide

<400> SEQUENCE: 144
ttgcctgttg ctaaccccag                                              20

```
<210> SEQ ID NO 145
<211> LENGTH: 20
<212> TYPE: DNA
<213> ORGANISM: Artificial Sequence
<220> FEATURE:
<223> OTHER INFORMATION: Oligonucleotide

<400> SEQUENCE: 145
tccatgccca gcttggcttt                                              20

<210> SEQ ID NO 146
<211> LENGTH: 20
<212> TYPE: DNA
<213> ORGANISM: Artificial Sequence
<220> FEATURE:
<223> OTHER INFORMATION: Oligonucleotide

<400> SEQUENCE: 146
acacaggctt caacgatgcc                                              20

<210> SEQ ID NO 147
<211> LENGTH: 20
<212> TYPE: DNA
<213> ORGANISM: Artificial Sequence
<220> FEATURE:
<223> OTHER INFORMATION: Oligonucleotide

<400> SEQUENCE: 147
ctccgttccc cacatttctg                                              20

<210> SEQ ID NO 148
<211> LENGTH: 20
<212> TYPE: DNA
<213> ORGANISM: Artificial Sequence
<220> FEATURE:
<223> OTHER INFORMATION: Oligonucleotide

<400> SEQUENCE: 148
caatccagat gcagctgtgt                                              20

<210> SEQ ID NO 149
<211> LENGTH: 20
<212> TYPE: DNA
<213> ORGANISM: Artificial Sequence
<220> FEATURE:
<223> OTHER INFORMATION: Oligonucleotide

<400> SEQUENCE: 149
aaatgacctt ctctctgccc                                              20

<210> SEQ ID NO 150
<211> LENGTH: 20
<212> TYPE: DNA
<213> ORGANISM: Artificial Sequence
<220> FEATURE:
<223> OTHER INFORMATION: Oligonucleotide

<400> SEQUENCE: 150
ctttgtctgc ctagaggttt                                              20

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide
```

<400> SEQUENCE: 151
agccctggca cttcctaagg					20

<210> SEQ ID NO 152
<211> LENGTH: 20
<212> TYPE: DNA
<213> ORGANISM: Artificial Sequence
<220> FEATURE:
<223> OTHER INFORMATION: Oligonucleotide

<400> SEQUENCE: 152
atcttggctc actgtcctgg					20

<210> SEQ ID NO 153
<211> LENGTH: 20
<212> TYPE: DNA
<213> ORGANISM: Artificial Sequence
<220> FEATURE:
<223> OTHER INFORMATION: Oligonucleotide

<400> SEQUENCE: 153
ccccaaactg ctccacagac					20

<210> SEQ ID NO 154
<211> LENGTH: 20
<212> TYPE: DNA
<213> ORGANISM: Artificial Sequence
<220> FEATURE:
<223> OTHER INFORMATION: Oligonucleotide

<400> SEQUENCE: 154
taggccagaa tgggcaggaa					20

<210> SEQ ID NO 155
<211> LENGTH: 20
<212> TYPE: DNA
<213> ORGANISM: Artificial Sequence
<220> FEATURE:
<223> OTHER INFORMATION: Oligonucleotide

<400> SEQUENCE: 155
aggtcttggg catctcacca					20

<210> SEQ ID NO 156
<211> LENGTH: 20
<212> TYPE: DNA
<213> ORGANISM: Artificial Sequence
<220> FEATURE:
<223> OTHER INFORMATION: Oligonucleotide

<400> SEQUENCE: 156
actcacagca gccctggaat					20

<210> SEQ ID NO 157
<211> LENGTH: 20
<212> TYPE: DNA
<213> ORGANISM: Artificial Sequence
<220> FEATURE:
<223> OTHER INFORMATION: Oligonucleotide

<400> SEQUENCE: 157
tgtcacccag ataaaaccct					20

<210> SEQ ID NO 158
<211> LENGTH: 20

```
<212> TYPE: DNA
<213> ORGANISM: Artificial Sequence
<220> FEATURE:
<223> OTHER INFORMATION: Oligonucleotide

<400> SEQUENCE: 158
ttcttcctgc tccaagacta                                                   20

<210> SEQ ID NO 159
<211> LENGTH: 20
<212> TYPE: DNA
<213> ORGANISM: Artificial Sequence
<220> FEATURE:
<223> OTHER INFORMATION: Oligonucleotide

<400> SEQUENCE: 159
gagccacctt taagatctga                                                   20

<210> SEQ ID NO 160
<211> LENGTH: 20
<212> TYPE: DNA
<213> ORGANISM: Artificial Sequence
<220> FEATURE:
<223> OTHER INFORMATION: Oligonucleotide

<400> SEQUENCE: 160
aattccttct tcacccagca                                                   20

<210> SEQ ID NO 161
<211> LENGTH: 20
<212> TYPE: DNA
<213> ORGANISM: Artificial Sequence
<220> FEATURE:
<223> OTHER INFORMATION: Oligonucleotide

<400> SEQUENCE: 161
tgctccttcc ctcacctcca                                                   20

<210> SEQ ID NO 162
<211> LENGTH: 20
<212> TYPE: DNA
<213> ORGANISM: Artificial Sequence
<220> FEATURE:
<223> OTHER INFORMATION: Oligonucleotide

<400> SEQUENCE: 162
tcactgcaaa agcctcctcc                                                   20

<210> SEQ ID NO 163
<211> LENGTH: 20
<212> TYPE: DNA
<213> ORGANISM: Artificial Sequence
<220> FEATURE:
<223> OTHER INFORMATION: Oligonucleotide

<400> SEQUENCE: 163
aaatcagcag cctcatgcca                                                   20

<210> SEQ ID NO 164
<211> LENGTH: 20
<212> TYPE: DNA
<213> ORGANISM: Artificial Sequence
<220> FEATURE:
<223> OTHER INFORMATION: Oligonucleotide

<400> SEQUENCE: 164
```
taggtcctgc tccaaaatag                                                    20

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
atcatgcctc ctctgactct                                                    20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
ttggaacaga aactctgaag                                                    20

<210> SEQ ID NO 167
<211> LENGTH: 20
<212> TYPE: DNA
<213> ORGANISM: Artificial Sequence
<220> FEATURE:
<223> OTHER INFORMATION: Oligonucleotide

<400> SEQUENCE: 167
tcctccatct acttagtttg                                                    20

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
ggtccccatt tcagatgatg                                                    20

<210> SEQ ID NO 169
<211> LENGTH: 20
<212> TYPE: DNA
<213> ORGANISM: Artificial Sequence
<220> FEATURE:
<223> OTHER INFORMATION: Oligonucleotide

<400> SEQUENCE: 169
ccctttcctc ttgaaagaac                                                    20

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide

<400> SEQUENCE: 170
aacgaatctg ctttccctgt                                                    20

<210> SEQ ID NO 171
<211> LENGTH: 20
<212> TYPE: DNA
<213> ORGANISM: Artificial Sequence

```
<220> FEATURE:
<223> OTHER INFORMATION: Oligonucleotide

<400> SEQUENCE: 171
gcacagacat ctccaaaaga                                                   20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide

<400> SEQUENCE: 172
agaattgttc tcctcgtcgc                                                   20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide

<400> SEQUENCE: 173
agtacaaata cctagggctg                                                   20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
acagcctagg aaacctcttt                                                   20

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
tctttaggag ccacagccaa                                                   20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
ttttcagcac cgaggacagt                                                   20

<210> SEQ ID NO 177
<211> LENGTH: 20
<212> TYPE: DNA
<213> ORGANISM: Artificial Sequence
<220> FEATURE:
<223> OTHER INFORMATION: Oligonucleotide

<400> SEQUENCE: 177
agagcaactc gcctctgtac                                                   20
```

<210> SEQ ID NO 178
<211> LENGTH: 20
<212> TYPE: DNA
<213> ORGANISM: Artificial Sequence
<220> FEATURE:
<223> OTHER INFORMATION: Oligonucleotide

<400> SEQUENCE: 178
tttgtctcag tagcctctag                                        20

<210> SEQ ID NO 179
<211> LENGTH: 20
<212> TYPE: DNA
<213> ORGANISM: Artificial Sequence
<220> FEATURE:
<223> OTHER INFORMATION: Oligonucleotide

<400> SEQUENCE: 179
aaatctaggt acctcggctt                                        20

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide

<400> SEQUENCE: 180
gcagaataga actcctcgat                                        20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
tctaaccccc tttcacaaac                                        20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
tcctattatc ttcgcctcca                                        20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
gcttcctaaa cattagcacc                                        20

<210> SEQ ID NO 184
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 184
tcccctcgtg ttatctttca                                              20

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
cggtggtttt tctatccact                                              20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186 cgcttttcc caattcactt                                               20

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide

<400> SEQUENCE: 187
gagtaccaaa actcatgact                                              20

<210> SEQ ID NO 188
<211> LENGTH: 20
<212> TYPE: DNA
<213> ORGANISM: Artificial Sequence
<220> FEATURE:
<223> OTHER INFORMATION: Oligonucleotide

<400> SEQUENCE: 188
cttcacaact ctaagcttgc                                              20

<210> SEQ ID NO 189
<211> LENGTH: 20
<212> TYPE: DNA
<213> ORGANISM: Artificial Sequence
<220> FEATURE:
<223> OTHER INFORMATION: Oligonucleotide

<400> SEQUENCE: 189
cgtaactatt cacaggagtc                                              20

<210> SEQ ID NO 190
<211> LENGTH: 20
<212> TYPE: DNA
<213> ORGANISM: Artificial Sequence
<220> FEATURE:
<223> OTHER INFORMATION: Oligonucleotide

<400> SEQUENCE: 190
cttcttcttc ctcttcttct                                              20

<210> SEQ ID NO 191
```

-continued

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 191
tcttcttctt cttcttcttc                                              20

<210> SEQ ID NO 192
<211> LENGTH: 20
<212> TYPE: DNA
<213> ORGANISM: Artificial Sequence
<220> FEATURE:
<223> OTHER INFORMATION: Oligonucleotide

<400> SEQUENCE: 192
cttcttcttc ttcttcttct                                              20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide

<400> SEQUENCE: 193
ggtcttcttc ttcttcttct                                              20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide

<400> SEQUENCE: 194
cccagacatg gaaaagaata                                              20

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide

<400> SEQUENCE: 195
caactcgtat tcacttccag                                              20

<210> SEQ ID NO 196
<211> LENGTH: 20
<212> TYPE: DNA
<213> ORGANISM: Artificial Sequence
<220> FEATURE:
<223> OTHER INFORMATION: Oligonucleotide

<400> SEQUENCE: 196
gacacagagt agtaactaga                                              20

<210> SEQ ID NO 197
<211> LENGTH: 20
<212> TYPE: DNA
<213> ORGANISM: Artificial Sequence
<220> FEATURE:
<223> OTHER INFORMATION: Oligonucleotide

<400> SEQUENCE: 197
```
ccacaaaaaa acctacaacg                      20

<210> SEQ ID NO 198
<211> LENGTH: 20
<212> TYPE: DNA
<213> ORGANISM: Artificial Sequence
<220> FEATURE:
<223> OTHER INFORMATION: Oligonucleotide

<400> SEQUENCE: 198
caggtagcaa agacaaggtt                      20

<210> SEQ ID NO 199
<211> LENGTH: 20
<212> TYPE: DNA
<213> ORGANISM: Artificial Sequence
<220> FEATURE:
<223> OTHER INFORMATION: Oligonucleotide

<400> SEQUENCE: 199
tgaggccaaa ttggttgagt                      20

<210> SEQ ID NO 200
<211> LENGTH: 20
<212> TYPE: DNA
<213> ORGANISM: Artificial Sequence
<220> FEATURE:
<223> OTHER INFORMATION: Oligonucleotide

<400> SEQUENCE: 200
acaaagctga tgccctggca                      20

<210> SEQ ID NO 201
<211> LENGTH: 20
<212> TYPE: DNA
<213> ORGANISM: Artificial Sequence
<220> FEATURE:
<223> OTHER INFORMATION: Oligonucleotide

<400> SEQUENCE: 201 ttttcccccca tagacaagct                     20

<210> SEQ ID NO 202
<211> LENGTH: 20
<212> TYPE: DNA
<213> ORGANISM: Artificial Sequence
<220> FEATURE:
<223> OTHER INFORMATION: Oligonucleotide

<400> SEQUENCE: 202
cattcaacaa tgcacactgc                      20

<210> SEQ ID NO 203
<211> LENGTH: 20
<212> TYPE: DNA
<213> ORGANISM: Artificial Sequence
<220> FEATURE:
<223> OTHER INFORMATION: Oligonucleotide

<400> SEQUENCE: 203
ttttccgccc catttccttt                      20

<210> SEQ ID NO 204
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 204
ccatcaccac tgtagaaaga                                         20

<210> SEQ ID NO 205
<211> LENGTH: 20
<212> TYPE: DNA
<213> ORGANISM: Artificial Sequence
<220> FEATURE:
<223> OTHER INFORMATION: Oligonucleotide

<400> SEQUENCE: 205
ttggattcca catcacagct                                         20

<210> SEQ ID NO 206
<211> LENGTH: 20
<212> TYPE: DNA
<213> ORGANISM: Artificial Sequence
<220> FEATURE:
<223> OTHER INFORMATION: Oligonucleotide

<400> SEQUENCE: 206
aaatagccct ggagtcatga                                         20

<210> SEQ ID NO 207
<211> LENGTH: 20
<212> TYPE: DNA
<213> ORGANISM: Artificial Sequence
<220> FEATURE:
<223> OTHER INFORMATION: Oligonucleotide

<400> SEQUENCE: 207
tgtaagggta aaggggggaat                                        20

<210> SEQ ID NO 208
<211> LENGTH: 20
<212> TYPE: DNA
<213> ORGANISM: Artificial Sequence
<220> FEATURE:
<223> OTHER INFORMATION: Oligonucleotide

<400> SEQUENCE: 208
ggatgaacta agaaaagagg                                         20

<210> SEQ ID NO 209
<211> LENGTH: 20
<212> TYPE: DNA
<213> ORGANISM: Artificial Sequence
<220> FEATURE:
<223> OTHER INFORMATION: Oligonucleotide

<400> SEQUENCE: 209
ctaatattcc ctccctagtg                                         20

<210> SEQ ID NO 210
<211> LENGTH: 20
<212> TYPE: DNA
<213> ORGANISM: Artificial Sequence
<220> FEATURE:
<223> OTHER INFORMATION: Oligonucleotide

<400> SEQUENCE: 210
cccgtttcat caataaccag                                         20
```

<210> SEQ ID NO 211
<211> LENGTH: 20
<212> TYPE: DNA
<213> ORGANISM: Artificial Sequence
<220> FEATURE:
<223> OTHER INFORMATION: Oligonucleotide

<400> SEQUENCE: 211
ggctgcaatc agtatttctc                                          20

<210> SEQ ID NO 212
<211> LENGTH: 20
<212> TYPE: DNA
<213> ORGANISM: Artificial Sequence
<220> FEATURE:
<223> OTHER INFORMATION: Oligonucleotide

<400> SEQUENCE: 212
gggaagcaaa ttggaatctg                                          20

<210> SEQ ID NO 213
<211> LENGTH: 20
<212> TYPE: DNA
<213> ORGANISM: Artificial Sequence
<220> FEATURE:
<223> OTHER INFORMATION: Oligonucleotide

<400> SEQUENCE: 213
tcaggtccag acacaatatc                                          20

<210> SEQ ID NO 214
<211> LENGTH: 20
<212> TYPE: DNA
<213> ORGANISM: Artificial Sequence
<220> FEATURE:
<223> OTHER INFORMATION: Oligonucleotide

<400> SEQUENCE: 214
tagatatgga gacgttcgca                                          20

<210> SEQ ID NO 215
<211> LENGTH: 20
<212> TYPE: DNA
<213> ORGANISM: Artificial Sequence
<220> FEATURE:
<223> OTHER INFORMATION: Oligonucleotide

<400> SEQUENCE: 215
caaaacaaag tcacaacagc                                          20

<210> SEQ ID NO 216
<211> LENGTH: 20
<212> TYPE: DNA
<213> ORGANISM: Artificial Sequence
<220> FEATURE:
<223> OTHER INFORMATION: Oligonucleotide

<400> SEQUENCE: 216
caaacacaat gtcaagttcg                                          20

<210> SEQ ID NO 217
<211> LENGTH: 20
<212> TYPE: DNA
<213> ORGANISM: Artificial Sequence
<220> FEATURE:

<223> OTHER INFORMATION: Oligonucleotide

<400> SEQUENCE: 217
caaaaagaaa gttgtcggcg                                          20

<210> SEQ ID NO 218
<211> LENGTH: 20
<212> TYPE: DNA
<213> ORGANISM: Artificial Sequence
<220> FEATURE:
<223> OTHER INFORMATION: Oligonucleotide

<400> SEQUENCE: 218
gtttgcagaa cactcgtgtg                                          20

<210> SEQ ID NO 219
<211> LENGTH: 20
<212> TYPE: DNA
<213> ORGANISM: Artificial Sequence
<220> FEATURE:
<223> OTHER INFORMATION: Oligonucleotide

<400> SEQUENCE: 219
gctcacctgg acgcagggac                                          20

<210> SEQ ID NO 220
<211> LENGTH: 20
<212> TYPE: DNA
<213> ORGANISM: Artificial Sequence
<220> FEATURE:
<223> OTHER INFORMATION: Oligonucleotide

<400> SEQUENCE: 220
gcaggacact aactctccgg                                          20

<210> SEQ ID NO 221
<211> LENGTH: 20
<212> TYPE: DNA
<213> ORGANISM: Artificial Sequence
<220> FEATURE:
<223> OTHER INFORMATION: Oligonucleotide

<400> SEQUENCE: 221
ggacctccta agtccggggc                                          20

<210> SEQ ID NO 222
<211> LENGTH: 20
<212> TYPE: DNA
<213> ORGANISM: Artificial Sequence
<220> FEATURE:
<223> OTHER INFORMATION: Oligonucleotide

<400> SEQUENCE: 222
gttccgagaa aggggtctct                                          20

<210> SEQ ID NO 223
<211> LENGTH: 20
<212> TYPE: DNA
<213> ORGANISM: Artificial Sequence
<220> FEATURE:
<223> OTHER INFORMATION: Oligonucleotide

<400> SEQUENCE: 223
cagtcaggag ccagcaagag                                          20

```
<210> SEQ ID NO 224
<211> LENGTH: 20
<212> TYPE: DNA
<213> ORGANISM: Artificial Sequence
<220> FEATURE:
<223> OTHER INFORMATION: Oligonucleotide

<400> SEQUENCE: 224
gttcttctac tcgccttctg                                               20

<210> SEQ ID NO 225
<211> LENGTH: 20
<212> TYPE: DNA
<213> ORGANISM: Artificial Sequence
<220> FEATURE:
<223> OTHER INFORMATION: Oligonucleotide

<400> SEQUENCE: 225
aggtcctaaa atccaactgc                                               20

<210> SEQ ID NO 226
<211> LENGTH: 20
<212> TYPE: DNA
<213> ORGANISM: Artificial Sequence
<220> FEATURE:
<223> OTHER INFORMATION: Oligonucleotide

<400> SEQUENCE: 226
ggctaaagct tctgatgctt                                               20

<210> SEQ ID NO 227
<211> LENGTH: 20
<212> TYPE: DNA
<213> ORGANISM: Artificial Sequence
<220> FEATURE:
<223> OTHER INFORMATION: Oligonucleotide

<400> SEQUENCE: 227
ctagggtgta gggctttctt                                               20

<210> SEQ ID NO 228
<211> LENGTH: 20
<212> TYPE: DNA
<213> ORGANISM: Artificial Sequence
<220> FEATURE:
<223> OTHER INFORMATION: Oligonucleotide

<400> SEQUENCE: 228
ccagggaact aagtgttcca                                               20

<210> SEQ ID NO 229
<211> LENGTH: 20
<212> TYPE: DNA
<213> ORGANISM: Artificial Sequence
<220> FEATURE:
<223> OTHER INFORMATION: Oligonucleotide

<400> SEQUENCE: 229
ttgcttctac acagaatagc                                               20

<210> SEQ ID NO 230
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 230
tgacgaattc ctttgtctga                                              20

<210> SEQ ID NO 231
<211> LENGTH: 20
<212> TYPE: DNA
<213> ORGANISM: Artificial Sequence
<220> FEATURE:
<223> OTHER INFORMATION: Oligonucleotide

<400> SEQUENCE: 231
tggctagaat ctcatgcatt                                              20

<210> SEQ ID NO 232
<211> LENGTH: 20
<212> TYPE: DNA
<213> ORGANISM: Artificial Sequence
<220> FEATURE:
<223> OTHER INFORMATION: Oligonucleotide

<400> SEQUENCE: 232
aaagacagtc tcatacagac                                              20

<210> SEQ ID NO 233
<211> LENGTH: 20
<212> TYPE: DNA
<213> ORGANISM: Artificial Sequence
<220> FEATURE:
<223> OTHER INFORMATION: Oligonucleotide

<400> SEQUENCE: 233
ctccagcttt acaagatgct                                              20

<210> SEQ ID NO 234
<211> LENGTH: 20
<212> TYPE: DNA
<213> ORGANISM: Artificial Sequence
<220> FEATURE:
<223> OTHER INFORMATION: Oligonucleotide

<400> SEQUENCE: 234
tccaaccatg gaggattgtt                                              20

<210> SEQ ID NO 235
<211> LENGTH: 20
<212> TYPE: DNA
<213> ORGANISM: Artificial Sequence
<220> FEATURE:
<223> OTHER INFORMATION: Oligonucleotide

<400> SEQUENCE: 235
tggtataacc cacatacaga                                              20

<210> SEQ ID NO 236
<211> LENGTH: 20
<212> TYPE: DNA
<213> ORGANISM: Artificial Sequence
<220> FEATURE:
<223> OTHER INFORMATION: Oligonucleotide

<400> SEQUENCE: 236
tttccaagga aaaacatgt                                               20

<210> SEQ ID NO 237
<211> LENGTH: 20
```

```
<212> TYPE: DNA
<213> ORGANISM: Artificial Sequence
<220> FEATURE:
<223> OTHER INFORMATION: Oligonucleotide

<400> SEQUENCE: 237
attgcaattt tctgcagtct                                                20

<210> SEQ ID NO 238
<211> LENGTH: 20
<212> TYPE: DNA
<213> ORGANISM: Artificial Sequence
<220> FEATURE:
<223> OTHER INFORMATION: Oligonucleotide

<400> SEQUENCE: 238
cgcctttttc aaggactaga                                                20

<210> SEQ ID NO 239
<211> LENGTH: 20
<212> TYPE: DNA
<213> ORGANISM: Artificial Sequence
<220> FEATURE:
<223> OTHER INFORMATION: Oligonucleotide

<400> SEQUENCE: 239
ttaataacag cttgagagca                                                20

<210> SEQ ID NO 240
<211> LENGTH: 20
<212> TYPE: DNA
<213> ORGANISM: Artificial Sequence
<220> FEATURE:
<223> OTHER INFORMATION: Oligonucleotide

<400> SEQUENCE: 240
cttcaaagtg cagtttagta                                                20

<210> SEQ ID NO 241
<211> LENGTH: 20
<212> TYPE: DNA
<213> ORGANISM: Artificial Sequence
<220> FEATURE:
<223> OTHER INFORMATION: Oligonucleotide

<400> SEQUENCE: 241
gtccaagagc tcacctagga                                                20

<210> SEQ ID NO 242
<211> LENGTH: 20
<212> TYPE: DNA
<213> ORGANISM: Artificial Sequence
<220> FEATURE:
<223> OTHER INFORMATION: Oligonucleotide

<400> SEQUENCE: 242
aggaagtcat ttatttccag                                                20

<210> SEQ ID NO 243
<211> LENGTH: 20
<212> TYPE: DNA
<213> ORGANISM: Artificial Sequence
<220> FEATURE:
<223> OTHER INFORMATION: Oligonucleotide

<400> SEQUENCE: 243
```
tcaaaattta gaaggccaat                                                         20

<210> SEQ ID NO 244
<211> LENGTH: 20
<212> TYPE: DNA
<213> ORGANISM: Artificial Sequence
<220> FEATURE:
<223> OTHER INFORMATION: Oligonucleotide

<400> SEQUENCE: 244
aagaaacaca aacgcgagta                                                         20

<210> SEQ ID NO 245
<211> LENGTH: 20
<212> TYPE: DNA
<213> ORGANISM: Artificial Sequence
<220> FEATURE:
<223> OTHER INFORMATION: Oligonucleotide

<400> SEQUENCE: 245
agaggaaact atcaaaaaca                                                         20

<210> SEQ ID NO 246
<211> LENGTH: 20
<212> TYPE: DNA
<213> ORGANISM: Artificial Sequence
<220> FEATURE:
<223> OTHER INFORMATION: Oligonucleotide

<400> SEQUENCE: 246
cctgtcactc ataaacgaga                                                         20

<210> SEQ ID NO 247
<211> LENGTH: 20
<212> TYPE: DNA
<213> ORGANISM: Artificial Sequence
<220> FEATURE:
<223> OTHER INFORMATION: Oligonucleotide

<400> SEQUENCE: 247
atagcctggc cacctagttc                                                         20

<210> SEQ ID NO 248
<211> LENGTH: 20
<212> TYPE: DNA
<213> ORGANISM: Artificial Sequence
<220> FEATURE:
<223> OTHER INFORMATION: Oligonucleotide

<400> SEQUENCE: 248
aggagccaag catacaagag                                                         20

<210> SEQ ID NO 249
<211> LENGTH: 20
<212> TYPE: DNA
<213> ORGANISM: Artificial Sequence
<220> FEATURE:
<223> OTHER INFORMATION: Oligonucleotide

<400> SEQUENCE: 249
ctggtggcca accaaggaac                                                         20

<210> SEQ ID NO 250
<211> LENGTH: 20
<212> TYPE: DNA
<213> ORGANISM: Artificial Sequence

```
<220> FEATURE:
<223> OTHER INFORMATION: Oligonucleotide

<400> SEQUENCE: 250
gtaaccaaaa aacagtatgc                                               20

<210> SEQ ID NO 251
<211> LENGTH: 20
<212> TYPE: DNA
<213> ORGANISM: Artificial Sequence
<220> FEATURE:
<223> OTHER INFORMATION: Oligonucleotide

<400> SEQUENCE: 251
caaaatgaag acagggtcaa                                               20

<210> SEQ ID NO 252
<211> LENGTH: 20
<212> TYPE: DNA
<213> ORGANISM: Artificial Sequence
<220> FEATURE:
<223> OTHER INFORMATION: Oligonucleotide

<400> SEQUENCE: 252
aagcaaagat agacttgacc                                               20

<210> SEQ ID NO 253
<211> LENGTH: 20
<212> TYPE: DNA
<213> ORGANISM: Artificial Sequence
<220> FEATURE:
<223> OTHER INFORMATION: Oligonucleotide

<400> SEQUENCE: 253
acaagcttta tgttctgtgt                                               20

<210> SEQ ID NO 254
<211> LENGTH: 20
<212> TYPE: DNA
<213> ORGANISM: Artificial Sequence
<220> FEATURE:
<223> OTHER INFORMATION: Oligonucleotide

<400> SEQUENCE: 254
ctcaaagatt tgtggaagtc                                               20

<210> SEQ ID NO 255
<211> LENGTH: 20
<212> TYPE: DNA
<213> ORGANISM: Artificial Sequence
<220> FEATURE:
<223> OTHER INFORMATION: Oligonucleotide

<400> SEQUENCE: 255
tgttgttgac aaatatgccc                                               20

<210> SEQ ID NO 256
<211> LENGTH: 20
<212> TYPE: DNA
<213> ORGANISM: Artificial Sequence
<220> FEATURE:
<223> OTHER INFORMATION: Oligonucleotide

<400> SEQUENCE: 256
tcgatgaatg tcagaaatct                                               20
```

```
<210> SEQ ID NO 257
<211> LENGTH: 20
<212> TYPE: DNA
<213> ORGANISM: Artificial Sequence
<220> FEATURE:
<223> OTHER INFORMATION: Oligonucleotide

<400> SEQUENCE: 257
aatgcagagc tgatgtcaat                                                    20

<210> SEQ ID NO 258
<211> LENGTH: 20
<212> TYPE: DNA
<213> ORGANISM: Artificial Sequence
<220> FEATURE:
<223> OTHER INFORMATION: Oligonucleotide

<400> SEQUENCE: 258
gtataactcc aaagaagtca                                                    20

<210> SEQ ID NO 259
<211> LENGTH: 20
<212> TYPE: DNA
<213> ORGANISM: Artificial Sequence
<220> FEATURE:
<223> OTHER INFORMATION: Oligonucleotide

<400> SEQUENCE: 259
aacaaaaagc ccaaagacag                                                    20

<210> SEQ ID NO 260
<211> LENGTH: 20
<212> TYPE: DNA
<213> ORGANISM: Artificial Sequence
<220> FEATURE:
<223> OTHER INFORMATION: Oligonucleotide

<400> SEQUENCE: 260
gctggtcact agcaagttta                                                    20

<210> SEQ ID NO 261
<211> LENGTH: 20
<212> TYPE: DNA
<213> ORGANISM: Artificial Sequence
<220> FEATURE:
<223> OTHER INFORMATION: Oligonucleotide

<400> SEQUENCE: 261
gactatgcag caaaacagtt                                                    20

<210> SEQ ID NO 262
<211> LENGTH: 20
<212> TYPE: DNA
<213> ORGANISM: Artificial Sequence
<220> FEATURE:
<223> OTHER INFORMATION: Oligonucleotide

<400> SEQUENCE: 262
atactcaacc aattggcagc                                                    20

<210> SEQ ID NO 263
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 263
gcttaggttg gcaaaacaag                                               20

<210> SEQ ID NO 264
<211> LENGTH: 20
<212> TYPE: DNA
<213> ORGANISM: Artificial Sequence
<220> FEATURE:
<223> OTHER INFORMATION: Oligonucleotide

<400> SEQUENCE: 264
gtaaagtctc aattttctgc                                               20

<210> SEQ ID NO 265
<211> LENGTH: 20
<212> TYPE: DNA
<213> ORGANISM: Artificial Sequence
<220> FEATURE:
<223> OTHER INFORMATION: Oligonucleotide

<400> SEQUENCE: 265
tcctcgccct tgctcaccat                                               20

<210> SEQ ID NO 266
<211> LENGTH: 20
<212> TYPE: DNA
<213> ORGANISM: Artificial Sequence
<220> FEATURE:
<223> OTHER INFORMATION: Oligonucleotide

<400> SEQUENCE: 266
atgggcacca ccccggtgaa                                               20

<210> SEQ ID NO 267
<211> LENGTH: 20
<212> TYPE: DNA
<213> ORGANISM: Artificial Sequence
<220> FEATURE:
<223> OTHER INFORMATION: Oligonucleotide

<400> SEQUENCE: 267
ttacgtcgcc gtccagctcg                                               20

<210> SEQ ID NO 268
<211> LENGTH: 20
<212> TYPE: DNA
<213> ORGANISM: Artificial Sequence
<220> FEATURE:
<223> OTHER INFORMATION: Oligonucleotide

<400> SEQUENCE: 268
gacacgctga acttgtggcc                                               20

<210> SEQ ID NO 269
<211> LENGTH: 20
<212> TYPE: DNA
<213> ORGANISM: Artificial Sequence
<220> FEATURE:
<223> OTHER INFORMATION: Oligonucleotide

<400> SEQUENCE: 269
ggcatcgccc tcgccctcgc                                               20

<210> SEQ ID NO 270
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 270
tcagggtcag cttgccgtag                                           20

<210> SEQ ID NO 271
<211> LENGTH: 20
<212> TYPE: DNA
<213> ORGANISM: Artificial Sequence
<220> FEATURE:
<223> OTHER INFORMATION: Oligonucleotide

<400> SEQUENCE: 271
ttgccggtgg tgcagatgaa                                           20

<210> SEQ ID NO 272
<211> LENGTH: 20
<212> TYPE: DNA
<213> ORGANISM: Artificial Sequence
<220> FEATURE:
<223> OTHER INFORMATION: Oligonucleotide

<400> SEQUENCE: 272
ggtgggccag ggcacgggca                                           20

<210> SEQ ID NO 273
<211> LENGTH: 20
<212> TYPE: DNA
<213> ORGANISM: Artificial Sequence
<220> FEATURE:
<223> OTHER INFORMATION: Oligonucleotide

<400> SEQUENCE: 273
cgtaggtgaa ggtggtcacg                                           20

<210> SEQ ID NO 274
<211> LENGTH: 20
<212> TYPE: DNA
<213> ORGANISM: Artificial Sequence
<220> FEATURE:
<223> OTHER INFORMATION: Oligonucleotide

<400> SEQUENCE: 274
tagcggctga agcactgcac                                           20

<210> SEQ ID NO 275
<211> LENGTH: 20
<212> TYPE: DNA
<213> ORGANISM: Artificial Sequence
<220> FEATURE:
<223> OTHER INFORMATION: Oligonucleotide

<400> SEQUENCE: 275
gtgctgcttc atgtggtcgg                                           20

<210> SEQ ID NO 276
<211> LENGTH: 20
<212> TYPE: DNA
<213> ORGANISM: Artificial Sequence
<220> FEATURE:
<223> OTHER INFORMATION: Oligonucleotide

<400> SEQUENCE: 276
```
gcatggcgga cttgaagaag                                          20

<210> SEQ ID NO 277
<211> LENGTH: 20
<212> TYPE: DNA
<213> ORGANISM: Artificial Sequence
<220> FEATURE:
<223> OTHER INFORMATION: Oligonucleotide

<400> SEQUENCE: 277
cgctcctgga cgtagccttc                                          20

<210> SEQ ID NO 278
<211> LENGTH: 20
<212> TYPE: DNA
<213> ORGANISM: Artificial Sequence
<220> FEATURE:
<223> OTHER INFORMATION: Oligonucleotide

<400> SEQUENCE: 278
gtcgtccttg aagaagatgg                                          20

<210> SEQ ID NO 279
<211> LENGTH: 20
<212> TYPE: DNA
<213> ORGANISM: Artificial Sequence
<220> FEATURE:
<223> OTHER INFORMATION: Oligonucleotide

<400> SEQUENCE: 279
cggcgcgggt cttgtagttg                                          20

<210> SEQ ID NO 280
<211> LENGTH: 20
<212> TYPE: DNA
<213> ORGANISM: Artificial Sequence
<220> FEATURE:
<223> OTHER INFORMATION: Oligonucleotide

<400> SEQUENCE: 280
gtgtcgccct cgaacttcac                                          20

<210> SEQ ID NO 281
<211> LENGTH: 20
<212> TYPE: DNA
<213> ORGANISM: Artificial Sequence
<220> FEATURE:
<223> OTHER INFORMATION: Oligonucleotide

<400> SEQUENCE: 281
ttcagctcga tgcggttcac                                          20

<210> SEQ ID NO 282
<211> LENGTH: 20
<212> TYPE: DNA
<213> ORGANISM: Artificial Sequence
<220> FEATURE:
<223> OTHER INFORMATION: Oligonucleotide

<400> SEQUENCE: 282
cgtcctcctt gaagtcgatg                                          20

<210> SEQ ID NO 283
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 283
agcttgtgcc ccaggatgtt                                              20

<210> SEQ ID NO 284
<211> LENGTH: 20
<212> TYPE: DNA
<213> ORGANISM: Artificial Sequence
<220> FEATURE:
<223> OTHER INFORMATION: Oligonucleotide

<400> SEQUENCE: 284
gtggctgttg tagttgtact                                              20

<210> SEQ ID NO 285
<211> LENGTH: 20
<212> TYPE: DNA
<213> ORGANISM: Artificial Sequence
<220> FEATURE:
<223> OTHER INFORMATION: Oligonucleotide

<400> SEQUENCE: 285
tgtcggccat gatatagacg                                              20

<210> SEQ ID NO 286
<211> LENGTH: 20
<212> TYPE: DNA
<213> ORGANISM: Artificial Sequence
<220> FEATURE:
<223> OTHER INFORMATION: Oligonucleotide

<400> SEQUENCE: 286
accttgatgc cgttcttctg                                              20

<210> SEQ ID NO 287
<211> LENGTH: 20
<212> TYPE: DNA
<213> ORGANISM: Artificial Sequence
<220> FEATURE:
<223> OTHER INFORMATION: Oligonucleotide

<400> SEQUENCE: 287
tgttgtggcg gatcttgaag                                              20

<210> SEQ ID NO 288
<211> LENGTH: 20
<212> TYPE: DNA
<213> ORGANISM: Artificial Sequence
<220> FEATURE:
<223> OTHER INFORMATION: Oligonucleotide

<400> SEQUENCE: 288
agctgcacgc tgccgtcctc                                              20

<210> SEQ ID NO 289
<211> LENGTH: 20
<212> TYPE: DNA
<213> ORGANISM: Artificial Sequence
<220> FEATURE:
<223> OTHER INFORMATION: Oligonucleotide

<400> SEQUENCE: 289
tgttctgctg gtagtggtcg                                              20
```

```
<210> SEQ ID NO 290
<211> LENGTH: 20
<212> TYPE: DNA
<213> ORGANISM: Artificial Sequence
<220> FEATURE:
<223> OTHER INFORMATION: Oligonucleotide

<400> SEQUENCE: 290
cacggggccg tcgccgatgg                                          20

<210> SEQ ID NO 291
<211> LENGTH: 20
<212> TYPE: DNA
<213> ORGANISM: Artificial Sequence
<220> FEATURE:
<223> OTHER INFORMATION: Oligonucleotide

<400> SEQUENCE: 291
ctcaggtagt ggttgtcggg                                          20

<210> SEQ ID NO 292
<211> LENGTH: 20
<212> TYPE: DNA
<213> ORGANISM: Artificial Sequence
<220> FEATURE:
<223> OTHER INFORMATION: Oligonucleotide

<400> SEQUENCE: 292
ctttgctcag ggcggactgg                                          20

<210> SEQ ID NO 293
<211> LENGTH: 20
<212> TYPE: DNA
<213> ORGANISM: Artificial Sequence
<220> FEATURE:
<223> OTHER INFORMATION: Oligonucleotide

<400> SEQUENCE: 293
tgatcgcgct tctcgttggg                                          20

<210> SEQ ID NO 294
<211> LENGTH: 20
<212> TYPE: DNA
<213> ORGANISM: Artificial Sequence
<220> FEATURE:
<223> OTHER INFORMATION: Oligonucleotide

<400> SEQUENCE: 294
cacgaactcc agcaggacca                                          20

<210> SEQ ID NO 295
<211> LENGTH: 20
<212> TYPE: DNA
<213> ORGANISM: Artificial Sequence
<220> FEATURE:
<223> OTHER INFORMATION: Oligonucleotide

<400> SEQUENCE: 295
cgagagtgat cccggcggcg                                          20

<210> SEQ ID NO 296
<211> LENGTH: 20
<212> TYPE: DNA
<213> ORGANISM: Artificial Sequence
<220> FEATURE:
```

<223> OTHER INFORMATION: Oligonucleotide

<400> SEQUENCE: 296
cacttgtaca gctcgtccat                                           20

<210> SEQ ID NO 297
<211> LENGTH: 20
<212> TYPE: DNA
<213> ORGANISM: Artificial Sequence
<220> FEATURE:
<223> OTHER INFORMATION: Oligonucleotide

<400> SEQUENCE: 297
ctccaaaaac ctgacttcgc                                           20

<210> SEQ ID NO 298
<211> LENGTH: 20
<212> TYPE: DNA
<213> ORGANISM: Artificial Sequence
<220> FEATURE:
<223> OTHER INFORMATION: Oligonucleotide

<400> SEQUENCE: 298
tgtcctaatt ggcctgatcc                                           20

<210> SEQ ID NO 299
<211> LENGTH: 20
<212> TYPE: DNA
<213> ORGANISM: Artificial Sequence
<220> FEATURE:
<223> OTHER INFORMATION: Oligonucleotide

<400> SEQUENCE: 299
ccacccaaca tgctctcttt                                           20

<210> SEQ ID NO 300
<211> LENGTH: 20
<212> TYPE: DNA
<213> ORGANISM: Artificial Sequence
<220> FEATURE:
<223> OTHER INFORMATION: Oligonucleotide

<400> SEQUENCE: 300
ccatcattta ccagccctgt                                           20

<210> SEQ ID NO 301
<211> LENGTH: 20
<212> TYPE: DNA
<213> ORGANISM: Artificial Sequence
<220> FEATURE:
<223> OTHER INFORMATION: Oligonucleotide

<400> SEQUENCE: 301
gctcattgcc ctgcagatag                                           20

<210> SEQ ID NO 302
<211> LENGTH: 20
<212> TYPE: DNA
<213> ORGANISM: Artificial Sequence
<220> FEATURE:
<223> OTHER INFORMATION: Oligonucleotide

<400> SEQUENCE: 302
tgatcctcca gtaaccgcat                                           20

```
<210> SEQ ID NO 303
<211> LENGTH: 20
<212> TYPE: DNA
<213> ORGANISM: Artificial Sequence
<220> FEATURE:
<223> OTHER INFORMATION: Oligonucleotide

<400> SEQUENCE: 303
agacctgcat ttccttccct                                              20

<210> SEQ ID NO 304
<211> LENGTH: 20
<212> TYPE: DNA
<213> ORGANISM: Artificial Sequence
<220> FEATURE:
<223> OTHER INFORMATION: Oligonucleotide

<400> SEQUENCE: 304
actgtggctc tgttgccttt                                              20

<210> SEQ ID NO 305
<211> LENGTH: 20
<212> TYPE: DNA
<213> ORGANISM: Artificial Sequence
<220> FEATURE:
<223> OTHER INFORMATION: Oligonucleotide

<400> SEQUENCE: 305
ccctcagacc cacttcacat                                              20

<210> SEQ ID NO 306
<211> LENGTH: 20
<212> TYPE: DNA
<213> ORGANISM: Artificial Sequence
<220> FEATURE:
<223> OTHER INFORMATION: Oligonucleotide

<400> SEQUENCE: 306
cccttctgca cgtctcttct                                              20

<210> SEQ ID NO 307
<211> LENGTH: 25
<212> TYPE: DNA
<213> ORGANISM: Artificial Sequence
<220> FEATURE:
<223> OTHER INFORMATION: Oligonucleotide

<400> SEQUENCE: 307
cagtgtctat tcagaaacca cagaa                                        25

<210> SEQ ID NO 308
<211> LENGTH: 21
<212> TYPE: DNA
<213> ORGANISM: Artificial Sequence
<220> FEATURE:
<223> OTHER INFORMATION: Oligonucleotide

<400> SEQUENCE: 308
cgtgagttca ggcctactgt c                                            21

<210> SEQ ID NO 309
<211> LENGTH: 21
<212> TYPE: DNA
<213> ORGANISM: Artificial Sequence
<220> FEATURE:
<223> OTHER INFORMATION: Oligonucleotide
```

<400> SEQUENCE: 309
catgcagaga agatcaccat t 21

<210> SEQ ID NO 310
<211> LENGTH: 20
<212> TYPE: DNA
<213> ORGANISM: Artificial Sequence
<220> FEATURE:
<223> OTHER INFORMATION: Oligonucleotide

<400> SEQUENCE: 310
gggccaagtc ctcaagataa 20

<210> SEQ ID NO 311
<211> LENGTH: 22
<212> TYPE: DNA
<213> ORGANISM: Artificial Sequence
<220> FEATURE:
<223> OTHER INFORMATION: Oligonucleotide

<400> SEQUENCE: 311
tggcaattat ccattgtcat tt 22

<210> SEQ ID NO 312
<211> LENGTH: 20
<212> TYPE: DNA
<213> ORGANISM: Artificial Sequence
<220> FEATURE:
<223> OTHER INFORMATION: Oligonucleotide

<400> SEQUENCE: 312
tgtttaagag gatgcctggg 20

<210> SEQ ID NO 313
<211> LENGTH: 26
<212> TYPE: DNA
<213> ORGANISM: Artificial Sequence
<220> FEATURE:
<223> OTHER INFORMATION: Oligonucleotide

<400> SEQUENCE: 313
ttagtaatct ttggaacatc tgaaca 26

<210> SEQ ID NO 314
<211> LENGTH: 20
<212> TYPE: DNA
<213> ORGANISM: Artificial Sequence
<220> FEATURE:
<223> OTHER INFORMATION: Oligonucleotide

<400> SEQUENCE: 314
ggcactgaat acacgatggg 20

<210> SEQ ID NO 315
<211> LENGTH: 20
<212> TYPE: DNA
<213> ORGANISM: Artificial Sequence
<220> FEATURE:
<223> OTHER INFORMATION: Oligonucleotide

<400> SEQUENCE: 315
ttattgccta acccagtgcc 20

<210> SEQ ID NO 316
<211> LENGTH: 20

<212> TYPE: DNA
<213> ORGANISM: Artificial Sequence
<220> FEATURE:
<223> OTHER INFORMATION: Oligonucleotide

<400> SEQUENCE: 316
tcctatgtca acctggaccc                                           20

<210> SEQ ID NO 317
<211> LENGTH: 21
<212> TYPE: DNA
<213> ORGANISM: Artificial Sequence
<220> FEATURE:
<223> OTHER INFORMATION: Oligonucleotide

<400> SEQUENCE: 317
tcaagccttt ctgcctctac a                                         21

<210> SEQ ID NO 318
<211> LENGTH: 22
<212> TYPE: DNA
<213> ORGANISM: Artificial Sequence
<220> FEATURE:
<223> OTHER INFORMATION: Oligonucleotide

<400> SEQUENCE: 318
gacacgtgat agcacctaac ca                                        22

<210> SEQ ID NO 319
<211> LENGTH: 20
<212> TYPE: DNA
<213> ORGANISM: Artificial Sequence
<220> FEATURE:
<223> OTHER INFORMATION: Oligonucleotide

<400> SEQUENCE: 319
acatatgccg gagttggaaa                                           20

<210> SEQ ID NO 320
<211> LENGTH: 20
<212> TYPE: DNA
<213> ORGANISM: Artificial Sequence
<220> FEATURE:
<223> OTHER INFORMATION: Oligonucleotide

<400> SEQUENCE: 320
tctgggctat ctccgtgatt                                           20

<210> SEQ ID NO 321
<211> LENGTH: 20
<212> TYPE: DNA
<213> ORGANISM: Artificial Sequence
<220> FEATURE:
<223> OTHER INFORMATION: Oligonucleotide

<400> SEQUENCE: 321
gcactctcca gatccaggtg                                           20

<210> SEQ ID NO 322
<211> LENGTH: 20
<212> TYPE: DNA
<213> ORGANISM: Artificial Sequence
<220> FEATURE:
<223> OTHER INFORMATION: Oligonucleotide

<400> SEQUENCE: 322
ctggctgagt cccactcttc                                          20

<210> SEQ ID NO 323
<211> LENGTH: 20
<212> TYPE: DNA
<213> ORGANISM: Artificial Sequence
<220> FEATURE:
<223> OTHER INFORMATION: Oligonucleotide

<400> SEQUENCE: 323
aaccacattc ccaaggacaa                                          20

<210> SEQ ID NO 324
<211> LENGTH: 20
<212> TYPE: DNA
<213> ORGANISM: Artificial Sequence
<220> FEATURE:
<223> OTHER INFORMATION: Oligonucleotide

<400> SEQUENCE: 324
ggtcgggtag aaggaacctc                                          20

<210> SEQ ID NO 325
<211> LENGTH: 20
<212> TYPE: DNA
<213> ORGANISM: Artificial Sequence
<220> FEATURE:
<223> OTHER INFORMATION: Oligonucleotide

<400> SEQUENCE: 325
gtccccactt aggaatccgt                                          20

<210> SEQ ID NO 326
<211> LENGTH: 18
<212> TYPE: DNA
<213> ORGANISM: Artificial Sequence
<220> FEATURE:
<223> OTHER INFORMATION: Oligonucleotide

<400> SEQUENCE: 326
gctgctgcct ccagtgtc                                            18

<210> SEQ ID NO 327
<211> LENGTH: 18
<212> TYPE: DNA
<213> ORGANISM: Artificial Sequence
<220> FEATURE:
<223> OTHER INFORMATION: Oligonucleotide

<400> SEQUENCE: 327
actcgaagca ccgcactc                                            18

<210> SEQ ID NO 328
<211> LENGTH: 18
<212> TYPE: DNA
<213> ORGANISM: Artificial Sequence
<220> FEATURE:
<223> OTHER INFORMATION: Oligonucleotide

<400> SEQUENCE: 328
gaggggaccc ccagtgac                                            18

<210> SEQ ID NO 329
<211> LENGTH: 20
<212> TYPE: DNA
<213> ORGANISM: Artificial Sequence
<220> FEATURE:
<223> OTHER INFORMATION: Oligonucleotide

<400> SEQUENCE: 329
agcaggcttc tcgctgttac                                              20

<210> SEQ ID NO 330
<211> LENGTH: 21
<212> TYPE: DNA
<213> ORGANISM: Artificial Sequence
<220> FEATURE:
<223> OTHER INFORMATION: Oligonucleotide

<400> SEQUENCE: 330
ggagagaaag agctgcagtg a                                            21

<210> SEQ ID NO 331
<211> LENGTH: 20
<212> TYPE: DNA
<213> ORGANISM: Artificial Sequence
<220> FEATURE:
<223> OTHER INFORMATION: Oligonucleotide

<400> SEQUENCE: 331
accaccggaa cgtaactgaa                                              20

<210> SEQ ID NO 332
<211> LENGTH: 20
<212> TYPE: DNA
<213> ORGANISM: Artificial Sequence
<220> FEATURE:
<223> OTHER INFORMATION: Oligonucleotide

<400> SEQUENCE: 332
cgaaacatca tggttagggg                                              20

<210> SEQ ID NO 333
<211> LENGTH: 20
<212> TYPE: DNA
<213> ORGANISM: Artificial Sequence
<220> FEATURE:
<223> OTHER INFORMATION: Oligonucleotide

<400> SEQUENCE: 333
ggattttgcc cactgtgaac                                              20

<210> SEQ ID NO 334
<211> LENGTH: 20
<212> TYPE: DNA
<213> ORGANISM: Artificial Sequence
<220> FEATURE:
<223> OTHER INFORMATION: Oligonucleotide

<400> SEQUENCE: 334
cgggcatcta tcatgtgttg                                              20

<210> SEQ ID NO 335
<211> LENGTH: 20
<212> TYPE: DNA
<213> ORGANISM: Artificial Sequence
<220> FEATURE:
<223> OTHER INFORMATION: Oligonucleotide

<400> SEQUENCE: 335
ttcctatttg ctagcgtggg                                              20

```
<210> SEQ ID NO 336
<211> LENGTH: 20
<212> TYPE: DNA
<213> ORGANISM: Artificial Sequence
<220> FEATURE:
<223> OTHER INFORMATION: Oligonucleotide

<400> SEQUENCE: 336
atggaacagc tggaagagga                                              20

<210> SEQ ID NO 337
<211> LENGTH: 20
<212> TYPE: DNA
<213> ORGANISM: Artificial Sequence
<220> FEATURE:
<223> OTHER INFORMATION: Oligonucleotide

<400> SEQUENCE: 337
gggcaaagca atcaataacc                                              20

<210> SEQ ID NO 338
<211> LENGTH: 20
<212> TYPE: DNA
<213> ORGANISM: Artificial Sequence
<220> FEATURE:
<223> OTHER INFORMATION: Oligonucleotide

<400> SEQUENCE: 338 ttctcccta cctgccctat                                               20

<210> SEQ ID NO 339
<211> LENGTH: 20
<212> TYPE: DNA
<213> ORGANISM: Artificial Sequence
<220> FEATURE:
<223> OTHER INFORMATION: Oligonucleotide

<400> SEQUENCE: 339 taccctgct gagtacagcc                                               20

<210> SEQ ID NO 340
<211> LENGTH: 20
<212> TYPE: DNA
<213> ORGANISM: Artificial Sequence
<220> FEATURE:
<223> OTHER INFORMATION: Oligonucleotide

<400> SEQUENCE: 340
acctccaggc ttccttccta                                              20

<210> SEQ ID NO 341
<211> LENGTH: 20
<212> TYPE: DNA
<213> ORGANISM: Artificial Sequence
<220> FEATURE:
<223> OTHER INFORMATION: Oligonucleotide

<400> SEQUENCE: 341
gaggagtcag cagggcatag                                              20

<210> SEQ ID NO 342
<211> LENGTH: 20
<212> TYPE: DNA
<213> ORGANISM: Artificial Sequence
<220> FEATURE:
<223> OTHER INFORMATION: Oligonucleotide
```

<400> SEQUENCE: 342
agcttggctt tagttgcctg                                                      20

<210> SEQ ID NO 343
<211> LENGTH: 20
<212> TYPE: DNA
<213> ORGANISM: Artificial Sequence
<220> FEATURE:
<223> OTHER INFORMATION: Oligonucleotide

<400> SEQUENCE: 343
aggggcagag agaaggtcat                                                      20

<210> SEQ ID NO 344
<211> LENGTH: 19
<212> TYPE: DNA
<213> ORGANISM: Artificial Sequence
<220> FEATURE:
<223> OTHER INFORMATION: Oligonucleotide

<400> SEQUENCE: 344
aggtcttggg catctcacc                                                       19

<210> SEQ ID NO 345
<211> LENGTH: 20
<212> TYPE: DNA
<213> ORGANISM: Artificial Sequence
<220> FEATURE:
<223> OTHER INFORMATION: Oligonucleotide

<400> SEQUENCE: 345
tttggagcag gacctaatgg                                                      20

<210> SEQ ID NO 346
<211> LENGTH: 20
<212> TYPE: DNA
<213> ORGANISM: Artificial Sequence
<220> FEATURE:
<223> OTHER INFORMATION: Oligonucleotide

<400> SEQUENCE: 346
accactcaag ctagagccca                                                      20

<210> SEQ ID NO 347
<211> LENGTH: 20
<212> TYPE: DNA
<213> ORGANISM: Artificial Sequence
<220> FEATURE:
<223> OTHER INFORMATION: Oligonucleotide

<400> SEQUENCE: 347
ctgcctgcag tgacatcatc                                                      20

<210> SEQ ID NO 348
<211> LENGTH: 19
<212> TYPE: DNA
<213> ORGANISM: Artificial Sequence
<220> FEATURE:
<223> OTHER INFORMATION: Oligonucleotide

<400> SEQUENCE: 348
ctgcccatgt cctgtctgt                                                       19

<210> SEQ ID NO 349

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 349
gccaatgtga gggagttgat                                          20

<210> SEQ ID NO 350
<211> LENGTH: 20
<212> TYPE: DNA
<213> ORGANISM: Artificial Sequence
<220> FEATURE:
<223> OTHER INFORMATION: Oligonucleotide

<400> SEQUENCE: 350
catgggtatg cacacaggac                                          20

<210> SEQ ID NO 351
<211> LENGTH: 20
<212> TYPE: DNA
<213> ORGANISM: Artificial Sequence
<220> FEATURE:
<223> OTHER INFORMATION: Oligonucleotide

<400> SEQUENCE: 351
ctggacttgg gctcacagat                                          20

<210> SEQ ID NO 352
<211> LENGTH: 20
<212> TYPE: DNA
<213> ORGANISM: Artificial Sequence
<220> FEATURE:
<223> OTHER INFORMATION: Oligonucleotide

<400> SEQUENCE: 352
gctgagtggg aaacaactcc                                          20

<210> SEQ ID NO 353
<211> LENGTH: 20
<212> TYPE: DNA
<213> ORGANISM: Artificial Sequence
<220> FEATURE:
<223> OTHER INFORMATION: Oligonucleotide

<400> SEQUENCE: 353
tctgacctcc accaggattc                                          20

<210> SEQ ID NO 354
<211> LENGTH: 20
<212> TYPE: DNA
<213> ORGANISM: Artificial Sequence
<220> FEATURE:
<223> OTHER INFORMATION: Oligonucleotide

<400> SEQUENCE: 354
taggagtgag cgtgtggttg                                          20

<210> SEQ ID NO 355
<211> LENGTH: 20
<212> TYPE: DNA
<213> ORGANISM: Artificial Sequence
<220> FEATURE:
<223> OTHER INFORMATION: Oligonucleotide

<400> SEQUENCE: 355
```
agatgggctg gtaccctctt                                              20

<210> SEQ ID NO 356
<211> LENGTH: 20
<212> TYPE: DNA
<213> ORGANISM: Artificial Sequence
<220> FEATURE:
<223> OTHER INFORMATION: Oligonucleotide

<400> SEQUENCE: 356
gtagctggcg aaaccagaag                                              20

<210> SEQ ID NO 357
<211> LENGTH: 20
<212> TYPE: DNA
<213> ORGANISM: Artificial Sequence
<220> FEATURE:
<223> OTHER INFORMATION: Oligonucleotide

<400> SEQUENCE: 357
ttctggagag aggcaagcag                                              20

<210> SEQ ID NO 358
<211> LENGTH: 20
<212> TYPE: DNA
<213> ORGANISM: Artificial Sequence
<220> FEATURE:
<223> OTHER INFORMATION: Oligonucleotide

<400> SEQUENCE: 358
tcctcacaca tgttgctggt                                              20

<210> SEQ ID NO 359
<211> LENGTH: 20
<212> TYPE: DNA
<213> ORGANISM: Artificial Sequence
<220> FEATURE:
<223> OTHER INFORMATION: Oligonucleotide

<400> SEQUENCE: 359
caagcacaca ggcagatgtt                                              20

<210> SEQ ID NO 360
<211> LENGTH: 20
<212> TYPE: DNA
<213> ORGANISM: Artificial Sequence
<220> FEATURE:
<223> OTHER INFORMATION: Oligonucleotide

<400> SEQUENCE: 360
caatggctcc ccattctcta                                              20

<210> SEQ ID NO 361
<211> LENGTH: 20
<212> TYPE: DNA
<213> ORGANISM: Artificial Sequence
<220> FEATURE:
<223> OTHER INFORMATION: Oligonucleotide

<400> SEQUENCE: 361
ggatgtccat ggagcagaat                                              20

<210> SEQ ID NO 362
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 362
ctttgcttct gccactcctc                                                  20

<210> SEQ ID NO 363
<211> LENGTH: 20
<212> TYPE: DNA
<213> ORGANISM: Artificial Sequence
<220> FEATURE:
<223> OTHER INFORMATION: Oligonucleotide

<400> SEQUENCE: 363
attcagacac agcccagtcc                                                  20

<210> SEQ ID NO 364
<211> LENGTH: 20
<212> TYPE: DNA
<213> ORGANISM: Artificial Sequence
<220> FEATURE:
<223> OTHER INFORMATION: Oligonucleotide

<400> SEQUENCE: 364
ccccacttta caccctgcta                                                  20

<210> SEQ ID NO 365
<211> LENGTH: 20
<212> TYPE: DNA
<213> ORGANISM: Artificial Sequence
<220> FEATURE:
<223> OTHER INFORMATION: Oligonucleotide

<400> SEQUENCE: 365
gggtgacctt ggataagggt                                                  20

<210> SEQ ID NO 366
<211> LENGTH: 20
<212> TYPE: DNA
<213> ORGANISM: Artificial Sequence
<220> FEATURE:
<223> OTHER INFORMATION: Oligonucleotide

<400> SEQUENCE: 366
gagacaggag aggcaggatg                                                  20

<210> SEQ ID NO 367
<211> LENGTH: 20
<212> TYPE: DNA
<213> ORGANISM: Artificial Sequence
<220> FEATURE:
<223> OTHER INFORMATION: Oligonucleotide

<400> SEQUENCE: 367
atcatccaac tcagcaaggg                                                  20

<210> SEQ ID NO 368
<211> LENGTH: 19
<212> TYPE: DNA
<213> ORGANISM: Artificial Sequence
<220> FEATURE:
<223> OTHER INFORMATION: Oligonucleotide

<400> SEQUENCE: 368
gggcttagag aggcaccag                                                   19
```

<210> SEQ ID NO 369
<211> LENGTH: 20
<212> TYPE: DNA
<213> ORGANISM: Artificial Sequence
<220> FEATURE:
<223> OTHER INFORMATION: Oligonucleotide

<400> SEQUENCE: 369
attgaggtgg ccacttatgc                                                  20

<210> SEQ ID NO 370
<211> LENGTH: 20
<212> TYPE: DNA
<213> ORGANISM: Artificial Sequence
<220> FEATURE:
<223> OTHER INFORMATION: Oligonucleotide

<400> SEQUENCE: 370
tcgtagtgct gtggtgaagg                                                  20

<210> SEQ ID NO 371
<211> LENGTH: 20
<212> TYPE: DNA
<213> ORGANISM: Artificial Sequence
<220> FEATURE:
<223> OTHER INFORMATION: Oligonucleotide

<400> SEQUENCE: 371
tggcccacac tcttagcttt                                                  20

<210> SEQ ID NO 372
<211> LENGTH: 20
<212> TYPE: DNA
<213> ORGANISM: Artificial Sequence
<220> FEATURE:
<223> OTHER INFORMATION: Oligonucleotide

<400> SEQUENCE: 372
aacatgtcag aggacccagc                                                  20

<210> SEQ ID NO 373
<211> LENGTH: 20
<212> TYPE: DNA
<213> ORGANISM: Artificial Sequence
<220> FEATURE:
<223> OTHER INFORMATION: Oligonucleotide

<400> SEQUENCE: 373
aagggaagcc aggtctcagt                                                  20

<210> SEQ ID NO 374
<211> LENGTH: 20
<212> TYPE: DNA
<213> ORGANISM: Artificial Sequence
<220> FEATURE:
<223> OTHER INFORMATION: Oligonucleotide

<400> SEQUENCE: 374
cttcccaccc cttaggtctc                                                  20

<210> SEQ ID NO 375
<211> LENGTH: 20
<212> TYPE: DNA
<213> ORGANISM: Artificial Sequence
<220> FEATURE:

<223> OTHER INFORMATION: Oligonucleotide

<400> SEQUENCE: 375
agtaggggtg tgggtgacag                                                    20

<210> SEQ ID NO 376
<211> LENGTH: 20
<212> TYPE: DNA
<213> ORGANISM: Artificial Sequence
<220> FEATURE:
<223> OTHER INFORMATION: Oligonucleotide

<400> SEQUENCE: 376
gccacaggaa aagctaacca                                                    20

<210> SEQ ID NO 377
<211> LENGTH: 20
<212> TYPE: DNA
<213> ORGANISM: Artificial Sequence
<220> FEATURE:
<223> OTHER INFORMATION: Oligonucleotide

<400> SEQUENCE: 377
gttggctgtg gctcctaaag                                                    20

<210> SEQ ID NO 378
<211> LENGTH: 20
<212> TYPE: DNA
<213> ORGANISM: Artificial Sequence
<220> FEATURE:
<223> OTHER INFORMATION: Oligonucleotide

<400> SEQUENCE: 378
cgcactcctc tcgtctaacc                                                    20

<210> SEQ ID NO 379
<211> LENGTH: 20
<212> TYPE: DNA
<213> ORGANISM: Artificial Sequence
<220> FEATURE:
<223> OTHER INFORMATION: Oligonucleotide

<400> SEQUENCE: 379
ccttgtcttt gctacctggc                                                    20

<210> SEQ ID NO 380
<211> LENGTH: 20
<212> TYPE: DNA
<213> ORGANISM: Artificial Sequence
<220> FEATURE:
<223> OTHER INFORMATION: Oligonucleotide

<400> SEQUENCE: 380
tccccatcac cactgtagaa                                                    20

<210> SEQ ID NO 381
<211> LENGTH: 20
<212> TYPE: DNA
<213> ORGANISM: Artificial Sequence
<220> FEATURE:
<223> OTHER INFORMATION: Oligonucleotide

<400> SEQUENCE: 381
ccattccccc tttaccctta                                                    20

```
<210> SEQ ID NO 382
<211> LENGTH: 20
<212> TYPE: DNA
<213> ORGANISM: Artificial Sequence
<220> FEATURE:
<223> OTHER INFORMATION: Oligonucleotide

<400> SEQUENCE: 382
gcaactcagg tccagacaca                                              20

<210> SEQ ID NO 383
<211> LENGTH: 20
<212> TYPE: DNA
<213> ORGANISM: Artificial Sequence
<220> FEATURE:
<223> OTHER INFORMATION: Oligonucleotide

<400> SEQUENCE: 383
ataaactgcc agccaacagc                                              20

<210> SEQ ID NO 384
<211> LENGTH: 20
<212> TYPE: DNA
<213> ORGANISM: Artificial Sequence
<220> FEATURE:
<223> OTHER INFORMATION: Oligonucleotide

<400> SEQUENCE: 384
gagtttgcaa gaccccactc                                              20

<210> SEQ ID NO 385
<211> LENGTH: 20
<212> TYPE: DNA
<213> ORGANISM: Artificial Sequence
<220> FEATURE:
<223> OTHER INFORMATION: Oligonucleotide

<400> SEQUENCE: 385
cgctgcactg taagatccct                                              20

<210> SEQ ID NO 386
<211> LENGTH: 20
<212> TYPE: DNA
<213> ORGANISM: Artificial Sequence
<220> FEATURE:
<223> OTHER INFORMATION: Oligonucleotide

<400> SEQUENCE: 386
aatgcaacct gcttacctgg                                              20

<210> SEQ ID NO 387
<211> LENGTH: 20
<212> TYPE: DNA
<213> ORGANISM: Artificial Sequence
<220> FEATURE:
<223> OTHER INFORMATION: Oligonucleotide

<400> SEQUENCE: 387
acgtatgctg atggggaaac                                              20

<210> SEQ ID NO 388
<211> LENGTH: 21
<212> TYPE: DNA
<213> ORGANISM: Artificial Sequence
<220> FEATURE:
<223> OTHER INFORMATION: Oligonucleotide
```

```
<400> SEQUENCE: 388
caactctttc gtggatctgg a                                              21

<210> SEQ ID NO 389
<211> LENGTH: 20
<212> TYPE: DNA
<213> ORGANISM: Artificial Sequence
<220> FEATURE:
<223> OTHER INFORMATION: Oligonucleotide

<400> SEQUENCE: 389
aggtgggttt acctgaggct                                                20

<210> SEQ ID NO 390
<211> LENGTH: 20
<212> TYPE: DNA
<213> ORGANISM: Artificial Sequence
<220> FEATURE:
<223> OTHER INFORMATION: Oligonucleotide

<400> SEQUENCE: 390
gtgggttttt cacgcctcta                                                20

<210> SEQ ID NO 391
<211> LENGTH: 20
<212> TYPE: DNA
<213> ORGANISM: Artificial Sequence
<220> FEATURE:
<223> OTHER INFORMATION: Oligonucleotide

<400> SEQUENCE: 391
atctcccact tgcctttcct                                                20

<210> SEQ ID NO 392
<211> LENGTH: 20
<212> TYPE: DNA
<213> ORGANISM: Artificial Sequence
<220> FEATURE:
<223> OTHER INFORMATION: Oligonucleotide

<400> SEQUENCE: 392
ccattcctaa tcccaccctt                                                20

<210> SEQ ID NO 393
<211> LENGTH: 20
<212> TYPE: DNA
<213> ORGANISM: Artificial Sequence
<220> FEATURE:
<223> OTHER INFORMATION: Oligonucleotide

<400> SEQUENCE: 393
tgtcctgcac accctgtaga                                                20

<210> SEQ ID NO 394
<211> LENGTH: 20
<212> TYPE: DNA
<213> ORGANISM: Artificial Sequence
<220> FEATURE:
<223> OTHER INFORMATION: Oligonucleotide

<400> SEQUENCE: 394
ggtcctggaa tgcctcacta                                                20

<210> SEQ ID NO 395
<211> LENGTH: 20
```

```
<212> TYPE: DNA
<213> ORGANISM: Artificial Sequence
<220> FEATURE:
<223> OTHER INFORMATION: Oligonucleotide

<400> SEQUENCE: 395
gcatcttcgt gtgagcttga                                              20

<210> SEQ ID NO 396
<211> LENGTH: 20
<212> TYPE: DNA
<213> ORGANISM: Artificial Sequence
<220> FEATURE:
<223> OTHER INFORMATION: Oligonucleotide

<400> SEQUENCE: 396
tgggaagaga caagccatct                                              20

<210> SEQ ID NO 397
<211> LENGTH: 20
<212> TYPE: DNA
<213> ORGANISM: Artificial Sequence
<220> FEATURE:
<223> OTHER INFORMATION: Oligonucleotide

<400> SEQUENCE: 397
gaaagtaagg cagggctct                                               20

<210> SEQ ID NO 398
<211> LENGTH: 20
<212> TYPE: DNA
<213> ORGANISM: Artificial Sequence
<220> FEATURE:
<223> OTHER INFORMATION: Oligonucleotide

<400> SEQUENCE: 398
cccaacccct taccaagaat                                              20

<210> SEQ ID NO 399
<211> LENGTH: 20
<212> TYPE: DNA
<213> ORGANISM: Artificial Sequence
<220> FEATURE:
<223> OTHER INFORMATION: Oligonucleotide

<400> SEQUENCE: 399
tacaggttca aggtttgggg                                              20

<210> SEQ ID NO 400
<211> LENGTH: 19
<212> TYPE: DNA
<213> ORGANISM: Artificial Sequence
<220> FEATURE:
<223> OTHER INFORMATION: Oligonucleotide

<400> SEQUENCE: 400
atgcatcagc aagcaggac                                               19

<210> SEQ ID NO 401
<211> LENGTH: 20
<212> TYPE: DNA
<213> ORGANISM: Artificial Sequence
<220> FEATURE:
<223> OTHER INFORMATION: Oligonucleotide

<400> SEQUENCE: 401
```

```
gcctgcttgt ggacctactc                                              20

<210> SEQ ID NO 402
<211> LENGTH: 20
<212> TYPE: DNA
<213> ORGANISM: Artificial Sequence
<220> FEATURE:
<223> OTHER INFORMATION: Oligonucleotide

<400> SEQUENCE: 402
agagcggaaa agccatacct                                              20

<210> SEQ ID NO 403
<211> LENGTH: 20
<212> TYPE: DNA
<213> ORGANISM: Artificial Sequence
<220> FEATURE:
<223> OTHER INFORMATION: Oligonucleotide

<400> SEQUENCE: 403
acagcctcct taggctccag                                              20

<210> SEQ ID NO 404
<211> LENGTH: 20
<212> TYPE: DNA
<213> ORGANISM: Artificial Sequence
<220> FEATURE:
<223> OTHER INFORMATION: Oligonucleotide

<400> SEQUENCE: 404
aacacttgac cgctagcacc                                              20

<210> SEQ ID NO 405
<211> LENGTH: 20
<212> TYPE: DNA
<213> ORGANISM: Artificial Sequence
<220> FEATURE:
<223> OTHER INFORMATION: Oligonucleotide

<400> SEQUENCE: 405
gttgaggctg tgctgtcaaa                                              20

<210> SEQ ID NO 406
<211> LENGTH: 20
<212> TYPE: DNA
<213> ORGANISM: Artificial Sequence
<220> FEATURE:
<223> OTHER INFORMATION: Oligonucleotide

<400> SEQUENCE: 406
agccgatgca agcctaacta                                              20

<210> SEQ ID NO 407
<211> LENGTH: 20
<212> TYPE: DNA
<213> ORGANISM: Artificial Sequence
<220> FEATURE:
<223> OTHER INFORMATION: Oligonucleotide

<400> SEQUENCE: 407
cactgcttca ccccataggt                                              20

<210> SEQ ID NO 408
<211> LENGTH: 20
<212> TYPE: DNA
<213> ORGANISM: Artificial Sequence
```

```
<220> FEATURE:
<223> OTHER INFORMATION: Oligonucleotide

<400> SEQUENCE: 408
atggcaaatg ctctgaggtc                                               20

<210> SEQ ID NO 409
<211> LENGTH: 20
<212> TYPE: DNA
<213> ORGANISM: Artificial Sequence
<220> FEATURE:
<223> OTHER INFORMATION: Oligonucleotide

<400> SEQUENCE: 409
acacgaatag aggcacccag                                               20

<210> SEQ ID NO 410
<211> LENGTH: 18
<212> TYPE: DNA
<213> ORGANISM: Artificial Sequence
<220> FEATURE:
<223> OTHER INFORMATION: Oligonucleotide

<400> SEQUENCE: 410
aaccctgaga tctgcccc                                                 18

<210> SEQ ID NO 411
<211> LENGTH: 20
<212> TYPE: DNA
<213> ORGANISM: Artificial Sequence
<220> FEATURE:
<223> OTHER INFORMATION: Oligonucleotide

<400> SEQUENCE: 411
ttttcaggag cagaggagga                                               20

<210> SEQ ID NO 412
<211> LENGTH: 20
<212> TYPE: DNA
<213> ORGANISM: Artificial Sequence
<220> FEATURE:
<223> OTHER INFORMATION: Oligonucleotide

<400> SEQUENCE: 412
agcggaggga aaactgatct                                               20

<210> SEQ ID NO 413
<211> LENGTH: 20
<212> TYPE: DNA
<213> ORGANISM: Artificial Sequence
<220> FEATURE:
<223> OTHER INFORMATION: Oligonucleotide

<400> SEQUENCE: 413
cctcaaagaa tgctgaaggg                                               20

<210> SEQ ID NO 414
<211> LENGTH: 20
<212> TYPE: DNA
<213> ORGANISM: Artificial Sequence
<220> FEATURE:
<223> OTHER INFORMATION: Oligonucleotide

<400> SEQUENCE: 414
ccttctgagt cctcccacag                                               20
```

```
<210> SEQ ID NO 415
<211> LENGTH: 20
<212> TYPE: DNA
<213> ORGANISM: Artificial Sequence
<220> FEATURE:
<223> OTHER INFORMATION: Oligonucleotide

<400> SEQUENCE: 415
tgaccttgaa ggatggaagg                                           20

<210> SEQ ID NO 416
<211> LENGTH: 20
<212> TYPE: DNA
<213> ORGANISM: Artificial Sequence
<220> FEATURE:
<223> OTHER INFORMATION: Oligonucleotide

<400> SEQUENCE: 416
cccaggaccc aaaatcttct                                           20
```